(12) United States Patent
Kim

(10) Patent No.: US 7,691,874 B2
(45) Date of Patent: Apr. 6, 2010

(54) NEUROPROTECTIVE PROPERTIES OF DEXTROROTATORY MORPHINANS

(75) Inventor: Hyoung-Chun Kim, Neurotoxicology Program, College of Pharmacy, Kangwon National University, Chunchon (KR) 200-701

(73) Assignees: Hyoung-Chun Kim, Yongin (KR); Green Cross Corp., Yongin (KR)

( * ) Notice: Subject to any disclaimer, the term of this patent is extended or adjusted under 35 U.S.C. 154(b) by 1363 days.

(21) Appl. No.: 10/908,472

(22) Filed: May 13, 2005

(65) Prior Publication Data
US 2005/0256147 A1  Nov. 17, 2005

Related U.S. Application Data

(60) Provisional application No. 60/571,214, filed on May 14, 2004, provisional application No. 60/573,424, filed on May 21, 2004, provisional application No. 60/680,444, filed on May 11, 2005.

(51) Int. Cl.
*A01N 43/42* (2006.01)
*A61K 31/44* (2006.01)

(52) U.S. Cl. ..................................... 514/289
(58) Field of Classification Search .................. 514/289
See application file for complete search history.

(56) References Cited

U.S. PATENT DOCUMENTS

| | | | |
|---|---|---|---|
| 3,912,761 A * | 10/1975 | Den Hollander et al. | .... 549/364 |
| 4,788,055 A | 11/1988 | Fischer et al. | |
| 4,816,264 A | 3/1989 | Phillips et al. | |
| 4,828,836 A | 5/1989 | Elger et al. | |
| 4,834,965 A | 5/1989 | Martani et al. | |
| 4,834,985 A | 5/1989 | Elger et al. | |
| 4,996,047 A | 2/1991 | Kelleher et al. | |
| 5,071,646 A | 12/1991 | Malkowska et al. | |
| 5,133,974 A | 7/1992 | Paradissis et al. | |
| 5,321,012 A | 6/1994 | Mayer et al. | |
| 5,863,927 A * | 1/1999 | Smith et al. | .................. 514/289 |
| 6,057,373 A | 5/2000 | Fogel | |
| 6,228,863 B1 | 5/2001 | Palermo et al. | |
| 6,475,494 B2 | 11/2002 | Kaiko et al. | |
| 2002/0103109 A1 | 8/2002 | Glick et al. | |

FOREIGN PATENT DOCUMENTS

WO    WO 03/097608 A2    11/2003

OTHER PUBLICATIONS

Dorwald FZ, "Side Reactions in Organic Synthesis," Wiley VCH Verlag GmbH & KGaA, 2005, p. 5.*
Wilkinson GR, Chapter 1 Pharmacokinetics, Goodman & Gilman's The Pharmacological Basis of Therapeutics 10th ed., Hardman JG, Limbird LE, and Gilman AG Eds, McGraw-Hill, New York, 2001, pp. 3-30 (pp. 3, 5, and 6 provided).*
Chase TN, Oh JD, and Konitsiotis S, "Antiparkinsonian and antidyskinetic activity of drugs targeting central glutamatergic mechanisms," Journal of Neurology, Apr. 2000, 247 (Suppl 2), II36-42.*

(Continued)

*Primary Examiner*—San-ming Hui
*Assistant Examiner*—Paul Zarek
(74) *Attorney, Agent, or Firm*—Joseph H. Kim; JHK Law

(57) ABSTRACT

The present application discloses a pharmaceutical composition for treating Parkinson's disease and psychotropic intoxication/abusive potential, which contains a morphinan compound.

5 Claims, 35 Drawing Sheets

Dextromethorphan (DM)

Dextrorphan (DX)

3-Hydroxymorphinan (HM)

3-Allyloxy-17-methyl-morphinan (AM)

3-cyclopropylmethoxy-17-methyl-morphinan (CM)

3-methyl-17-methyl-morphinan (DF)

OTHER PUBLICATIONS

Kim, H-C. et al., "New morphinan derivatives with negligible psychotropic effects attenuate convulsions induced by maximal electroshock in mice," Life Sciences (2003) 72:1883-1895.

Zhang, W. et al., "3-Hydroxymorphinan is neurotrophic to dopaminergic neurons and is also neuroprotective against LPS-induced neurotoxicity," The FASEB J (2005) 19:395-397.

* cited by examiner

Dextromethorphan (DM)   Dextrorphan (DX)   3-Hydroxymorphinan (HM)

3-Allyloxy-17-methyl-morphinan (AM)   3-cyclopropylmethoxy-17-methyl-morphinan (CM)   3-methyl-17-methyl-morphinan (DF)

A

B

A

B

MPTP = MPTP 20 mg/kg, s.c.
HM = 3-Hydroxymorphinan 20 mg/kg, i.p.
Carbidopa = Carbidopa 20 mg/kg, p.o.
L-dopa = L-dopa 200 mg/kg, p.o.

LPS = Bilateral intrastriatal injection (one side: 2 μg × 2)
HM = 3-Hydroxymorphinan 20 mg/kg, i.p.
Carbidopa = Carbidopa 20 mg/kg, p.o.
L-dopa = L-dopa 200 mg/kg, p.o.

MA = MA 7.5 mg/kg, i.p.
HM = 3-Hydroxymorphinan 20 mg/kg, i.p.
Carbidopa = Carbidopa 20 mg/kg, p.o.
L-dopa = L-dopa 200 mg/kg, p.o.
RT = Rectal Temperature.

A

B

NEUROPROTECTIVE PROPERTIES OF DEXTROROTATORY MORPHINANS

BACKGROUND OF THE INVENTION

1. Field of the Invention

The invention relates to a neuroprotective compound. The invention further relates to a morphinan compound used to treat a variety of neurological conditions, including Parkinson's disease or the symptoms of Parkinson's disease, learning and memory impairment in Alzheimer's disease, the symptoms of intoxication and or dependence on such narcotics as cocaine, morphine, and methamphetamine. The invention also relates to pharmaceutical formulations for such morphinan compounds.

2. General Background and State of the Art:

Dextromethorphan (DM; 3-methoxy-17-methylmorphinan) is a non-narcotic morphinan derivative widely used as an antitussive for almost 40 years. It has attracted attention due to its neuroprotective properties (5, 9, 17-20, 23, 24, 26, 27, 33, 34, 46, 50, 51). However, case reports of toxicity in children (43, 45); and phencyclidine (PCP)-like psychotomimetic reactions (8, 12, 44, 53) associated with high-dose DM ingestion are likely attributable to dextrorphan (DX; 3-hydroxy-17-methylmorphinan), which is a major metabolite of DM (50, 51). The DM dose for the neuroprotective effects (17-20, 50, 51) is much higher than the cough suppressant dosage. Clinically, high doses of DM can produce psychotropic effects (8, 12, 19, 43-45, 53). Furthermore, DM has been recognized as the object of drug-seeking behavior in several countries (19, 43, 45). Previously, it was suggested that DM potentiates the psychotropic effects induced by cocaine (13, 25), and that DM itself might produce psychotoxic effects in mice (12, 15, 20, 24, 27). Moreover, it was demonstrated that chronic DM administration perturbs the cellular immune response (16), and this is similar to the immunosuppressive effects caused by PCP (19). In the past decade, investigators have documented that DM has an N-methyl-D-aspartate (NMDA) receptor antagonistic effect with regard to neuroprotection (5, 9, 19, 20, 50). Therefore, a DM analogue that retains its neuroprotective activities without being converted into DX in vivo would be highly useful (7, 24, 27, 46, 50, 51).

Recently, a series of compounds that are modified in positions 3 and 17 of the morphinan ring system were synthesized, with the intention of developing compounds that retain anticonvulsant activity/neuroprotective property with negligible psychotropic effects (24). To reduce the PCP-like behavioral side effects (24, 39, 46), while retaining the anticonvulsant/neuroprotective effects, a series of 3- and 17-substituted morphinans were prepared that are structurally similar to DM, but are either not expected to be metabolized into DX or are expected to do so at a reduced rate compared to DM (24).

1-Methyl-4-phenyl-1,2,5,6-tetrahydropyridine (MPTP)(3, 40), lipopolysaccharide (LPS) (10, 28, 40) and methamphetamine (MA) (21, 22, 29) all cause degeneration of nigrostriatal dopaminergic neurons and loss of striatal dopamine in rodents, primates and other species (40). Accumulating evidence indicates that DM exerts antiparkinsonian effects in vivo (14, 47) and in vitro (33). In addition, DM improves levodopa associated motor fluctuations and dyskinesias in Parkinson's disease, although the narrow therapeutic index and psychotropic effects of DM limit its clinical usefulness (52).

Accordingly, there is a need in the neurobiology industry for a neuroprotective pharmaceutical compound that is substantially free of unacceptable side-effects, such as a compound that can treat the symptoms of Parkinson's disease without causing other negative psychological effects.

SUMMARY OF THE INVENTION

The invention is directed to a neuroprotective compound or a composition comprising a neuroprotective compound. In one aspect, the invention is directed to a pharmaceutical composition for treating Parkinson's disease, comprising an effective anti-Parkinsonism amount of 3-hydroxymorphinan (HM) or a morphinan derivative of 3-hydroxymorphinan (HM), in which the 3 and 17 positions are derivatized, including without limitation 3-allyloxy-17-methylmorphinan (AM), 3-cyclopropylmethoxy-17-methylmorphinan (CM), and 3-methyl-17-methyl-morphinan (DF) or a physiologically acceptable salt thereof together with a pharmaceutical carrier or excipient. The composition may comprise a mixture of the morphinan compounds. And in particular, the invention is directed to 3-hydroxymorphinan. The composition may further comprise other neuroprotective agents or any other pharmacologically acceptable compound. The composition may be in a sustained release dosage form.

In another aspect of the invention, the invention is directed to a unit dosage formulation for treatment of Parkinson's disease, comprising a morphinan described above or a pharmaceutically acceptable salt thereof in a form that is designed for oral ingestion by humans, wherein the morphinan or salt thereof is present at a dosage which renders the morphinan therapeutically effective in substantially reducing symptoms of Parkinson's disease, without causing unacceptable side effects. The unit dosage formulation may comprise a digestible capsule, which encloses the morphinan or pharmaceutically acceptable salt thereof. In such a formulation, it is contemplated that morphinan content may be about 250 milligrams/day or less.

In yet another aspect, the invention is directed to a method of treating Parkinson's disease or the symptoms of Parkinson's disease comprising administering to a patient or animal in need of such treatment an effective anti-Parkinsonism amount of the composition described above. In this treatment method, the composition may comprise a mixture of the morphinan compounds described above. In particular, the morphinan compound may be 3-hydroxymorphinan. Further, in this method, the composition may be in a sustained release dosage form. Moreover, the composition may comprise a digestible capsule, which encloses the morphinan or pharmaceutically acceptable salt thereof. In addition, the composition may be administered at about 250 milligrams/day or less. And the composition may further comprise a neuroprotective agent.

In still another aspect, the invention is directed to a method of preventing decrease of dopamine production in substantia nigra of a subject comprising administering to the subject a protective effective amount of the composition described above.

The present invention is also directed to a pharmaceutical composition for treating or preventing a symptom of Alzheimer's disease comprising an effective anti-Alzheimer's disease amount of 3-hydroxymorphinan (HM) or a morphinan derivative of 3-hydroxymorphinan (HM), in which the 3 and 17 positions are derivatized, including without limitation 3-allyloxy-17-methylmorphinan (AM), 3-cyclopropylmethoxy-17-methylmorphinan (CM), and 3-methyl-17-methyl-morphinan (DF) or a physiologically acceptable salt thereof together with a pharmaceutical carrier or excipient. The composition may comprise a mixture of the morphinan compounds. And in particular, the invention is directed to 3-hydroxymorphinan. The composition may further comprise other neuroprotective agents or any other pharmacologically acceptable compound. The composition may be in a sustained release dosage form. In particular, the learning and memory impairment related to Alzheimer's disease may be treated. In this regard, the invention is also directed to a method for treating or preventing learning and memory impairment related to Alzheimer's disease comprising administering to a patient or animal in need of such treatment an effective anti-Alzheimer's amount of the composition described above.

In another aspect, the invention is also directed to a pharmaceutical composition for treating a symptom of narcotics or psychotropic agent intoxication or dependence comprising an effective anti-intoxication amount of 3-hydroxymorphinan (HM) or a morphinan derivative of 3-hydroxymorphinan (HM), in which the 3 and 17 positions are derivatized, including without limitation 3-allyloxy-17-methylmorphinan (AM), 3-cyclopropylmethoxy-17-methylmorphinan (CM), and 3-methyl-17-methyl-morphinan (DF) or a physiologically acceptable salt thereof together with a pharmaceutical carrier or excipient. The composition may comprise a mixture of the morphinan compounds. And in particular, the invention is directed to 3-hydroxymorphinan. The composition may further comprise other neuroprotective agents or any other pharmacologically acceptable compound. The composition may be in a sustained release dosage form. And in this regard, the invention is directed to a method for treating narcotics intoxication comprising administering to a patient or animal in need of such treatment an effective anti-intoxication amount of the above-described composition. In particular, the narcotics intoxicant may be without limitation cocaine, morphine or methamphetamine.

The invention is also directed to a method for treating narcotics dependence comprising administering to a patient or animal in need of such treatment an effective anti-dependent amount of the above-described composition. In particular, the narcotics dependence may be without limitation cocaine, morphine or methamphetamine dependence.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
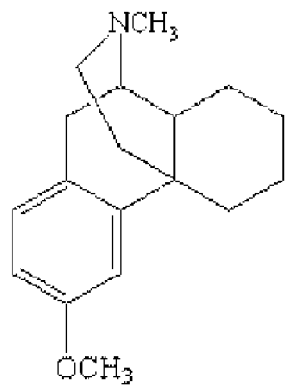
FIG. 1 shows chemical structures of exemplified dextrorotatory morphinan analogs.
Figure 1:
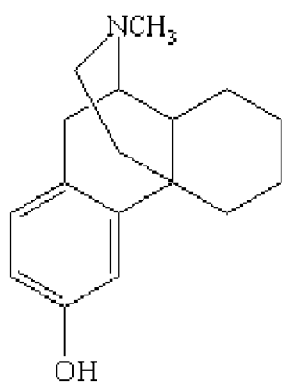
Figure 1:
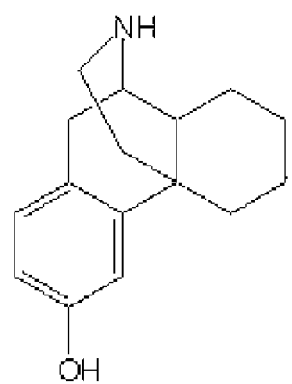
Figure 1:
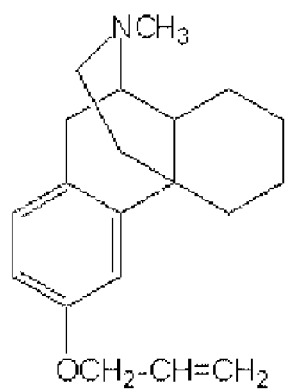
Figure 1:
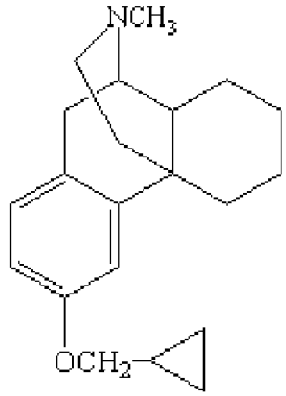
Figure 1:
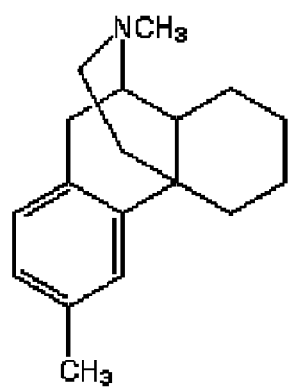

In the present application, "a" and "an" are used to refer to both single and a plurality of objects. As used herein, administration "in combination with" one or more further therapeutic agents includes simultaneous (concurrent) and consecutive administration in any order.

As used herein, "effective amount" is an amount sufficient to effect beneficial or desired clinical or biochemical results. An effective amount can be administered one or more times. For purposes of this invention, an effective amount of a morphinan compound is an amount that is sufficient to palliate, ameliorate, stabilize, reverse, slow or delay the progression of a disease state or condition. In a preferred embodiment of the invention, the "effective amount" is defined as an amount of compound capable of preventing decrease in formation of dopamine in substantia nigra, and is an amount that substantially reduces the symptoms of Parkinson's disease. Other forms of effective amount may be for the treatment or prevention of the learning or memory impairment related to Alzheimer's disease. Further, in another form, the effective amount may refer to an amount that is effective to treat the symptoms of intoxication from narcotics, wherein such symptoms include without limitation analgesia, euphoria, respiratory depression, miosis, sedation, dysphoria, hallucinations, psychosis, and seizures. The effective amount may also refer to an amount that may be used to substantially alleviate or relieve the dependence of an individual on narcotics such as without limitation cocaine, morphine or methamphetamine. In yet another embodiment, the "effective amount" is defined as the neuroprotective effective amount of the morphinan.

As used herein, administration "in combination with" one or more further therapeutic agents includes simultaneous (concurrent) and consecutive administration in any order.

As used herein, "mammal" or "subject" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "neuroprotective" agent refers to drugs or chemical agents intended to prevent damage to the brain or spinal cord from ischemia, stroke, convulsions, or trauma. Some must be administered before the event, but others may be effective for some time after. They act by a variety of mechanisms, but often directly or indirectly minimize the damage produced by endogenous excitatory amino acids. Neuroprotection also includes protection against neurodegeneration and neurotoxins. Further, by "neuroprotective" it is meant to include intervention that slows or halts the progression of neuronal degeneration. Neuroprotection may also be used for prevention or progression of a disease if it can be identified at a presymptomatic stage.

As used herein, "Parkinson's disease" refers to a chronic progressive nervous disease chiefly of later life that is linked to decreased dopamine production in the substantia nigra. Symptoms include stooped posture, resting tremor, weakness of resting muscles, a shuffling gait, speech impediments, movement difficulties and an eventual slowing of mental processes and dementia.

Morphinan Analogues

The neuroprotective morphinan analogues or derivatives of the invention may be those that are substituted at the 3 and 17 positions of 3-hydroxymorphinan. Such analogues may include without limitation substitutions at the 3 position with substituted O, substituted N, halogen, alkyl, including ethyl, propyl, and so forth. The nitrogen group at 17 position may be derivatized with a variety of groups as well. Examples of the inventive compounds used for neuroprotective purposes are present below as well as in the Preparative Examples section in the present application.

Synthesis of Derivatives from 3-Hydroxymorphinan Preserving O

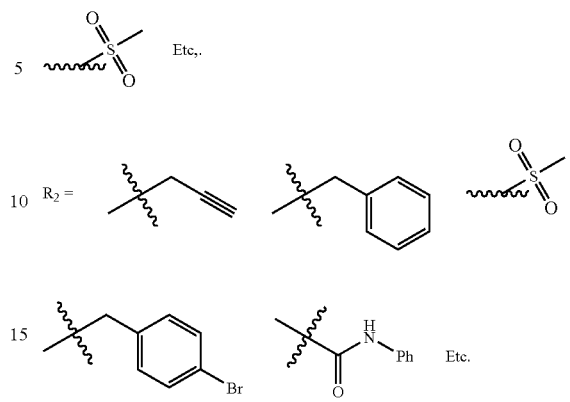

Compounds with Substitution of O at Position 3

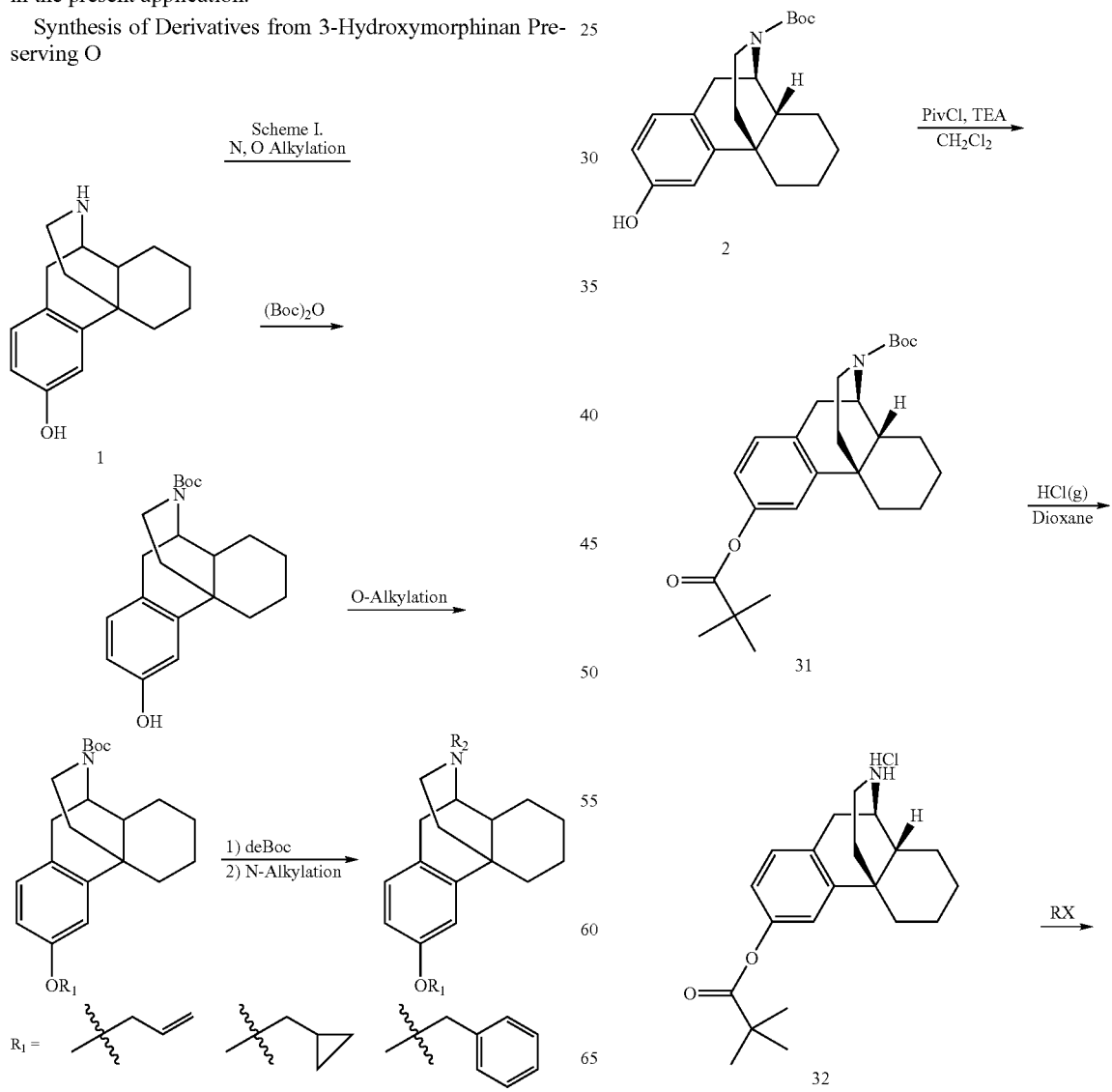

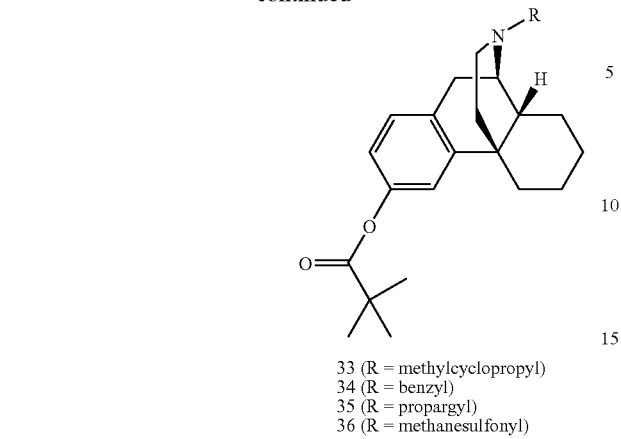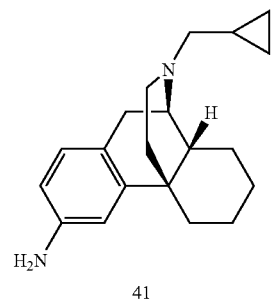
1) Synthesis of 3-Aminomorphinan Derivatives
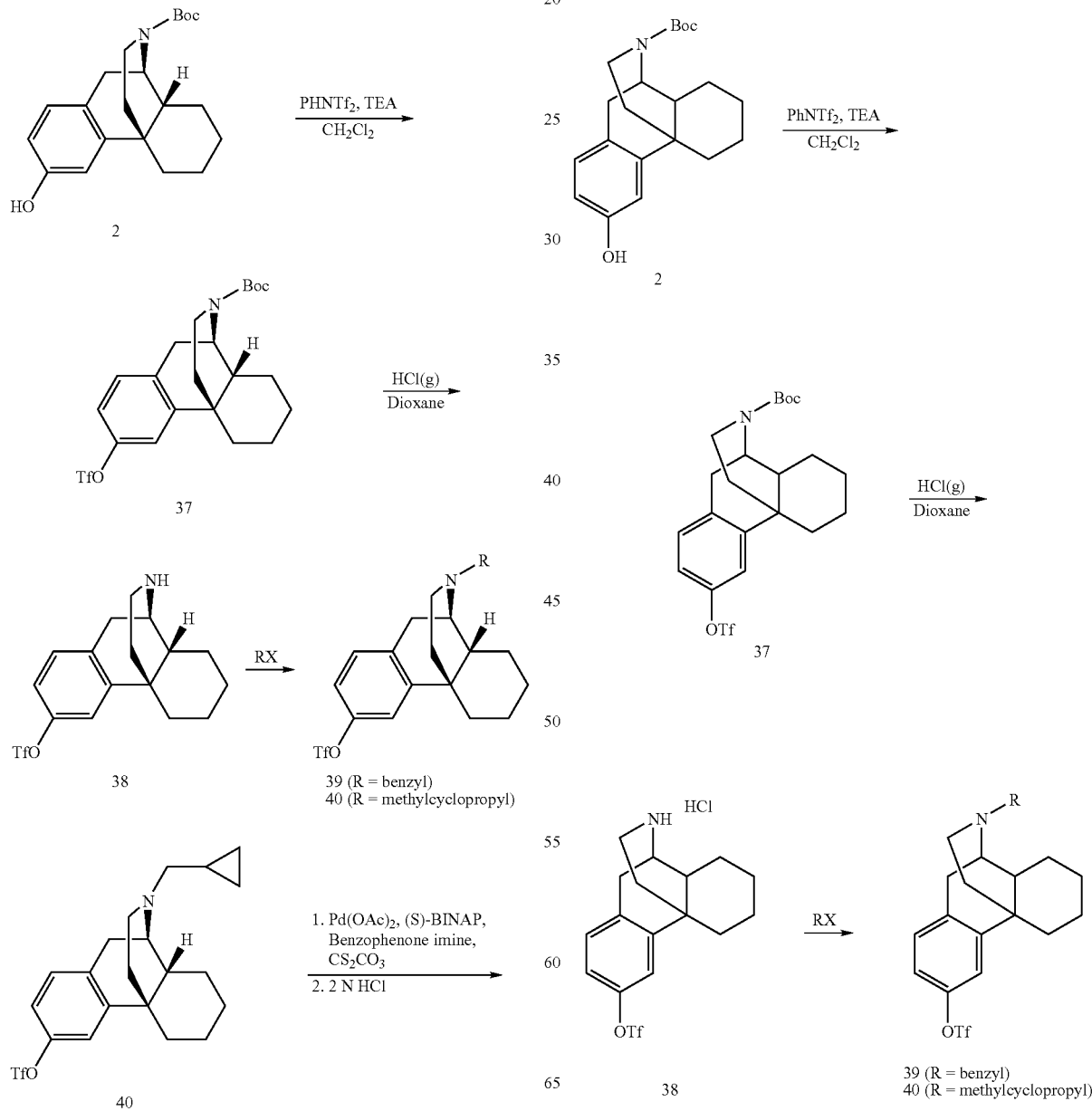

-continued

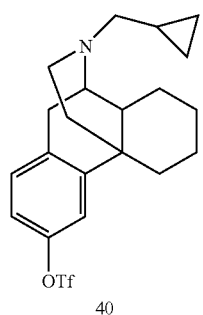 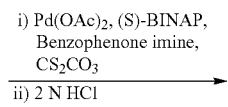
40

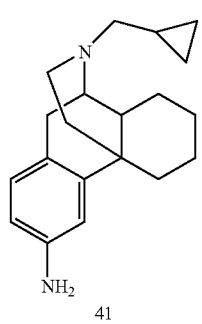  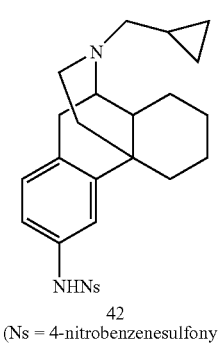
41　　　　　42
(Ns = 4-nitrobenzenesulfonyl)

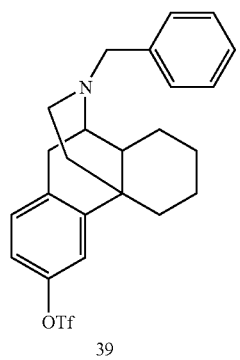 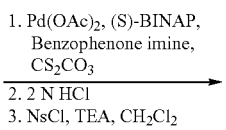

39

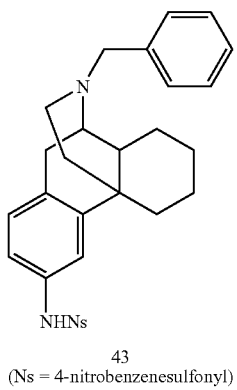
43
(Ns = 4-nitrobenzenesulfonyl)

2) Synthesis of 3-Halogen-Substituted Morphinan Derivatives

Synthesis of halogen compounds and hydroxymethyl derivatives by introducing tin derivatives at position 3 as shown in Scheme 3 below resulted very low yield and the desired compound could not be obtained from limited amount of the starting material.

Scheme 3

 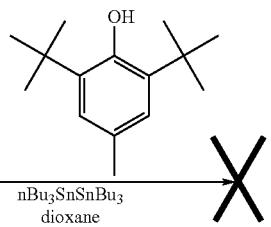

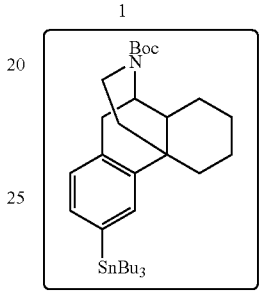 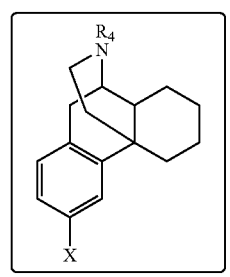

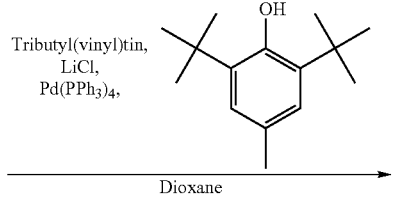

3) Synthesis of 3-Ethylmorphinan Derivatives

Since 3-Halogen-substitued compounds could not be obtained from 2) above, vinyl group was directly added to position 3 to obtain similar derivatives. Introduction of vinyl group was successful and several derivatives were synthesized as shown in Scheme 4 below.

Scheme 4

37

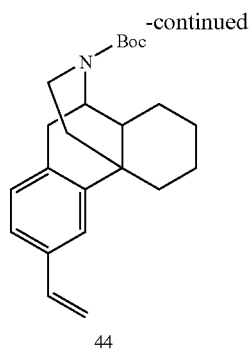
44
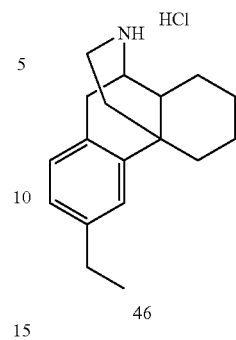
46
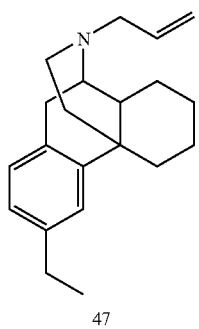
47
H₂, Pd/C / MeOH
Allyl Bromide, K₂CO₃ / DMF
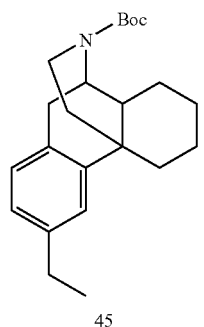
45
HCl(g) / Dioxane
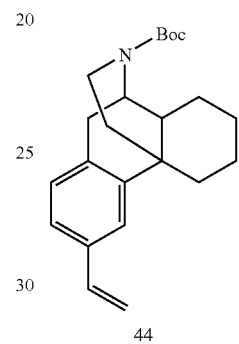
44
NMO, OsO₄ / Acetone:H₂O = 2:1
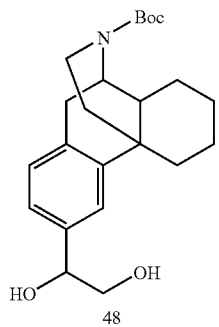
48
List of Exemplified Compounds
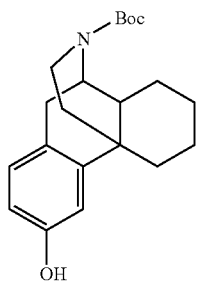
2
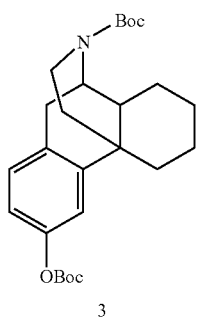
3

-continued
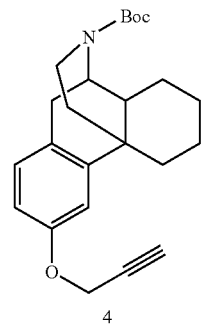
4
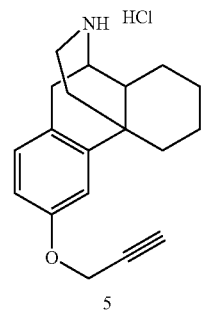
5
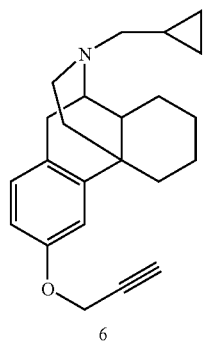
6
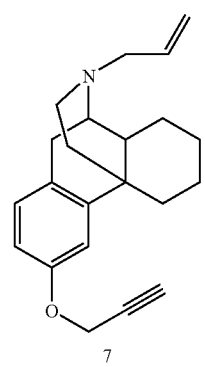
7

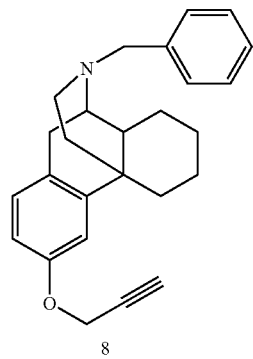
8
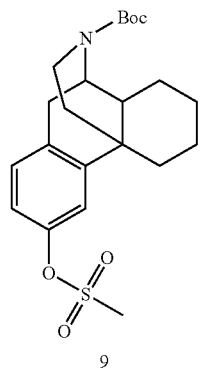
9
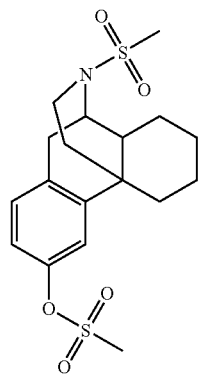
11
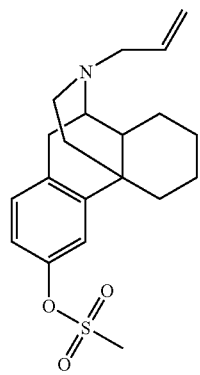
12

-continued
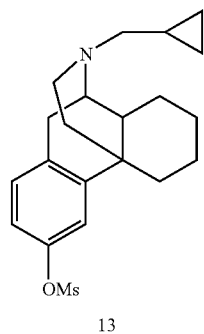
13
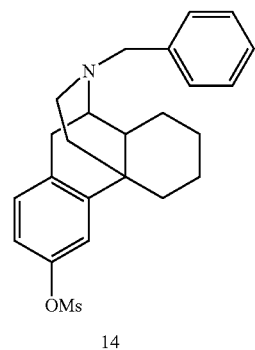
14
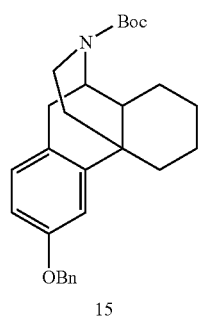
15
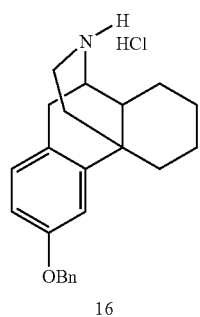
16

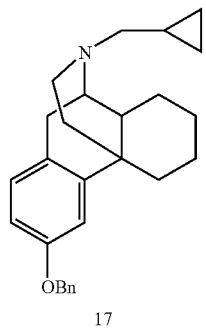
17
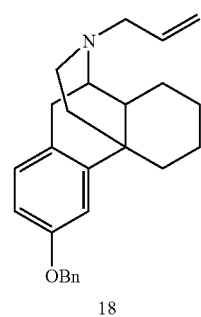
18
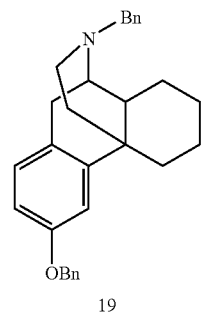
19
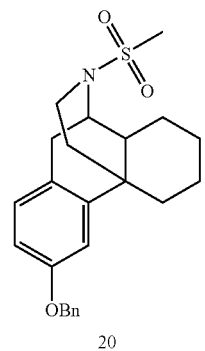
20

-continued
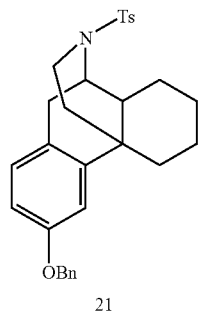
21
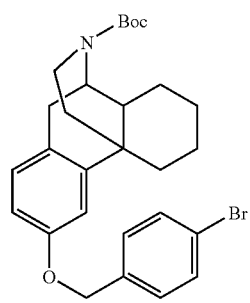
22
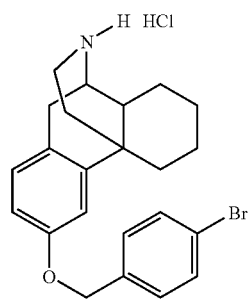
23
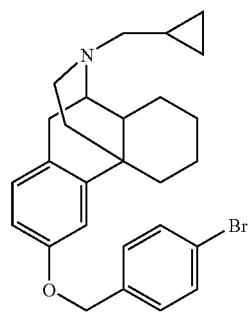
24

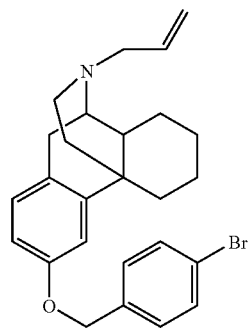
25
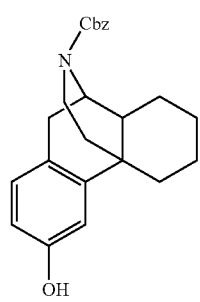
26
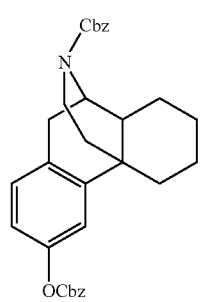
27
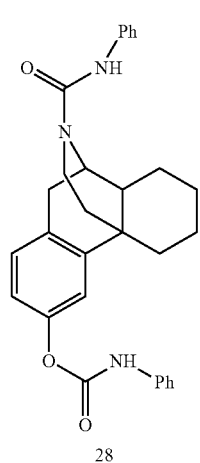
28

-continued
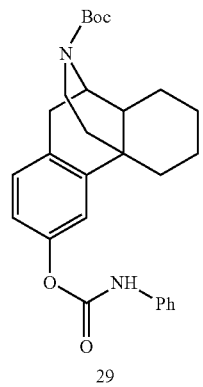
29
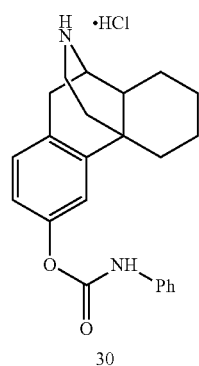
30
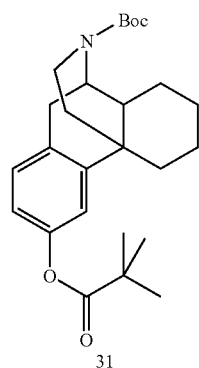
31
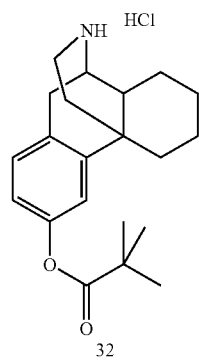
32

-continued
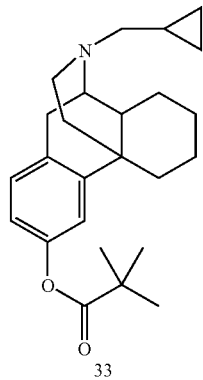
33
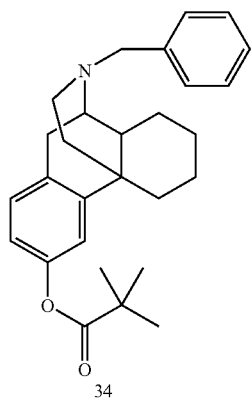
34
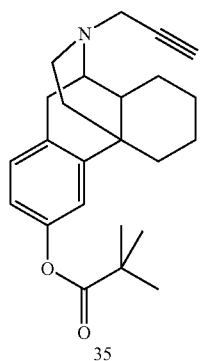
35
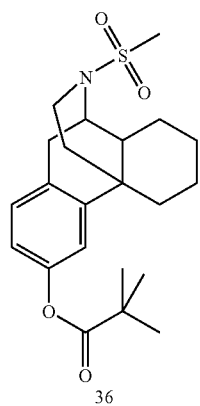
36

-continued
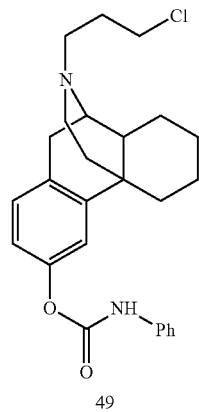
49
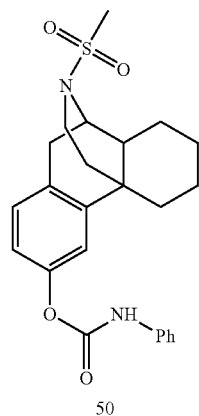
50
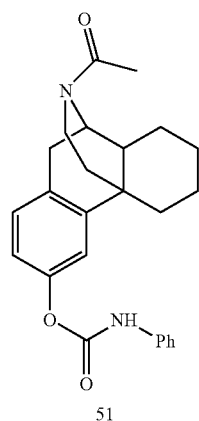
51
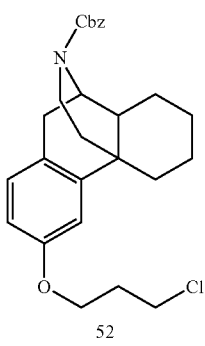
52

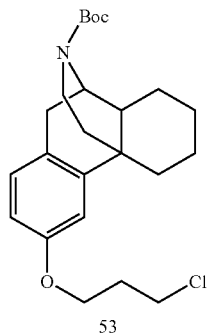
53
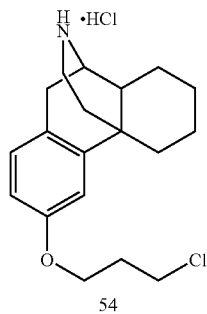
54
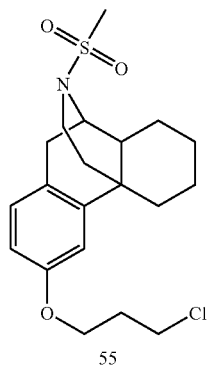
55
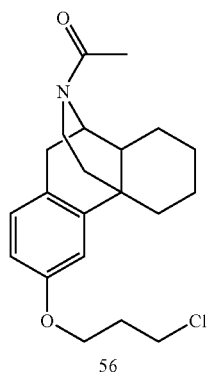
56

-continued
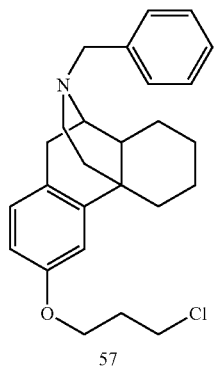
57
| NO | Compound Formula | NMR | Amount (mg) |
|---|---|---|---|
| 2 | Structure with Boc and OH; $C_{21}H_{29}NO_3$; Mol. Wt.: 343.46 | δ7.04~7.18 (3H, m), 3.73(2H, m), 3.68(1H, m), 3.08 (2H, m), 2.15 (1H, m), 1.83(2H, m), 1.70(2H, 4m), 1.44 (9H, s), 1.15~1.38 (6H, m) | 1 |
| 3 | Structure with Boc and OBoc; $C_{26}H_{37}NO_5$; Mol. Wt.: 443.58 | δ6.83~7.08 (3H, m), 4.30 (0.50H, br) 4.00 (0.50H, br), 3.85(0.50H, m), 3.68 (0.50H, m), 3.05~3.25 (1H, m), 2.50~2.70(2H, m), 1.65~1.80 (5H, br), 1.57 (9H, s), 1.49 (9H, s), 1.15~1.40 (6H, m) | 9 |
| 4 | Structure with NBoc and O-propargyl; $C_{24}H_{31}NO_3$; Mol. Wt.: 381.51 | δ7.04~6.89 (3H, m), 4.70(2H, s), 4.33(0.5H, br), 4.18 (0.5H, m), 3.90 (0.5H, d), 3.73(0.5H, d), 3.15~3.07(1H, m), 2.65 (2H, s), 2.49 (1H, s), 2.30 (1H, br), 1.83 (2H, m), 1.60 (2H, m), 1.44~1.47 (9H, s), 1.15~1.30 (6H, m) | 1.4 |

-continued
| | | | |
|---|---|---|---|
| 5 | 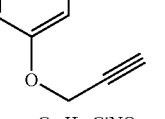<br>C₁₉H₂₄ClNO<br>Mol. Wt.: 317.85 | (MeOD) δ6.93~7.19 (3H, m), 4.75(2H, s), 3.32(2H, m), 3.15~3.07(1H, m), 2.98 (2H, m), 2.78 (1H, m), 2.49 (1H, s), 1.15~1.80 (10H, m) | 3.6 |
| 6 | 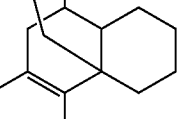<br>C₂₃H₂₉NO<br>Mol. Wt.: 335.48 | δ7.00~6.76 (3H, m), 4.70(2H, s), 3.18 (2H, br), 2.75 (1H, m), 2.68 (1H, m), 2.48 (1H, d), 2.35 (2H, m), 2.00 (1H, m), 1.86(2H, m), 1.63 (2H, br), 1.25~1.60(6H, m), 0.95 (1H, m), 0.58 (2H, s), 0.25 (2H, m) | 2 |
| 7 | 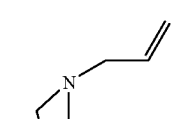<br>C₂₂H₂₇NO<br>Mol. Wt.: 321.46 | δ6.73~7.09 (3H, m), 5.90 (1H, m), 5.14~5.20 (2H, m), 4.64 (2H, m), 3.17(2H, m), 2.94 (2H, m), 2.85 (1H, m), 2.55 (1H, d), 2.53 (2H, m), 1.83 (2H, t), 1.63 (2H, hr), 1.20~1.48 (6H, m) | 4.7 |
| 8 | 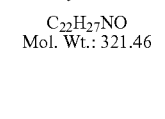<br>C₂₆H₂₉NO<br>Mol. Wt.: 371.51 | δ6.73~7.49 (8H, m), 4.70 (2H, s), 3.68 (2H, br), 3.05(2H, m), 2.85 (1H, br), 2.60 (2H, br), 2.49 (1H, m), 2.30 (1H, m), 1.13~1.80(10H, m) | 1.7 |

-continued
| | | | |
|---|---|---|---|
| 9 | 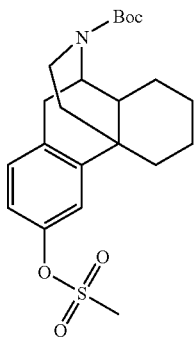
C$_{22}$H$_{31}$NO$_5$S
Mol. Wt.: 421.55 | δ7.07~7.23 (3H, m), 4.33 (0.5H, br), 4.18 (0.5H, m), 3.90 (0.5H, d), 3.73(0.5H, d), 3.30 (1H, br), 3.14 (3H, s), 2.60 (1H, m), 2.55 (1H, m), 2.30 (1H, m), 1.73 (2H, m), 1.60 (2H, br), 1.44~1.47 (9H, s), 1.10~1.40 (6H, m) | 1.6 |
| 11 | 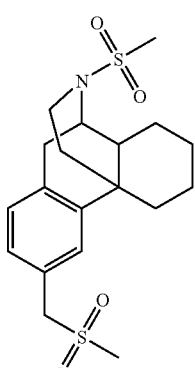
C$_{19}$H$_{27}$NO$_4$S$_2$
Mol. Wt.: 397.55 | δ7.08~7.30 (3H, m), 4.03(1H, br), 3.68 (1H, m), 3.30 (1H, m), 3.18 (3H, s), 2.86 (3H, m), 2.83 (1H, s), 2.60(1H, m), 2.35 (1H, m), 1.68~1.80 (4H, m), 1.25~1.60 (6H, m) | 2.6 |
| 12 | 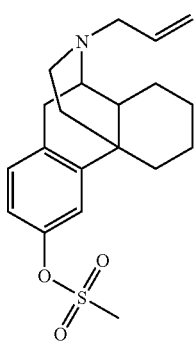
C$_{21}$H$_{29}$NO$_2$S
Mol. Wt.: 359.53 | δ6.85~7.19 (3H, m), 5.85 (1H, br), 5.14~5.20 (2H, m), 3.17 (2H, m), 3.07 (3H, s), 2.80 (2H, m), 2.40 (2H, m), 2.35 (1H, d), 1.60~1.90 (4H, m), 1.20~1.48 (6H, m) | 1.8 |
| 13 | 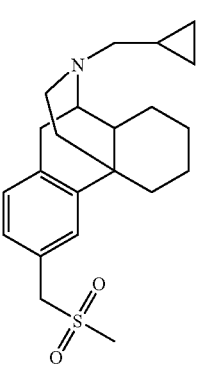
C$_{22}$H$_{31}$NO$_2$S
Mol. Wt.: 373.55 | δ6.85~7.19 (3H, m), 3.14 (3H, s), 2.99 (1H, m), 2.80 (2H, m), 2.60~2.78 (2H, m), 2.50 (1H, br), 2.20 (2H, s), 1.70 (2H, br), 1.20~1.48 (8H, m), 0.90 (1H, m), 0.50 (2H, m), 0.17 (2H, m) | 1 |

-continued
| | | |
|---|---|---|
| 14 | 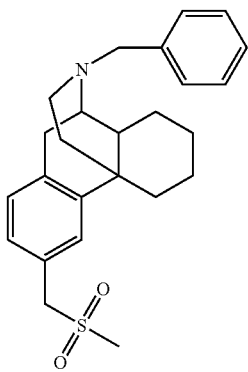<br>C₂₅H₃₁NO₂S<br>Mol. Wt.: 409.58 | δ6.73~7.49 (8H, m), 3.61~3.74 (2H, m), 3.08 (3H, s), 3.03 (1H, m), 2.88 (2H, m), 2.65 (1H, m), 2.30~2.48 (2H, m), 1.80 (2H, m), 1.73 (2H, m), 1.14~1.70 (6H, m) | 4 |
| 15 | 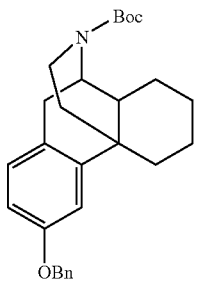<br>C₂₈H₃₅NO₃<br>Mol. Wt.: 433.58 | δ7.4614 7.34 (5H, m), 7.00(1H, m), 6.91 (1H, m), 6.80 (1H, m), 5.04 (2H, m), 4.37 (0.55H, br), 4.18 (0.45H, br), 3.73 (1H, m), 3.06 (1H, m), 2.65 (2H, m), 2.32 (m, m), 1.63-1.08 (19H, m) | |
| 16 | 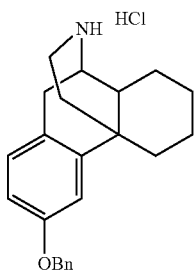<br>C₂₃H₂₈ClNO<br>Mol. Wt.: 369.93 | (MeOD) δ7.43-7.28 (5H, m), 7.12 (1H, br), 6.88 (2H, br), 5.04 (2H, m), 3.29 (2H, br), 2.90 (1H, br), 2.33 (2H, br), 1.67-1.10 (11H, m) | |
| 17 | 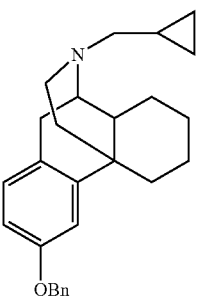<br>C₂₇H₃₃NO<br>Mol. Wt.: 387.56 | δ7.43-7.26 (5H, m), 6.99 (1H, m), 6.86 (1H, m), 6.75 (1H, m), 5.01 (2H, m), 3.07 (1H, br), 2.90 (1H, m), 2.67-2.45 (3H, m), 2.32-2.28 (2H, m), 1.98 (1H, m), 1.81-1.25 (10H, m), 0.86 (1H, br), 0.49 (2H, br), 0.09 (2H, br) | |

| | | |
|---|---|---|
| 18 | 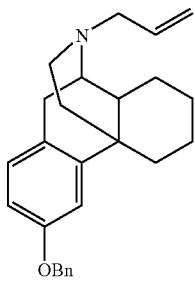<br>C₂₆H₃₁NO<br>Mol. Wt.: 373.53 | δ7.46-7.30 (5H, m), 7.05 (1H, m), 6.89 (1H, m), 6.80 (1H, m), 5.88 (1H, br), 5.24-5.15 (2H, m), 5.03 (2H, m), 3.19 (2H, br), 2.94 (2H, br), 2.59 (2H, m), 2.30 (1H, m), 2.04 (2H, br), 1.83-1.13 (9H, m) |
| 19 | 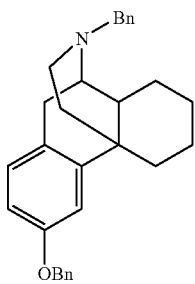<br>C₃₀H₃₃NO<br>Mol. Wt.: 423.59 | δ7.43-7.23 (10H, m), 6.87 (1H, m), 6.86 (1H, m), 6.77 (1H, m), 5.01 (2H, m), 3.73-3.58 (2H, m), 2.99 (1H, m), 2.83 (1H, br), 2.62-2.56 (1H, m), 2.43 (1H, m), 2.28 (1H, m), 2.12 (1H, m), 1.85-1.14 (10H, m) |
| 20 | 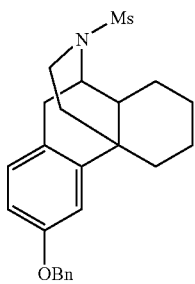<br>C₂₄H₂₉NO₃S<br>Mol. Wt.: 411.56 | δ7.44-7.25 (5H, m), 7.04 (1H, m), 6.89 (1H, m), 6.83 (1H, m), 5.05 (2H, m), 4.09 (1H, m), 3.70 (1H, m), 3.38-2.78 (6H, m), 2.28 (1H, m), 1.82-1.12 (10H, m) |
| 21 | 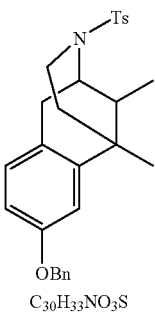<br>C₃₀H₃₃NO₃S<br>Mol. Wt.: 487.65 | δ7.71-7.68 (2H, m), 7.43-7.26 (7H, m), 6.84 (2H, m), 6.75 (1H, m), 5.00 (2H, m), 4.12 (1H, m), 3.59 (1H, m), 2.89 (1H, m), 2.67 (1H, m), 2.46 (4H, m), 2.26 (1H, m), 1.74-1.09 (10H, m) |

| | | |
|---|---|---|
| 22 | 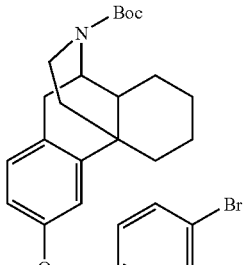<br>C₂₈H₃₄BrNO₃<br>Mol. Wt.: 512.48 | δ7.55-7.50 (2H, m), 7.36-7.25 (2H, m), 7.00 (1H, m), 6.87 (1H, m), 6.77 (1H, m), 5.00 (2H, m), 4.37 (0.59H, br), 4.18 (0.41H, br), 3.75-3.72 (1H, m), 3.06 (1H, m), 2.67-2.61 (2H, m), 2.30 (1H, m), 1.65-1.07 (19H, m) |
| 23 | 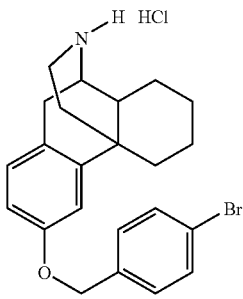<br>C₂₃H₂₇BrClNO<br>Mol. Wt.: 448.82 | (MeOD) δ7.57-7.51 (2H, m), 7.41-7.35 (2H, m), 7.17 (1H, m), 6.92 (2H, m), 5.07 (2H, m), 3.26-3.10 (2H, m), 2.95-2.81 (1H, m), 2.78 (1H, m), 2.36 (1H, m), 1.73-1.19 (11H, m) |
| 24 | 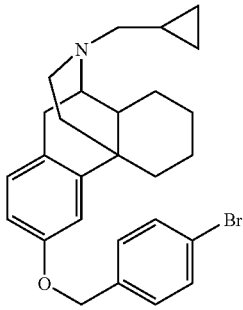<br>C₂₇H₃₂BrNO<br>Mol. Wt.: 466.45 | δ7.51-7.33 (2H, m), 7.30-7.26 (2H, m), 7.01 (1H, m), 6.84 (1H, m), 6.73 (1H, m), 4.98 (2H, m), 3.21 (1H, br), 2.95-2.85 (1H, m), 2.73-2.51 (3H, m), 2.32 (2H, m), 1.98-1.23 (11H, m), 0.75 (1H, br), 0.52 (2H, br), 0.12 (2H, br) |
| 25 | 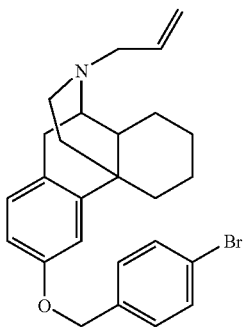<br>C₂₆H₃₀BrNO<br>Mol. Wt.: 452.43 | δ7.54-7.36 (2H, m), 7.31-7.25 (2H, m), 7.00 (1H, m), 6.82 (1H, m), 6.75 (1H, m), 5.79 (1H, br), 5.28-5.13 (2H, m), 5.01 (2H, m), 3.21 (2H, br), 2.90 (2H, br), 2.62 (2H, m), 2.27 (1H, m), 2.06 (2H, br), 1.85-1.21 (9H, m) |

| | | | |
|---|---|---|---|
| 26 | 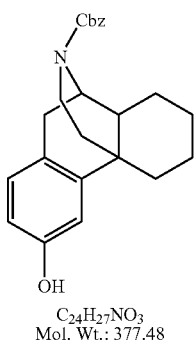<br>C₂₄H₂₇NO₃<br>Mol. Wt.: 377.48 | δ7.3~7.5(5H, m) 6.9(1H, t) 6.8(1H, d) 6.6(1H, t) 5.1(2H, s) 4.3(1H, dd) 3.9(1H, m) 3.1(1H, m) 2.7(2H, m) 2.3(1H, d) 1.0~1.8(10H, m) | 1 |
| 27 | 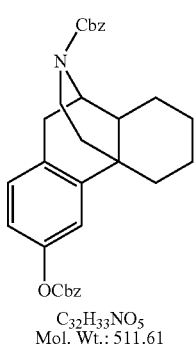<br>C₃₂H₃₃NO₅<br>Mol. Wt.: 511.61 | δ7.3~7.6(10H, m) 7.0(2H, m) 6.9(1H, m) 5.3(2H, s) 5.1(2H, s) 4.3(1H, dd) 3.9(1H, m) 3.1(1H, m) 2.7(2H, d) 2.3(1H, m) 1.0~1.8(10H, m) | 1 |
| 28 | 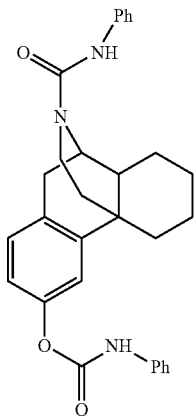<br>C₃₀H₃₁N₃O₃<br>Mol. Wt.: 481.59 | δ7.4(2H, d) 7.2(6H, m) 7.0(6H, m) 6.3(1H, s) 4.4(1H, s) 3.5(1H, d. d.) 3.1(1H, d. d.) 2.8(2H, m) 2.3(1H, m) 1.0~1.9(10H, m) | 1 |
| 29 | 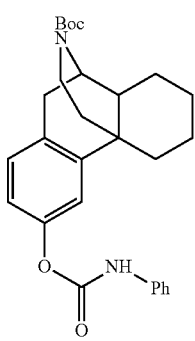<br>C₂₈H₃₄N₂O₄<br>Mol. Wt.: 462.58 | δ7.4(2H, d) 7.3(2H, t) 7.1(3H, m) 6.9(2H, m) 4.3(1H, m) 3.1(1H, d. d.) 2.4~2.8(2H, m) 2.3(1H, m) 1.3(9H, s) 1.8(1H, m) 1.0~1.7(10H, m) | 1 |

-continued
| 30 | 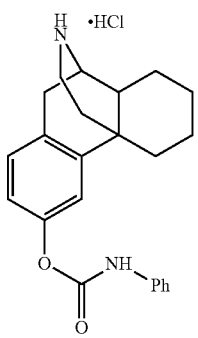<br>C₂₃H₂₇ClN₂O₂<br>Mol. Wt.: 398.93 | (MeOD) δ7.5(2H, d) 7.3(3H, m) 7.1(1H, d) 7.0(2H, m) 3.0~3.4(3H, m) 2.8(1H, m) 2.5(1H, m)  3.9(1H, m) 1.0~1.9(10H, m) | 1 |
| --- | --- | --- | --- |
| 31 | 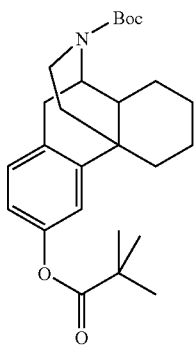<br>C₂₆H₃₇NO₄<br>Mol. Wt.: 427.58 | δ0.9~1.7 (m, 29 H), 2.34 (d, J = 9.9 Hz, 1 H), 2.5~2.73 (m, 2 H), 3.09~3.17 (m, 1 H), 3.73~3.84 (m, 1 H), 6.83~6.87 (m, 1 H), 6.95 (s, 1 H), 7.09~7.12 (m, 1 H) | |
| 32 | 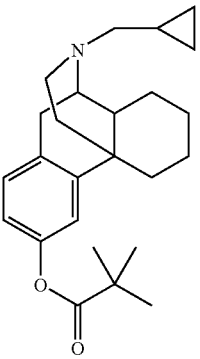<br>C₂₅H₃₅NO₂<br>Mol. Wt.: 381.55 | 0.43~1.58 (m, 24 H), 2.35~2.52 (m, 2 H), 2.69~2.73 (m, 1H), 2.90~2.96 (m, 2H), 3.16~3.35 (m, 2H), 3.91 (s, 1 H), 6.92~6.96 (m, 1H), 6.99 (s, 1H), 7.17 (d, J = 8.2 Hz, 1 H) | |
| 34 | 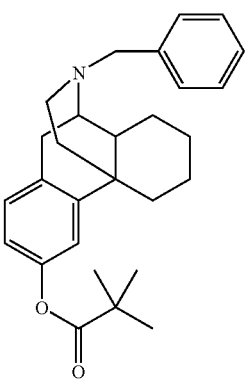<br>C₂₈H₃₅NO₂<br>Mol. Wt.: 417.58 | δ0.91~1.74 (m, 18 H), 1.89 (m, J = 12.6 Hz, 1 H), 2.07~2.21 (m, 1 H), 2.29~2.48 (m, 2H), 2.63~2.69 (m, 1 H), 2.87 (s, 1 H), 3.09 (d, J = 18.3 Hz, 1 H), 3.68 (dd, J = 13.4 Hz, 2H), 6.82~6.93 (m, 2H), 7.15 (d, J = 8.3 Hz, 1 H), 7.25~7.38 (m, 5 H) | |

-continued
| | | |
|---|---|---|
| 35 | 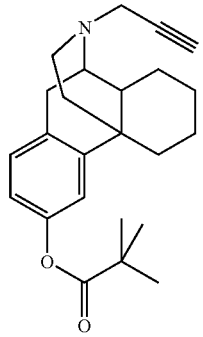<br>C₂₄H₃₁NO₂<br>Mol. Wt.: 365.51 | δ1.15~1.87 (m, 20 H), 2.14~2.31 (m, 2 H), 2.67~2.74 (m, 2H), 3.02 (d, J = 18.6 Hz, 1 H), 3.12~3.14 (m, 1 H), 3.36~3.39 (m, 2H), 6.81~6.93 (m, 2H), 7.16 (d, J = 8.2 Hz, 1 H) | |
| 36 | 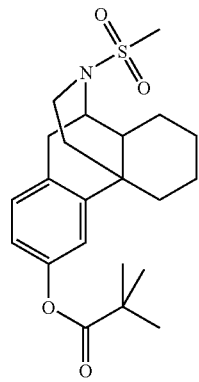<br>C₂₂H₃₁NO₄S<br>Mol. Wt.: 405.55 | δ1.08~1.87 (m, 20 H), 2.36 (d, J = 12.4 Hz, 1 H), 2.77~2.92 (m, 5 H), 3.51~3.54 (m, 1 H), 4.10~4.15 (m, 1H), 6.86~6.96 (m, 2H), 7.13 (d, J = 8.3 Hz, 1 H). | |
| 37 | 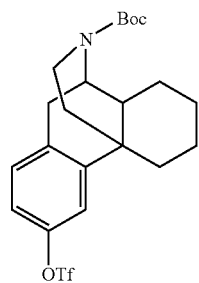<br>C₂₂H₂₈F₃NO₅S<br>Mol. Wt.: 475.52 | ¹H NMR (300 MHz, CDCl₃) δ7.03~7.38 (3H, m), 4.30 (1H, s), 3.85 (1H, dd), 3.13 (1H, d), 2.72 (1H, d), 2.50 (1H, m), 2.30 (1H, d), 1.43 (9H, s), 1.09~1.80 (10H, m) | 1 |
| 38 | 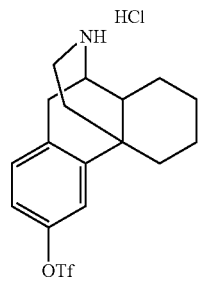<br>C₁₇H₂₁ClF₃NO₃S<br>Mol. Wt.: 411.87 | δ0.96~2.04 (m, 12 H), 2.27~3.18 (m, 4 H), 3.45 (s, 1 H), 7.07~7.15 (m, 2H), 7.22 (s, 1 H) | |

-continued
| | | |
|---|---|---|
| 39 | 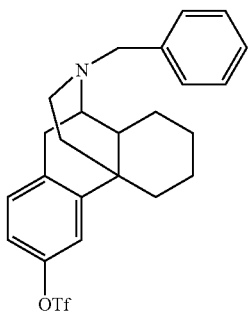<br>C$_{24}$H$_{26}$F$_3$NO$_3$S<br>Mol. Wt.: 465.53 | 1.05~1.72 (m, 9 H), 1.74~1.85 (m, 1 H), 1.90~1.94 (m, 1 H), 1.96~2.05 (m, 1 H), 2.31 (d, J = 13.0 Hz, 1 H), 2.48~2.52 (m, 1 H), 2.88~2.91 (m, 1 H), 3.12 (d, J = 18.6 Hz, 1 H), 3.67 (dd, J = 13.4 Hz, 2 H), 7.03~7.38 (m, 8H). |
| 40 | 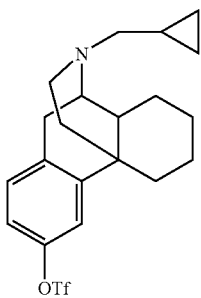<br>C$_{21}$H$_{26}$F$_3$NO$_3$S<br>Mol. Wt.: 429.50 | 0.19~2.10 (m, 17 H), 2.31 (d, J = 13.8 Hz, 1 H), 2.47~2.59 (m, 2 H), 2.78~2.88 (m, 2 H), 3.30 (s, 1 H), 7.02~7.06 (m, 1 H), 7.13~7.20 (m, 2 H). |
| 41 | 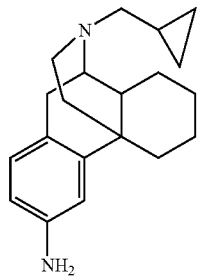<br>C$_{20}$H$_{28}$N$_2$<br>Mol. Wt.: 296.45 | 0.15~3.24 (m, 25 H), 6.62~6.65 (m, 1 H), 6.75 (d, J = 2.2 Hz, 1 H), 6.94 (d, J = 8.2 Hz, 1 H) |
| 42 | 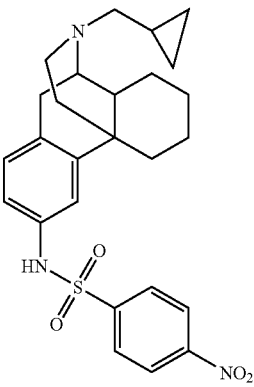<br>C$_{26}$H$_{31}$N$_3$O$_4$S<br>Mol. Wt.: 481.61 | 0.19~0.63 (m, 8 H), 0.96~2.11 (m, 13 H), 2.55~3.53 (m, 6 H), 6.83~6.87 (m, 2 H), 7.10 (d, J = 8.3 Hz, 1 H), 8.10 (d, J = 8.7 Hz, 2 H), 8.38 (d, J = 8.7 Hz, 2H) |

-continued
| | | |
|---|---|---|
| 43 | 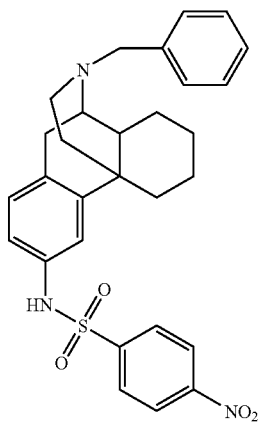<br>C$_{29}$H$_{31}$N$_3$O$_4$S<br>Mol. Wt.: 517.64 | 0.89~2.06 (m, 12 H), 2.46~2.701 (m, 2 H), 2.87 (s, 1 H), 3.06 (d, J = 18.6 Hz, 1 H), 3.54~4.10 (m, 2H), 6.76 (s, 1 H), 6.83~6.86 (m, 1 H), 7.12 (d, J = 8.4 Hz, 1 H), 8.04 (d, J = 8.8 Hz, 2 H) |
| 44 | 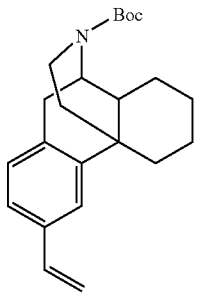<br>C$_{23}$H$_{31}$NO$_2$<br>Mol. Wt.: 353.50 | δ7.25~7.32(2H, m), 7.05(1H, 6), 6.62(1H, d.d.), 5.78(1H, d), 5.20(1H, d), 4.30(1H, m), 3.55~4.80(1H, m), 3.10(1H, m), 2.30~2.65(2H, m), 2.05(1H, m), 1.23(9H, s), 1.00~1.80(10H, m) |
| 45 | 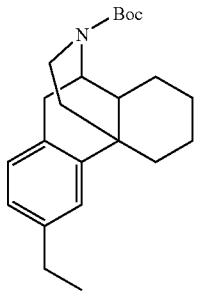<br>C$_{23}$H$_{33}$NO$_2$<br>Mol. Wt.: 355.51 | δ7.06~7.36 (3H, m), 4.37 (0.5H, s), 4.19 (0.5H, s), 3.88 (1H, dd), 3.11 (1H, m), 2.63 (2H, m), 2.59 (2H, m), 2.44 (1H, m), 1.60~1.80 (4H, m), 1.40~1.60(9H, d), 0.90~1.40 (9H, m) |
| 46 | 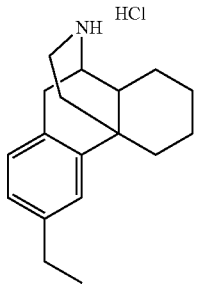<br>C$_{18}$H$_{26}$ClN<br>Mol. Wt.: 291.86 | (MeOD) δ7.13~7.46 (3H, m), 3.27 (2H, m), 3.19 (2H, s), 2.88 (1H, m), 2.81 (1H, m), 2.58 (2H, m), 1.10~1.80 (13H, m) |

| | | |
|---|---|---|
| 47 | 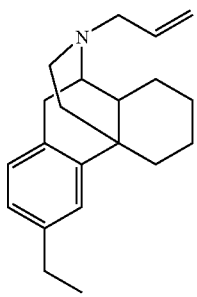<br>C₂₁H₂₉N<br>Mol. Wt.: 295.46 | δ6.89~7.16 (3H, m), 5.80 (1H, d), 5.16~5.30 (2H, m), 4.00~4.30 (1H, dd), 3.68 (2H, t), 3.66 (1H, m), 3.15 (1H, br), 2.68 (2H, m), 2.50 (2H, m), 2.38 (1H, m), 1.10~1.70 (13H, m) |
| 48 | 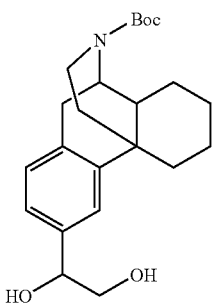<br>C₂₃H₃₃NO₄<br>Mol. Wt.: 387.51 | δ7.29~7.36(1H, m), 7.17~7.10(2H, m), 4.79(1H, d), 4.37(0.55H, br), 4.19(0.45H, br), 3.77~3.66(3H, m), 3.11(1H, m), 2.72~2.41(4H, m), 2.03(1H, m), 1.71~1.04(19H, m) |
| 49 | 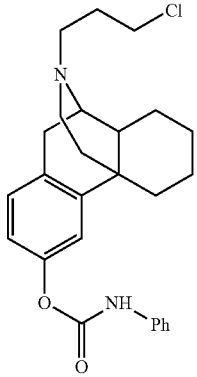<br>C₂₆H₃₁ClN₂O₂<br>Mol. Wt.: 438.99 | δ7.35(4H, m), 7.10(2H, m), 6.85(1H, d), 6.75(1H, d.d.), 6.28(1H, s), 4.38(1H, m), 4.10(2H, t), 3.80(2H, t), 3.65(1H, m), 3.14(1H, d.d.), 2.83(2H, m), 2.37(1H, m), 2.25(2H, m), 1.00~1.80(10H, m) |
| 50 | 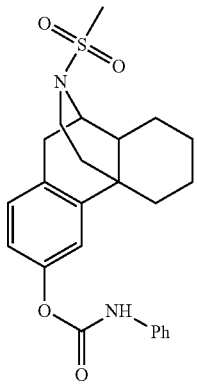<br>C₂₄H₂₈N₂O₄S<br>Mol. Wt.: 440.56 | δ7.48(2H, d), 7.31(2H, t), 7.15(3H, m), 7.04(1H, m), 6.90(1H, s), 4.11(1H, m), 3.55(1H, m), 3.18(1H, m), 2.93(3H, s), 2.84(2H, m), 2.30(1H, d), 1.00~1.80(10H, m) |

| | | |
|---|---|---|
| 51 | 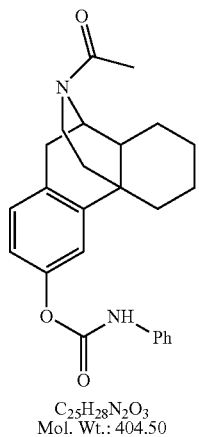<br>C$_{25}$H$_{28}$N$_2$O$_3$<br>Mol. Wt.: 404.50 | δ7.45(2H, d), 7.30(2H, t), 7.15(3H, m), 7.03(2H, m), 4.95(1H, m), 3.55(1H, m), 3.15(1H, m), 2.90(1H, m), 2.75(1H, m), 2.30(1H, m), 2.05(3H, s), 1.00~1.80(10H, m) |
| 52 | 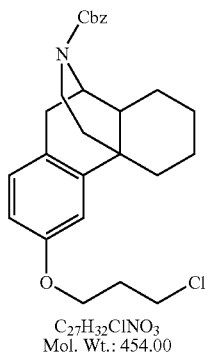<br>C$_{27}$H$_{32}$ClNO$_3$<br>Mol. Wt.: 454.00 | δ7.30(5H, m), 7.00(1H, 1), 6.83(1H, d), 6.70(1H, d. d.), 5.10(2H, m), 4.30(1H, m), 4.05(2H, 1), 3.90(1H, m), 3.79(2H, t), 3.05(1H, m), 2.75(2H, m), 2.30(1H, m), 2.15(2H, m), 1.00~1.80(10H, m) |
| 53 | 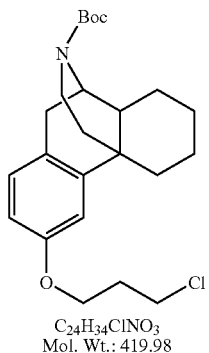<br>C$_{24}$H$_{34}$ClNO$_3$<br>Mol. Wt.: 419.98 | δ7.05(1H, m), 6.83(1H, d), 6.75(1H, d.d.), 4.28(1H, d), 4.05(2H, t), 3.90(1H, m), 3.83(3H, t), 3.15(1H, m), 2.60(2H, m), 2.30(1H, m), 2.15(1H, m), 1.30(9H, s), 1.00~1.80(10H, m) |
| 54 | 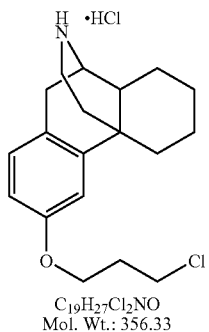<br>C$_{19}$H$_{27}$Cl$_2$NO<br>Mol. Wt.: 356.33 | (MeOD) δ7.15(1H, d), 6.80~7.10(2H, m), 4.05(2H, t), 3.78(2H, t), 3.65(2H, m), 3.30(1H, m), 3.10(2H, m), 2.78(1H, m), 2.45(1H, m), 2.18(2H, m), 1.00~2.00(10H, m) |

-continued

| | | |
|---|---|---|
| 55 | 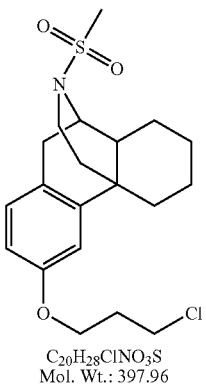<br>$C_{20}H_{28}ClNO_3S$<br>Mol. Wt.: 397.96 | δ 7.01(1H, m), 6.85(1H, d), 6.70(1H, d.d), 4.05(3H, m),<br>3.78(2H, t), 3.56(1H, d.d.), 3.15(1H, d.d.), 2.90(3H, s),<br>2.83(2H, m), 2.32(1H, m), 2.20(2H, m), 1.00~1.90(10H, m) |
| 56 | 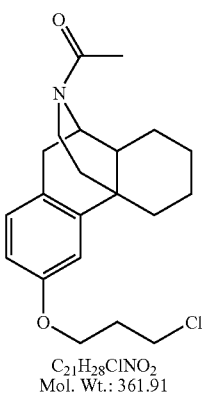<br>$C_{21}H_{28}ClNO_2$<br>Mol. Wt.: 361.91 | δ 6.96(1H, t), 6.83(1H, d), 6.75(1H, d. d.), 4.92(1H, m),<br>4.15(2H, t), 3.81(2H, t), 3.75(1H, m), 3.12(1H, m), 2.95(1H,<br>m), 2.62(1H, m), 2.30(1H, m), 2.18(2H, m), 2.05(3H, s),<br>1.00~1.80(10H, m) |
| 57 | 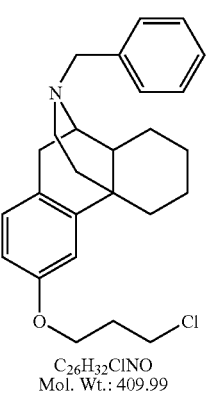<br>$C_{26}H_{32}ClNO$<br>Mol. Wt.: 409.99 | δ 7.15~7.35(5H, m), 7.05(1H, d), 6.80(1H, s), 6.73(1H, d),<br>4.10(2H, t), 3.55~3.85(4H, m), 3.05(1H, m), 2.80(1H, m),<br>2.56(1H, m), 2.40(1H, m), 2.00~2.30(4H, m), 1.00~1.90(10H,<br>m) |

Morphinan and Parkinson's Disease

Accumulating evidence suggests that dextromethorphan (DM) exhibits antiparkinsonian effects in vivo and in vitro. However, it is well-known that DM-induced psychotropic effects might hamper its clinical application. Dextrorotatory morphinans 3-hydroxymorphinan (HM), 3-allyloxy-17-methylmorphinan (AM), 3-cyclopropylmethoxy-17-methyl-morphinan (CM) and dimemorfan (DF) were previously synthesized (Bioorg Med Chem Lett 2001; 11:1651-1654, Behav. Brain Res. 2004; 151: 267-276, Br. J. Pharmacol. 2005; 144: 908-918). They showed negligible behavioural side effects as seen in DM or its major metabolite dextrorphan (DX). The present invention is directed to using dextrorotatory morphinans in treating or treating the symptoms of Parkinson's disease. DM, HM, and CM attenuated hypokinesia, reductions in the striatal levels of the dopamine and its metabolites, and in the nigral tyrosine hydroxykinase-like immunoreactivity (TH-IR) induced by 1-methyl-4-phenyl-1,2,5,6-tetrahydropyridine (MPTP), lipopolysacharide (LPS) or methamphetamine (MA). Although AM and DF did not significantly affect these toxicities induced by MPTP or LPS, they attenuated neurotoxicities (hyperthermia, hypokinesia, reductions in the striatal levels of the dopamine and its metabolites, and in the nigral TH-IR) induced by MA.

The behavioral and antiparkinsonian effects of dextrorotatory morphinans in mice were examined. As a parameter of behavioral side effect, PCP-induced behavioral profiles were examined, which are typically characterized by circling behaviors and conditioned place preference (CPP) (13, 27, 37). Interestingly, the marginal locomotor patterns (circling behaviors) were similar to those of CPP as previously demonstrated (13, 27). The action of DX was qualitatively similar to that of PCP, which is in line with previous investigations (24, 27). Although the DM-induced behavioral characteristics appeared to be less pronounced than those of DX, its psychotropic effects were observed in a dose-related manner. More significantly, AM, CM, HM, and DF which are modified in positions 3 (and 17) of the morphinan ring system, retained neurological activities but had weak behavioral side effects (7, 24, 27, 46). Previous demonstrations indicated that the mechanism of anticonvulsant/neuroprotective action of AM, CM or DF might be mediated via G, receptors rather than PCP sites (7, 24, 27, 46). The very low affinity of AM, CM or DF to PCP sites also provides evidence that acting on PCP sites might not be a prerequisite for the anticonvulsant/neuroprotective effects of morphinans. Although DM, AM, CM and DF exhibited anticonvulsant effects, HM did not show any anticonvulsant effect in response to kainate (24) or maximal electric shock (27), suggesting that pharmacological action of HM may be specific to the dopaminergic system. DM is rapidly metabolized by O-demethylation to a PCP-like compound, DX (50, 51, 54). DX then undergoes N-demethylation yielding HM. Both DX and HM are eliminated after glucuronidation. Alternatively, DM is metabolized first by N-demethylation yielding 3-methoxymorphinan, which then undergoes an O-demethylation reaction to yield HM (54). These metabolic processes may be helpful in attenuating dopaminergic toxicity, although more evidence should be gathered. It was assumed that 3-methoxymorphinan and HM have lower CNS activity as compared with DM or DX, but the route-specific effects of morphinan administration, influence of morphinan dosage, and in vivo glucuronidation capacity should be considered (54).

Although DM and DX have many actions in common, they differ in their receptor binding characteristics and in vivo pharmacology (7, 27, 34, 50). DM exhibits a high binding potency for distinct DM recognition sites and σ-receptor binding sites, but has a relatively low affinity for sites labeled by DX. In contrast, DX exhibits a high affinity for DX and PCP binding sites in the brain, while exhibiting a low to moderate affinity for DM and σ sites (50). Therefore, DM doses higher than the recommended antitussive dose should produce PCP-like effects related to DX (1, 2). In addition, DM might have the properties of a mixed agonist (17, 19, 20, 50, 51), which acts as a noncompetitive NMDA receptor antagonist at a low dose, but as a partial agonist at higher doses (20, 48, 49). Therefore, DM might interact with the PCP-NMDA-σ receptor complex (20, 48, 49, 50).

To reduce the PCP-like behavioral side effects (24, 39), while retaining the neuroprotective effects, a series of 3- and 17-substituted morphinans that are structurally similar to DM were prepared, but were either not expected to be metabolized into DX or were expected to do so at a reduced rate compared to DM. The size effect and rate of hydrolysis of ether were considered (24).

In Parkinson's disease, dopaminergic denervation of the striatum is the main biochemical lesion which accounts largely for clinical symptoms such as akinesia, hypotonia, tremor and postural instability (35). Despite several attempts to develop new dopaminergic drugs, especially dopamine agonists, levodopa remains the "gold standard" in the treatment of Parkinson's disease (35). However, its long-term use is associated with several side-effects, such as abnormal movements, fluctuations in performance, hallucinations and psychosis (35, 36). Thus, from a therapeutic point of view, new strategies based on new pathophysiological approaches are needed. Hence, drugs which act on symptoms that are resistant to levodopa, or which are neuroprotective, would be extremely valuable.

It has been suggested that low-affinity NMDA open channel antagonists may be good candidates for antiparkinsonian drugs. DM has a complex pharmacological profile that includes a micromolar affinity for the NMDA receptor channel. In two open-label clinical trials, DM was found to afford significant improvement in small cohorts of parkinsonian volunteers. Further, a modest recovery of activity in reserpinized mice following injection of DM and ketamine was seen, but these were subject to considerable inter-animal variation (47).

A major objection to administering NMDA receptor antagonists to man is that they can cause unacceptable side effects. These include psychostimulation and memory impairment, as well as muscle relaxation and ataxia. From theoretical considerations, however, compounds which have a low affinity for the NMDA receptor-associated ion channel may be the most effective and the least toxic of the many NMDA receptor antagonists that are available (32). Among the NMDA receptor antagonists, DM appears to come close to approximately matching this theoretical ideal and has been tested in small groups of idiopathic parkinsonian patients with mixed success (47).

Earlier reports have indicated that NMDA receptor blockade can directly restore motility to Parkinson-like mice (4) and rats (30), but not primates (6). However, not all laboratories find this and the matter is subject to some controversy (14).

In contrast, dextromethorphan analogs such as HM, AM, CM and DF disclosed in the present application, had very low affinities for NMDA receptor associated PCP sites (7, 27), suggesting that NMDA associated PCP sites are not prerequisites for their antiparkinsonian actions. In addition, previous reports have indicated that DM, DX, HM, AM, CM and DF are high affinity ligands for $\sigma_1$ receptors (7, 27, 46). Further, it is recognized that $\sigma_1$ receptors regulate glutamate NMDA receptor function and release of dopamine (11). Selective $\sigma_1$ receptor ligands have been suggested to present a new class of therapeutic agents for neurodegenerative diseases, although none have yet been introduced into therapeutic use (11). Recently, it was demonstrated that $\sigma_1$ receptor agonists inhibit NMDA-stimulated [$^3$H]dopamine release from slices of rat and guinea pig striatum, prefrontal cortex and nucleus accumbens (2). In addition, G, receptor plays an important role in the facilitation of dopamine transmission (31,42). This phenomenon is partially involved in the augmentation of dopamine synthesis rate. Without being bound by theory, although morphinans' contribution via NMDA receptor antagonism cannot be excluded, the primary mechanism of action of morphinans is, at least in part, related to $\sigma_1$ receptor modulation.

Combined, the results of this study indicate that DM has prominent antiparkinsonian effects in the MPTP, LPS, and MA models, although DM exhibits behavioral side effects. More importantly, the other morphinans do not produce the PCP-like behavioral side effects of DM or DX. Moreover, HM and CM have significant antiparkinsonian effects in response to MPTP, LPS and MA. AM and DF are effective against MA-induced neurotoxicity. MA-induced dopaminergic toxicity has long been considered to be one of the most important animal models of Parkinson's disease.

Therapeutic Formulations

Administration of the morphinan and their mixtures and/or pharmaceutically acceptable salts can be orally or transdermally or by intravenous, intramuscular, subcutaneous, intrathecal, epidural or intracerebro-ventricular injection. Effective dosage levels can vary widely, e.g., from about 0.25 to about 250 mg/day, but actual amounts will, of course, depend on the state and circumstances of the patient being treated. As those skilled in the art recognize, many factors that modify the action of the active substance herein will be taken into account by the treating physician such as the age, body weight, sex, diet and condition of the patient, the time of administration, the rate and route of administration, and so forth. Optimal dosages for a given set of conditions can be ascertained by those skilled in the art using conventional dosage determination tests in view of the experimental data provided herein.

Therapeutic compositions containing the morphinans, their mixtures and/or pharmaceutically acceptable salts will ordinarily be formulated with one or more pharmaceutically acceptable ingredients in accordance with known and established practice. Thus, the morphinans, their mixtures and/or pharmaceutically acceptable salts can be formulated as a liquid, powder, elixir, injectable solution, etc. Formulations for oral use can be provided as hard gelatin capsules wherein the morphinans, their mixtures and/or pharmaceutically acceptable salts are mixed with an inert solid diluent such as calcium carbonate, calcium phosphate or kaolin, or as soft gelatin capsules wherein the morphinans, their mixtures and/or pharmaceutically acceptable salts are mixed with an oleaginous medium, e.g., liquid paraffin or olive oil.

Aqueous suspensions can contain the morphinans, their mixtures and/or pharmaceutically acceptable salts in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or -n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide the morphinans, their mixtures and/or pharmaceutically acceptable salts in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

The morphinans, their mixtures and/or pharmaceutically acceptable salts are advantageously provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

It is also within the scope of this invention to administer the morphinans, their mixtures and/or pharmaceutically acceptable salts prior to, concurrently with, or after administration of any other known pharmacologically active agent useful for treating or treating the symptoms of Parkinson's disease. Such pharmacologically active agents may include without limitation other neuroprotective agents.

Neuroprotective agents attempt to save ischemic neurons in the brain from irreversible injury. Other neuroprotective agents prevent potentially detrimental events associated with return of blood flow. Although return of blood flow to the brain is generally associated with improved outcome, reperfusion may contribute to additional brain injury. Returning blood contains leukocytes that may occlude small vessels and release toxic products. Ischemia leads to excessive activation of excitatory amino acid receptors, accumulation of intracellular calcium, and release of other toxic products that cause cellular injury. By preventing excitatory neurotransmitter release, neuroprotective agents may reduce deleterious effects of ischemia on cells.

The most commonly studied neuroprotective agents block the N-methyl-D-aspartate (NMDA) receptor. Modulating other non-NMDA receptors and channels also can reduce excitatory neurotransmitter release. Antiadhesion antibodies such as monoclonal antibodies that can block an intercellular adhesion molecule (ICAM) on the endothelium may be used to prevent adhesion of white blood cells to the vessel wall. Because anti-ICAM antibodies appear to block an early step in reperfusion-related injury, they present a hopeful mechanism for preserving neuronal function. Other neuroprotective agents induce membrane stabilization. For example, an exogenous form of CDP-choline is used in membrane biosynthesis and decreases free radical formation. Neuronal healing agents such as basic fibroblast growth factor may also be used.

Instructions

The present invention is also directed to instructions regarding the use the inventive morphinans for treating a variety of neurological conditions, including Parkinson's disease or the symptoms of Parkinson's disease, learning and memory impairment in Alzheimer's disease, the symptoms of intoxication and or dependence on such narcotics as cocaine, morphine, and methamphetamine. Such instructions may be in a permanent or temporary format. The instructions may be in written form, such as but not limited to a textbook, protocol book, catalog, internet web site and so on. Such instructions may be in relation to but not limited to the sale and use of the morphinans. The instructions may be presented via a computer screen on a cathode ray tube, LCD, LED, and so on, so long as the instructions are visible through the eye. The instructions may also be in the form of audio/visual media, or as part of a kit for treating the various symptoms as indicated above.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Preparative Examples

Preparative Example 1.1

Preparation of 3-hydroxy-N-(tert-butyloxycarbonyl)morphinan 2 and 3-O-(tert-butyloxycarbonyl)-N-(tert-butyloxycarbonyl)morphinan 3

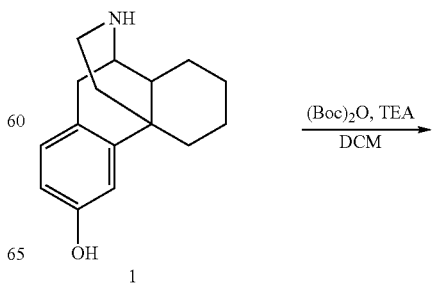

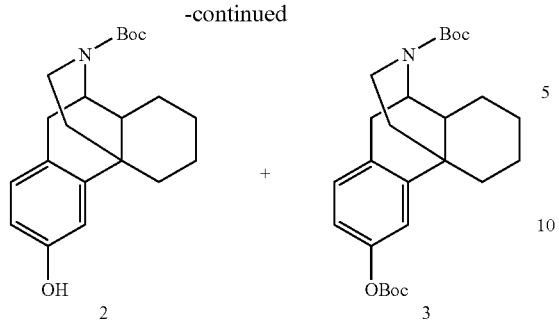

To a solution of 3-hydroxy-N-(tert-butyloxycarbonyl)morphinan (200 mg, 0.62 mmol) in dry dichloromethane (3.0 mL) were added triethylamine (250 µL, 1.83 mmol) and Boc$_2$O (190 mg, 0.88 mmol) sequentially and the mixture was stirred at room temperature. After 2 h, solvent was removed under reduced pressure and the residue was purified by silica gel column chromatography to yield Compound 2 (168 mg, 79%) and compound 3 (43 m, 16%): $^1$H NMR (300 MHz, CDCl$_3$) δ7.04~7.08 (3H, m); 3.73 (2H, m); 3.68 (1H, m); 3.08 (2H, m); 2.15 (1H, m); 1.83 (2H, m); 1.50~1.70 (8H, m); 1.40 (9H, s) (for 2), δ7.05~6.83 (3H, m); 4.30 (0.50H, br) 4.00 (0.50H, br); 3.85 (0.50H, m); 3.68 (0.50H, m); 3.05~3.25 (1H, m); 2.50~2.70 (2H, m); 1.65~1.80 (5H, br); 1.57 (9H, s); 1.49 (9H, s); 1.15-1.30 (6H, m) (for 3).

Preparative Example 1.2

Preparation of 3-O-propargyl-N-(tert-butyloxylcarbonyl)morphinan 4

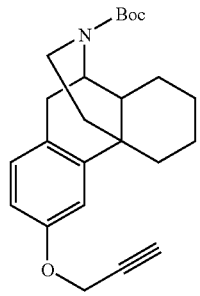

4

To a solution of compound 2 (22 mg, 0.064 mmol) in dry DMF (2.0 mL) were added potassium carbonate (40 mg, 0.29 mmol) and propargyl bromide (34 µL, 0.384 mmol) sequentially and the mixture refluxed at 60° C. After 18 h, to the mixture was added sat aq NaCl solution (2 mL) and the mixture was extracted with EtOAc (3 mL×3). Combined organic layer was dried over anhydrous MgSO$_4$, filtered, and concentrated. Silica gel column chromatography of the crude product gave 20 mg (82%) of a white solid: $^1$H NMR (300 MHz, CDCl$_3$) δ7.04~6.89 (3H, m); 4.70 (2H, s); 4.33 (0.5H, br); 4.18 (0.5H, m); 3.90 (0.5H, d); 3.73 (0.5H, d); 3.15~3.07 (1H, m); 2.59 (1H, s); 2.30 (1H, br); 1.83 (2H, m); 1.60 (2H, m); 1.44~1.47 (9H, s); 1.15~1.30 (8H, m).

Preparative Example 1.3

Preparation of 3-(2-propynyl)oxymorphinan.HCl 5

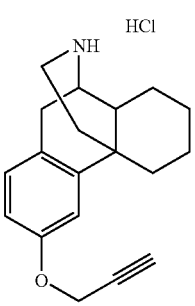

5

To a solution of compound 4 (22 mg, 0.052 mmol) in dry DCM (1 mL) was added 4 N HCl in 1,4-dioxane solution (160 µL) and the mixture stirred for 6 h at room temperature. After starting material disappeared on TLC, solvent was evaporated. And 18 mg (96%) of white solid was obtained: $^1$H NMR (300 MHz, CD$_3$OD) δ7.04~6.89 (3H, m); 4.75 (2H, s); 4.33 (0.5H, br); 4.18 (0.5H, m); 3.90 (0.5H, d); 3.73 (0.5H, d); 3.15~3.07 (1H, m); 2.59 (1H, s); 2.30 (1H, br); 1.83 (2H, m); 1.60 (2H, m); 1.15~1.30 (8H, m).

Preparative Example 1.3

Preparation of 3-(2-propynyl)oxy-N-(1-cyclopropyl)methylmorphinan 6

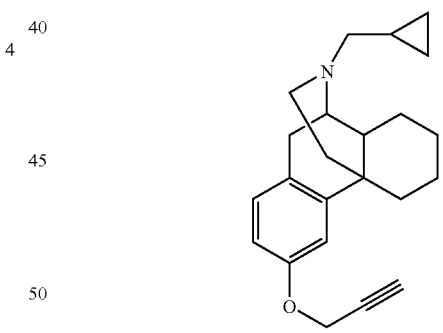

6

To a solution of compound 5 (6 mg, 0.017 mmol) in dry DMF (0.5 mL) were added potassium carbonate (6.6 mg, 0.048 mmol) and cyclopropylmethyl bromide (4.0 µL, 0.04 mmol) sequentially and the mixture was refluxed at 60° C. After 6 h, to the mixture was added sat aq NaCl solution (2 mL) and organic material was extracted with DCM (3 mL×2). Combined organic layer was dried over anhydrous MgSO$_4$, filtered, and concentrated. Column chromatography of the crude product gave 4.5 mg (79%) of a white solid: $^1$H NMR (300 MHz, CDCl$_3$) δ7.00~6.76 (3H, m); 4.70 (2H, s); 3.18 (2H, br); 2.75 (2H, m); 2.68 (1H, m); 2.48 (1H, d); 2.35 (2H, m); 1.56 (2H, m); 1.53 (1H, br); 1.44 (2H, m); 1.25~1.40 (6H, m); 0.95 (1H, m); 0.58 (2H, s); 0.25 (2H, m).

Preparative Example 1.4

Preparation of 3-(2-propynyl)oxy-N-allylmorphinan 7

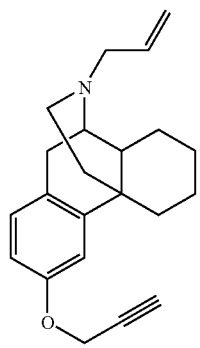

To a solution of compound 5 (6 mg, 0.017 mmol) in dry DMF (0.5 mL) were added potassium carbonate (6.6 mg, 0.048 mmol) and allyl bromide (3.1 μL, 0.036 mmol) sequentially and the mixture was refluxed at room temperature. After 2 h, to the mixture was added sat aq NaCl solution (2 mL) and the mixture was extracted with DCM (2 mL×2). Combined organic layer was dried over anhydrous MgSO$_4$, filtered, and concentrated. Column chromatography of the crude product gave 5.1 mg (91%) of a white solid: $^1$H NMR (300 MHz, CDCl$_3$) δ6.73~7.09 (3H, m); 5.90 (1H, m); 5.14~5.20 (2H, m); 4.64 (2H, m); 3.17 (2H, m); 2.94 (2H, m); 2.85 (1H, m); 2.55 (1H, d); 2.53 (2H, m); 2.00 (2H, t); 1.63 (2H, br); 1.20~1.48 (6H, m).

Preparative Example 1.5

Preparation of 3-(2-propynyl)oxy-N-benzylmorphinan 8

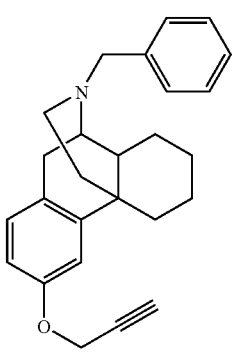

To a solution of compound 5 (6 mg, 0.016 mmol) in dry DMF (0.50 mL) were added potassium carbonate (6.6 mg, 0.048 mmol) and benzyl bromide (5.8 μL, 0.048 mmol) sequentially and the mixture was refluxed at 60° C. After 3 h, to the mixture was added sat aq NaCl solution (2 mL) and the mixture was extracted with EtOAc (3 mL×3). Combined organic layer was dried over anhydrous MgSO$_4$, filtered, and concentrated. Column chromatography of the crude product gave 5.0 mg (84%) of a white solid: $^1$H NMR (300 MHz, CDCl$_3$) δ6.73~7.49 (8H, m); 5.30 (2H, s); 3.68 (2H, br); 3.05 (2H, m); 2.83 (1H, br); 2.55 (1H, br); 2.35 (1H, m); 2.23 (1H, m); 1.80 (1H, m); 1.13~1.60 (10H, m).

Preparative Example 1.6

Preparation of 3-methanesulfonyloxy-N-(tert-butyloxylcarbonyl)morphinan 9

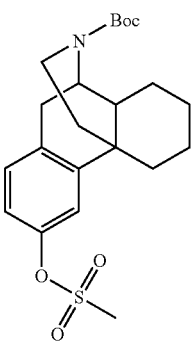

To a solution of compound 2 (26 mg, 0.076 mmol) in dry DCM (3.0 mL) were added triethylamine (32 μL, 0.23 mmol) and methanesulfonyl chloride (7.6 μL, 0.098 mmol). And the mixture was refluxed at 60° C. After 30 min, the mixture was dried over anhydrous MgSO$_4$, filtered, and concentrated. Column chromatography of the crude product gave 30 mg (94%) of a white solid: $^1$H NMR (300 MHz, CDCl$_3$) δ7.04~6.89 (3H, m); 4.33 (0.5H, br); 4.18 (0.5H, m); 3.90 (0.5H, d); 3.73 (0.5H, d); 3.20 (3H, s); 3.15~3.07 (1H, m); 2.60 (1H, m); 2.55 (1H, m); 2.30 (1H, m); 1.73 (2H, m); 1.60 (2H, br); 1.44~1.47 (9H, s); 1.15~1.30 (8H, m).

Preparative Example 1.7

Preparation of 3-methanesulfonyloxy-morphinan.HCl 10

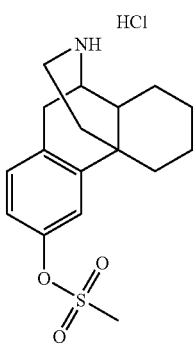

To a solution of compound 9 (27 mg, 0.019 mmol) in dry DCM (1 mL) was added 4 N HCl in 1,4-dioxane solution (200 μL) and the mixture stirred for 12 h at room temperature. After starting material disappeared on TLC, solvent was evaporated and 25 mg (96%) of white solid was obtained.

Preparative Example 1.8

Preparation of 3-methanesulfonyloxy-N-(methanesulfonyl)morphinan 11

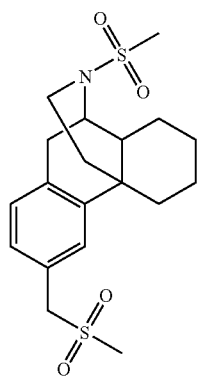

11

To a solution of compound 10 (7 mg, 0.020 mmol) in dry DCM (1.0 mL) were added triethylamine (32 μL, 0.23 mmol) and methanesulfonyl chloride (7.6 μL, 0.098 mmol). The mixture was refluxed at 60° C. After 2 h, it was dried over anhydrous MgSO$_4$, filtered, and concentrated. Column chromatography of the crude product gave 7.5 mg (94%) of a white solid: $^1$H NMR (300 MHz, CDCl$_3$) δ7.2~6.90 (3H, m); 4.03 (1H, br); 3.68 (1H, m); 3.30 (2H, m); 3.23 (3H, s); 2.82 (3H, m); 2.75 (3H, s); 2.60 (1H, m); 2.35 (1H, m); 1.68~1.80 (4H, m); 1.25~1.60 (6H, m); 1.15~1.20 (2H, m).

Preparative Example 1.9

Preparation of 3-methanesulfonyloxy-N-allylmorphinan 12

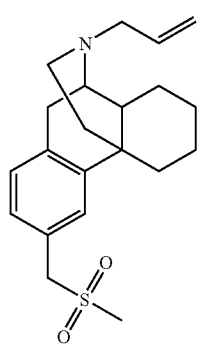

12

To a solution of compound 10 (7 mg, 0.020 mmol) in dry DMF (0.5 mL) were added potassium carbonate (6.6 mg, 0.048 mmol) and allyl bromide (3.0 μL, 0.036 mmol) sequentially and the mixture was refluxed at room temperature. After 6 h, to the mixture was added sat aq NaCl solution (2 mL) and the mixture was extracted with DCM (2 mL×4). Combined organic layer was dried over anhydrous MgSO$_4$, filtered, and concentrated. Column chromatography of the crude product gave 5.0 mg (70%) of a white solid: $^1$H NMR (300 MHz, CDCl$_3$) δ6.85~7.19 (3H, m); 5.90 (1H, br); 5.14~5.20 (2H, m); 3.14 (2H, m); 3.07 (3H, s); 2.80 (2H, m); 2.40 (2H, m); 2.35 (1H, d); 1.60~1.90 (4H, m); 1.20~1.48 (8H, m).

Preparative Example 1.10

Preparation of 3-methanesulfonyloxy-N-allylmorphinan 13

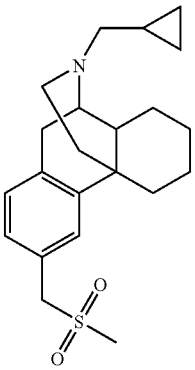

13

To a solution of compound 10 (7 mg, 0.020 mmol) in dry DMF (0.5 mL) were added potassium carbonate (6.6 mg, 0.048 mmol) and cyclopropylmethyl bromide (4.0 μL, 0.04 mmol) sequentially and the mixture was refluxed at 60° C. After 6 h, to the mixture was added sat aq NaCl solution (2 mL) and the mixture was extracted with DCM (3 mL×2). The combined organic layer was dried over anhydrous MgSO$_4$, filtered, and concentrated. Column chromatography of the crude product gave 5.5 mg (78%) of a white solid: $^1$H NMR (300 MHz, CDCl$_3$) δ6.85~7.19 (3H, m); 3.07 (3H, s); 2.80 (2H, m); 2.40~2.60 (2H, m); 2.20 (2H, m); 2.10 (2H, s); 1.700 (2H, br); 1.20~1.48 (8H, m); 0.80 (2H, m); 0.40 (2H, m).

Preparative Example 1.11

Preparation of 3-methanesulfonyloxy-N-benzylmorphinan 14

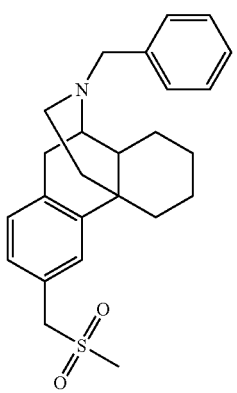

14

To a solution of compound 5 (7 mg, 0.020 mmol) in dry DMF (0.50 mL) were added potassium carbonate (6.6 mg, 0.048 mmol) and benzyl bromide (5.8 μL, 0.048 mmol) sequentially and the mixture was refluxed at 60° C. After 12 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 5.9 mg (74%) of a white solid: $^1$H NMR (300 MHz, CDCl$_3$) δ6.73~7.49 (8H, m); 3.68 (2H, m); 3.05 (3H, s); 2.88 (2H, m); 2.65 (1H, m); 2.30 (1H, m); 2.13 (1H, m); 2.00 (2H, m); 1.80 (1H, m); 1.73 (2H, m); 1.40~1.70 (6H, m); 1.15~1.33 (2H, m).

Preparative Example 1.12

Preparation of
3-benzyloxy-N-(tert-butyloxycarbonyl)morphinan 15

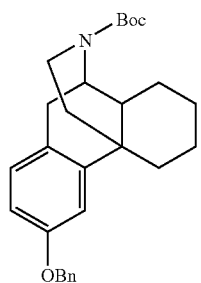

15

To a solution of 3-hydroxy-N-(tert-butyloxycarbonyl)morphinan (20 mg, 0.058 mmol) in dry DMF (0.3 mL) were added potassium carbonate (17 mg, 0.12 mmol) and benzyl bromide (10 μL, 0.087 mmol) sequentially and the mixture refluxed at 60° C. After 5 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 22 mg (88%) of a white solid: $^1$H NMR (300 MHz, CDCl$_3$) δ 7.46-7.34 (5H, m); 7.00 (1H, m); 6.91 (1H, m); 6.80 (1H, m); 5.04 (2H, m); 4.37 (0.55H, br); 4.18 (0.45H, br); 3.73 (1H, m); 3.06 (1H, m); 2.65 (2H, m); 2.32 (1H, m); 1.63-1.08 (19H, m).

Preparative Example 1.13

Preparation of 3-benzyloxymorphinan.HCl 16

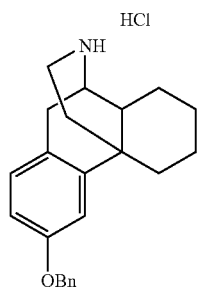

16

To a solution of compound 15 (22 mg, 0.051 mmol) in dry THF (70 μL) was added 4 N HCl in 1,4-dioxane solution (110 μL) and the mixture stirred for 2 h at room temperature. After starting material disappeared on TLC, solvent was evaporated. Simple trituration of the crude product gave 18 mg (97%) of a white solid: $^1$H NMR (300 MHz, CDCl$_3$) δ 7.43-7.28 (5H, m); 7.12 (1H, br); 6.88 (2H, br); 5.04 (2H, m); 3.29 (2H, br); 2.90 (1H, br); 2.33 (2H, br); 1.67-1.10 (11H, m).

Preparative Example 1.14

Preparation of
3-benzyloxy-N-(1-cyclopropyl)methylmorphinan 17

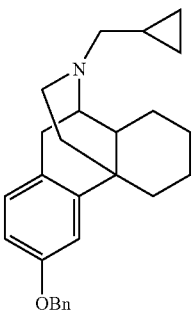

17

To a solution of compound 16 (6 mg, 0.016 mmol) in dry DMF (0.16 mL) were added potassium carbonate (6.6 mg, 0.048 mmol) and cyclopropylmethyl bromide (2.3 μL, 0.024 mmol) sequentially and the mixture was refluxed at 50° C. After 3 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 4.5 mg (72%) of a white solid: $^1$H NMR (300 MHz, CDCl$_3$) δ7.43-7.26 (5H, m); 6.99 (1H, m); 6.86 (1H, m); 6.75 (1H, m); 5.01 (2H, m); 3.07 (1H, br); 2.90 (1H, m); 2.67-2.45 (3H, m); 2.32-2.28 (2H, m); 1.98 (1H, m); 1.81-1.25 (10H, m); 0.86 (1H, br); 0.49 (2H, br); 0.09 (2H, br).

Preparative Example 1.15

Preparation of 3-benzyloxy-N-allylmorphinan 18

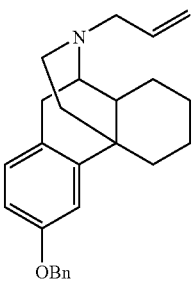

18

To a solution of compound 16 (6 mg, 0.016 mmol) in dry DMF (0.16 mL) were added potassium carbonate (6.6 mg, 0.048 mmol) and allyl bromide (2.1 μL, 0.024 mmol) sequentially and the mixture was refluxed at 50° C. After 3 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 5.1 mg (85%) of a white solid: $^1$H NMR (300 MHz, CDCl$_3$) δ 7.46-7.30 (5H, m); 7.05 (1H, m); 6.89 (1H, m); 6.80

(1H, m); 5.88 (1H, br); 5.24-5.15 (2H, m); 5.03 (2H, m); 3.19 (2H, br); 2.94 (2H, br); 2.59 (2H, m); 2.30 (1H, m); 2.04 (2H, br); 1.83-1.13 (9H, m).

Preparative Example 1.16

Preparation of 3-benzyloxy-N-benzylmorphinan 19

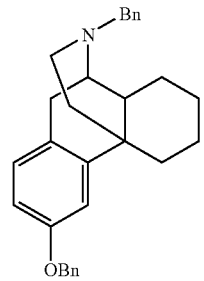

To a solution of compound 16 (6 mg, 0.016 mmol) in dry DMF (0.16 mL) were added potassium carbonate (6.6 mg, 0.048 mmol) and benzyl bromide (2.9 μL, 0.024 mmol) sequentially and the mixture was refluxed at 50° C. After 3 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 6.2 mg (91%) of a white solid: $^1$H NMR (300 MHz, CDCl$_3$) δ7.43-7.23 (10H, m); 6.87 (1H, m); 6.86 (1H, m); 6.77 (1H, m); 5.01 (2H, m); 3.73-3.58 (2H, m); 2.99 (1H, m); 2.83 (1H, br); 2.62-2.56 (1H, m); 2.43 (1H, m); 2.28 (1H, m); 2.12 (1H, m); 1.85-1.14 (10H, m).

Preparative Example 1.17

Preparation of 3-benzyloxy-N-(methanesulfonyl)morphinan 20

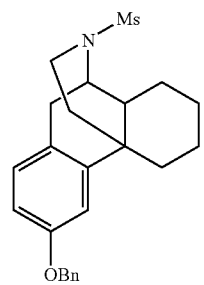

To a solution of compound 16 (6 mg, 0.016 mmol) in dry CH$_2$Cl$_2$ (0.16 mL) were added triethylamine (6.7 μL, 0.048 mmol) and methanesulfonyl chloride (1.9 μL, 0.024 mmol) sequentially and the mixture was stirred for 2 h at room temperature. To the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 5.7 mg (87%) of a white solid: $^1$H NMR (300 MHz, CDCl$_3$) δ7.44-7.25 (5H, m); 7.04 (1H, m); 6.89 (1H, m); 6.83 (1H, m); 5.05 (2H, m); 4.09 (1H, m); 3.70 (1H, m); 3.38-2.78 (6H, m); 2.28 (1H, m); 1.82-1.12 (10H, m).

Preparative Example 1.18

Preparation of 3-benzyloxy-N-(p-toluenesulfonyl)morphinan 21

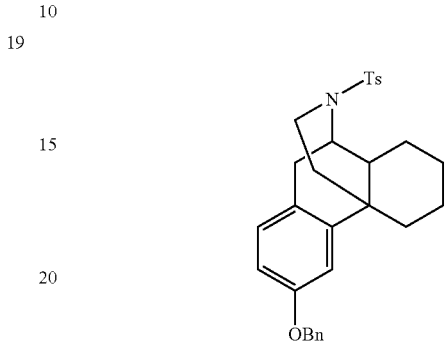

To a solution of compound 16 (6 mg, 0.016 mmol) in dry CH$_2$Cl$_2$ (0.16 mL) were added triethylamine (6.7 μL, 0.048 mmol) and p-toluenesulfonyl chloride (4.6 mg, 0.024 mmol) sequentially and the mixture was stirred for 2 h at room temperature. To the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 7.2 mg (92%) of a white solid: $^1$H NMR (300 MHz, CDCl$_3$) δ 7.71-7.68 (2H, m); 7.43-7.26 (7H, m); 6.84 (2H, m); 6.75 (1H, m); 5.00 (2H, m); 4.12 (1H, m); 3.59 (1H, m); 2.89 (1H, m); 2.67 (1H, m); 2.46 (4H, m); 2.26 (1H, m); 1.74-1.09 (10H, m).

Preparative Example 1.19

Preparation of 3-(4-bromobenzyloxy)-N-(tert-butyloxycarbonyl)morphinan 22

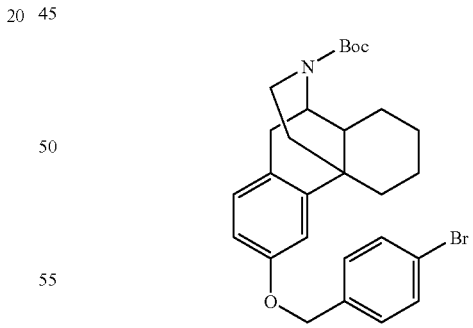

To a solution of 3-hydroxy-N-(tert-butyloxycarbonyl)morphinan (20 mg, 0.058 mmol) in dry DMF (0.3 mL) were added potassium carbonate (17 mg, 0.12 mmol) and p-bromobenzyl bromide (22 mg, 0.087 mmol) sequentially and the mixture refluxed at 60° C. After 5 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 26 mg (86%) of a white solid: $^1$H NMR (300 MHz, CDCl$_3$) δ 7.55-7.50 (2H, m); 7.36-7.25 (2H, m); 7.00 (1H, m); 6.87 (1H, m); 6.77 (1H, m); 5.00 (2H, m); 4.37 (0.59H, br); 4.18 (0.41H, br); 3.75-3.72 (1H, m); 3.06 (1H, m); 2.67-2.61 (2H, m); 2.30 (1H, m); 1.65-1.07 (19H, m).

Preparative Example 1.20

Preparation of 3-(4-bromobenzyloxy) morphinan.HCl 23

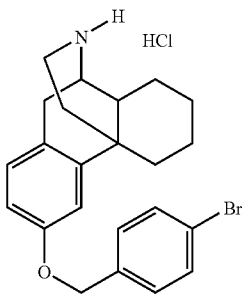

To a solution of compound 22 (26 mg, 0.050 mmol) in dry THF (90 μL) were added 4 N HCl in 1,4-dioxane solution (130 μL) and the mixture stirred for 2 h at room temperature. After starting material disappeared on TLC, solvent was removed under reduced pressure. Simple trituration of the crude product gave 18 mg (96%) of a white solid: $^1$H NMR (300 MHz, CD$_3$OD) δ 7.57-7.51 (2H, m); 7.41-7.35 (2H, m); 7.17 (1H, m); 6.92 (2H, m); 5.07 (2H, m); 3.26-3.10 (2H, m); 2.95-2.81 (1H, m); 2.78 (1H, m); 2.36 (1H, m); 1.73-1.19 (11H, m).

Preparative Example 1.21

Preparation of 3-(4-bromobenzyloxy)-N-(1-cyclopropyl)methylmorphinan 24

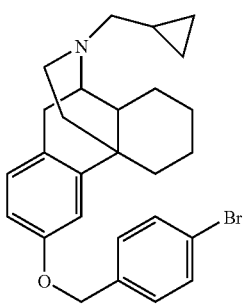

To a solution of compound 23 (6 mg, 0.016 mmol) in dry DMF (0.16 mL) were added potassium carbonate (6.6 mg, 0.048 mmol) and cyclopropylmethyl bromide (2.3 μL, 0.024 mmol) sequentially and the mixture was refluxed at 50° C. After 3 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 5.7 mg (74%) of a white solid: $^1$H NMR (300 MHz, CDCl$_3$) δ 7.51-7.33 (2H, m); 7.30-7.26 (2H, m); 7.01 (1H, m); 6.84 (1H, m); 6.73 (1H, m); 4.98 (2H, m); 3.21 (1H, br); 2.95-2.85 (1H, m); 2.73-2.51 (3H, m); 2.32 (2H, m); 1.98-1.23 (11H, m); 0.75 (1H, br); 0.52 (2H, br); 0.12 (2H, br).

Preparative Example 1.22

Preparation of 3-(p bromobenzyloxy)-N-allylmorphinan 25

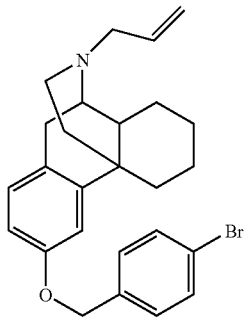

To a solution of compound 23 (6 mg, 0.016 mmol) in dry DMF (0.16 mL) were added potassium carbonate (6.6 mg, 0.048 mmol) and allyl bromide (2.1 μL, 0.024 mmol) sequentially and the mixture was refluxed at 50° C. After 3 h, to the mixture was added sat aq NaCl solution (2 mL) and the mixture was extracted with EtOAc (3 mL×3). The combined organic layer was dried over anhydrous MgSO$_4$, filtered, and concentrated. Column chromatography of the crude product gave 6.3 mg (87%) of a white solid: $^1$H NMR (300 MHz, CDCl$_3$) δ 7.54-7.36 (2H, m); 7.31-7.25 (2H, m); 7.00 (1H, m); 6.82 (1H, m); 6.75 (1H, m); 5.79 (1H, br); 5.28-5.13 (2H, m); 5.01 (2H, m); 3.21 (2H, br); 2.90 (2H, br); 2.62 (2H, m); 2.27 (1H, m); 2.06 (2H, br); 1.85-1.21 (9H, m).

Preparative Example 1.23

Preparation of 3-hydroxy-N-(benzyloxycarbonyl)morphinan 26

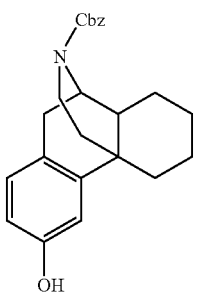

To a stirred solution of 3-hydroxymorphinan (20 mg, 0.061 mmol) and triethylamine (26 μL, 0.183 mmol) in dry Dichloromethane (0.3 mL) was added benzyl chloroformate (10.5 μL, 0.073 mmol) at 0° C. The mixture was stirred for 2 h, and to the mixture was added sat aq NaCl solution (2 mL) and the mixture was extracted with EtOAc (3 mL×3). The combined organic layer was dried over anhydrous MgSO$_4$, filtered, and concentrated, after column chromatography of the crude product gave 12 mg (51%) of title compound: $^1$H NMR (300 MHz, CDCl$_3$) δ7.3~7.5 (5H, m) 6.9 (1H, t); 6.8 (1H, d); 6.6 (1H, t); 5.1 (2H, s); 4.3 (1H, dd); 3.9 (1H, m); 3.1 (1H, m); 2.7 (2H, m); 2.3 (1H, d); 1.0~1.8 (10H, m).

Preparative Example 1.24

Preparation of 3-benzyloxycarbonyloxy-N-(benzyloxycarbonyl)morphinan 27

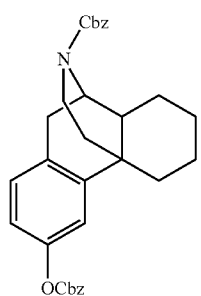

27

To a stirred solution of 3-hydroxymorphinan (5 mg, 0.015 mmol) and triethylamine (13 μL, 0.091 mmol) in dry dichloromethane (0.3 mL) was added benzyl chloroformate (5.2 μL, 0.036 mmol) at 0° C. The reaction mixture was stirred for 2 h at room temperature. After starting material disappeared on TLC, solvent was removed and column chromatography gave 6.3 mg (80%) of title compound: $^1$H NMR (300 MHz, CDCl$_3$) δ7.3~7.6 (10H, m); 7.0 (2H, m); 6.9 (1H, m); 5.3 (2H, s); 5.1 (2H, s); 4.3 (1H, dd); 3.9 (1H, m); 3.1 (1H, m); 2.7 (2H, d); 2.3 (1H, m); 1.0~1.8 (10H, m).

Preparative Example 1.25

Preparation of 3-anilinocarbonyloxy-N-phenyluridomorphinan 28

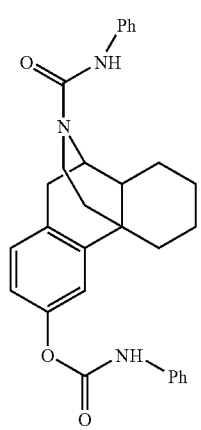

28

To a stirred solution of 3-hydroxymorphinan (5 mg, 0.015 mmol) and triethylamine (8.3 μL, 0.060 mmol) in dry dichloromethane (0.3 mL) was added phenyl isocyanate (5 μL, 0.046 mmol) and the mixture was stirred for 1 h at 0° C. After starting material disappeared on TLC, solvent was removed and column chromatography gave 6.5 mg (88%) of the title compound: $^1$H NMR (300 MHz, CDCl$_3$) δ7.4 (2H, d); 7.2 (6H, m); 7.0 (6H, m); 6.3 (1H, s); 4.4 (1H, s); 3.5 (1H, d. d.); 3.1 (1H, d. d.); 2.8 (2H, m); 2.3 (1H, m); 1.0~1.9 (10H, m).

Preparative Example 1.26

Preparation of 3-anilinocarbonyloxy-N-(tert-butyloxycarbonyl)morphinan 29

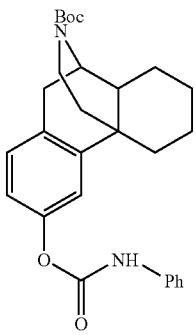

29

To a stirred solution of 3-hydroxy-N-(tert-butyloxycarbonyl)morphinan (9 mg, 0.026 mmol) and triethylamine (10 μL, 0.04 mmol) in dry dichloromethane (0.3 mL) was added phenyl isocyanate (4 μL, 0.045 mmol) and the mixture was stirred for 1 h. After starting material disappeared on TLC, solvent was removed and column chromatography gave 11 mg (90%) of the title compound: $^1$H NMR (300 MHz, CDCl$_3$) δ7.4 (2H, d); 7.3 (2H, t); 7.1 (3H, m); 6.9 (2H, m); 4.3 (1H, m); 3.8 (1H, m); 3.1 (1H, d. d.); 2.4~2.8 (2H, m); 2.3 (1H, m); 1.3 (9H, s); 1.0~1.7 (10H, m).

Preparative Example 1.27

Preparation of 3-anilinocarbonyloxy-morphinan.HCl 30

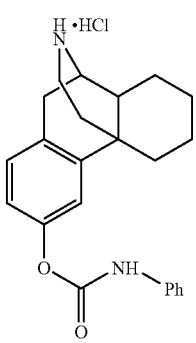

30

To a solution of 3-O-phenylcarbamoyl-N-(tert-butyloxycarbonyl)morphinan D-4 (10 mg, 0.051 mmol) in dry dichloromethane (0.5 mL) was added 4N HCl in 1,4-dioxane solution (120 μL) and the mixture stirred for 2 h at room temperature. After starting material was disappeared on TLC, solvent was concentrated. Simple trituration of the crude product gave 9 mg (96%) of white solid: ¹H NMR (300 MHz, CD₃OD) δ7.5 (2H, d); 7.3 (3H, m); 7.1 (1H, d); 7.0 (2H, m); 3.9 (1H, m); 3.0~3.4 (3H, m); 2.8 (1H, m); 2.5 (1H, m); 1.0~1.9 (10H, m).

Preparative Example 1.28

Preparation of N-Boc-3-pivaloyloxymorphinan 31

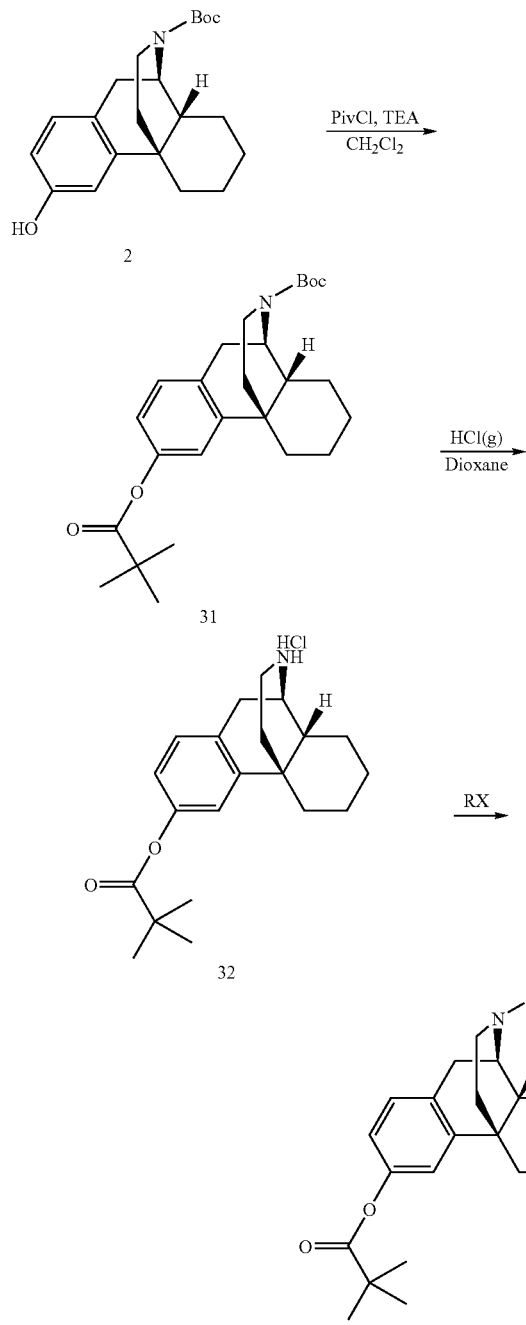

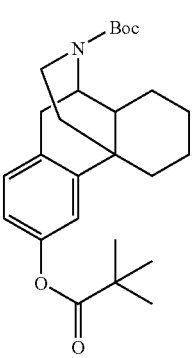

To a solution of N-Boc-3-hydroxymorphinan 2 (20 mg, 0.058 mmol) and triethylamine (9 µL, 0.064 mmol) in dry CH₂Cl₂ (1 mL) was slowly added pivaloyl chloride (8 µL, 0.064 mmol) at 0° C. and the mixture stirred for 1 h. Solvent was removed under reduced pressure. The crude product was purified on a silica gel column chromatography (5:1 n-Hexane/EtOAc) to give a colorless oil (23 mg, 92% yield): ¹H NMR (300 MHz, CDCl₃) 0.9~1.7 (m, 29H); 2.34 (d, J=9.9 Hz, 1H); 2.52~2.73 (m, 2H); 3.09~3.17 (m, 1H); 3.73~3.84 (m, 1H); 6.83~6.87 (m, 1H); 6.95 (s, 1H); 7.09~7.12 (m, 1H).

Preparative Example 1.29

Preparation of N-(1-cycloprypyl)methyl-3-pivaloyloxy-morphinan 33

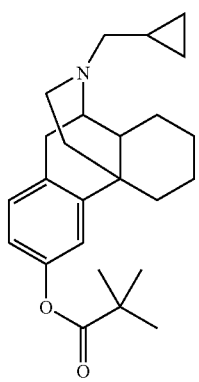

To a solution of N-Boc-3-pivaloyloxymorphinan (5 mg, 0.012 mmol) in dry CH₂Cl₂ (0.2 mL) was added 4 M HCl dioxane solution (0.5 mL) and stirred for 2 h at 0° C. Solvent was evaporated under reduced pressure. The crude HCl salt of 3-pivaloyloxy morphinan 32 was dissolved in CH₃CN (0.5 ml) and to it were slowly added (bromomethyl)cyclopropane (2 µL, 0.020 mmol) and TEA (9 µL, 0.064 mmol) at 0° C. After 10 h stirring, the reaction mixture was concentrated under reduced pressure. The crude product was purified on a silica gel column chromatography (95:5 CH₂Cl₂/MeOH) to give a colorless oil (3 mg, 65% yield): ¹H NMR (300 MHz, CDCl₃) 0.43~1.58 (m, 24H); 2.35~2.52 (m, 2H); 2.69~2.73 (m, 1H); 2.90~2.96 (m, 2H); 3.16~3.35 (m, 2H); 3.91 (s, 1H); 6.92~6.96 (m, 1H); 6.99 (s, 1H); 7.17 (d, J=8.2 Hz, 1H).

Preparative Example 1.30

Preparation of N-benzyl-3-pivaloyloxymorphinan 34

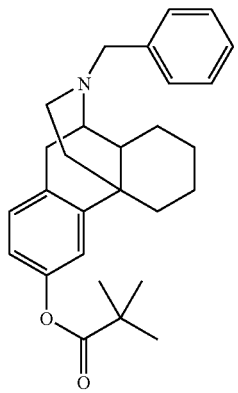

34

To a solution of compound 31 (5 mg, 0.012 mmol) in dry CH$_2$Cl$_2$ (0.2 ml) was added 4 M HCl dioxane solution (0.5 mL) and the mixture stirred for 2 h at 0° C. Solvent was evaporated under reduced pressure. The crude amine salt 32 was dissolved in CH$_2$Cl$_2$ (0.5 ml) and to it were slowly added benzyl bromide (2 μL, 0.020 mmol) and TEA (9 μL, 0.064 mmol) at 0° C. After 4 h stirring, the reaction mixture was concentrated under reduced pressure. The crude product was purified on a silica gel column chromatography (3:1 n-Hexane/EtOAc) to give a colorless oil (4 mg, 80% yield): $^1$H NMR (300 MHz, CDCl$_3$) 0.91~1.74 (m, 18H); 1.89 (m, J=12.6 Hz, 1H); 2.07~2.21 (m, 1H), 2.29~2.48 (m, 2H); 2.63~2.69 (m, 1H); 2.87 (s, 1H); 3.09 (d, J=18.3 Hz, 1H); 3.68 (dd, J=13.4 Hz, 2H); 6.82~6.93 (m, 2H); 7.15 (d, J=8.3 Hz, 1H); 7.25~7.38 (m, 5H).

Preparative Example 1.31

Preparation of N-(2-propynyl)-3-pivaloyloxymorphinan 35

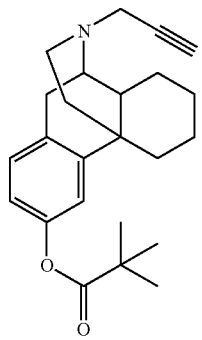

35

To a solution of compound 31 (5 mg, 0.012 mmol) in dry CH$_2$Cl$_2$ (0.2 mL) was added 4 M HCl dioxane solution (0.5 mL) and the mixture stirred for 2 h at 0° C. Solvent was evaporated under reduced pressure. The crude amine salt 32 was dissolved in CH$_2$Cl$_2$ (0.5 mL) and to the mixture was slowly added 80 wt % propargyl bromide solution in toluene (2 μL, 0.020 mmol) and TEA (9 μL, 0.064 mmol) at 0° C. After 4 h stirring, the reaction mixture was concentrated under reduced pressure. The crude product was purified on a silica gel column chromatography (1:1 n-Hexane/EtOAc) to give a colorless oil (3 mg, 68% yield): $^1$H NMR (300 MHz, CDCl$_3$) 1.15~1.87 (m, 20H); 2.14~2.31 (m, 2H); 2.67~2.74 (m, 2H); 3.02 (d, J=18.6 Hz, 1H); 3.12~3.14 (m, 1H); 3.36~3.39 (m, 2H); 6.81~6.93 (m, 2H); 7.16 (d, J=8.2 Hz, 1H).

Preparative Example 1.32

Preparation of N-methanesulfonyl-3-pivaloyloxymorphinan 36

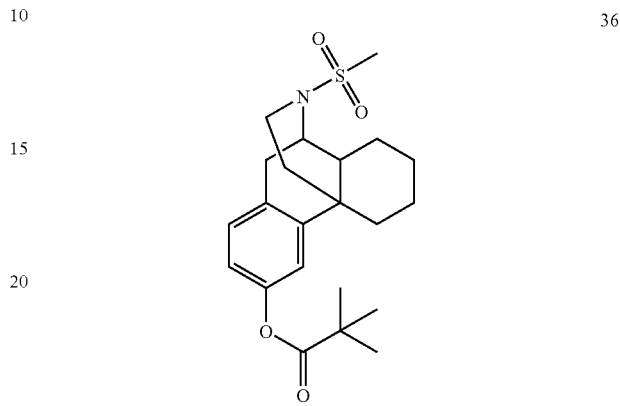

36

To a solution of compound 31 (5 mg, 0.012 mmol) in dry CH$_2$Cl$_2$ (0.2 mL) was added 4 M HCl dioxane solution (0.5 mL) and stirred for 2 h at 0° C. The solvent was evaporated under reduced pressure. The crude amine salt 32 was dissolved in CH$_2$Cl$_2$ (0.5 mL) and slowly added methanesulfonyl chloride (2 μL, 0.030 mmol) and TEA (9 μL, 0.064 mmol) at 0° C. After 1 h stirring, the reaction mixture was concentrated under reduced pressure. The crude product was purified on a silica gel column chromatography (3:1 n-Hexane/EtOAc) to give a colorless oil (3 mg, 82% yield): $^1$H NMR (300 MHz, CDCl$_3$) 1.08~1.87 (m, 20H); 2.36 (d, J=12.4 Hz, 1H); 2.77~2.92 (m, 5H); 3.51~3.54 (m, 1H); 4.10~4.15 (m, 1H); 6.86~6.96 (m, 2H); 7.13 (d, J=8.3 Hz, 1H).

Preparative Example 1.33

Preparation of 3-(trifluoromethanesulfonyloxy)morphinan 38

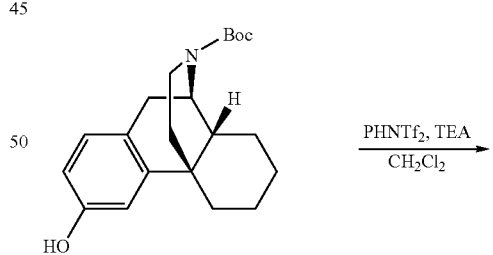

87

-continued

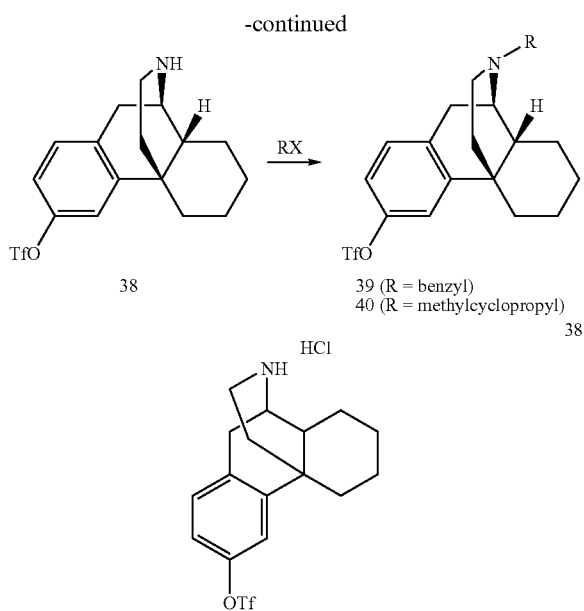

38

39 (R = benzyl)
40 (R = methylcyclopropyl)

To a solution of compound 2 (200 mg, 0.58 mmol) and TEA (0.32 mL, 2.32 mmol) in dry $CH_2Cl_2$ (5 mL) was slowly added $PhNTf_2$ (414 mg, 1.16 mmol) at 0° C. The reaction mixture was allowed to warm to room temperature and stirred for 6 h. The solution was diluted with $CH_2Cl_2$, washed with sat aq $NaHCO_3$ solution, and then dried over sodium sulfate. It was filtered and the filtrate concentrated under reduced pressure to afford a crude product 37. To solution of crude 37 in dry $CH_2Cl_2$ (1 mL) was added 4 M HCl dioxane solution (5 mL) and the mixture stirred for 5 h at room temperature. Solvent was removed in vacuo. The crude amine salt was purified on a silica gel column chromatography (90:5:5 $CH_2Cl_2$/MeOH/TEA) to give a pale yellow oil (184 mg, 85% yield): $^1$H NMR 300 MHz, $CDCl_3$) 0.96~2.04 (m, 12H); 2.27~3.18 (m, 4H); 3.45 (s, 1H); 7.07~7.15 (m, 2H); 7.22 (s, 1H).

Preparative Example 1.34

Preparation of N-benzyl-3-(trifluoromethanesulfonyloxy)morphinan 39

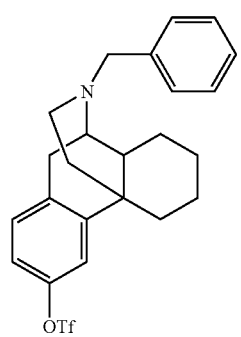

39

To a solution of compound 38 (50 mg, 0.13 mmol) and TEA (74 μL, 0.53 mmol) in dry $CH_2Cl_2$ (2 mL) was slowly added benzyl bromide (32 μL, 0.27 mmol) at 0° C. and stirred for 5 h. Solvent was removed under reduced pressure. The crude product was purified on a silica gel column chromatography (90:5 $CH_2Cl_2$/MeOH) to give a colorless oil (51 mg,

88

84% yield): $^1$H NMR (300 MHz, $CDCl_3$) 1.05~1.72 (m, 9H); 1.74~1.85 (m, 1H); 1.90~1.94 (m, 1H); 1.96~2.05 (m, 1H); 2.31 (d, J=13.0 Hz, 1H); 2.48~2.52 (m, 1H); 2.88~2.91 (m, 1H); 3.12 (d, J=18.6 Hz, 1H); 3.67 (dd, J=13.4 Hz, 2H); 7.03~7.38 (m, 8H).

Preparative Example 1.35

Preparation of N-(1-cyclopropyl)methyl-3-(trifluoromethanesulfonyloxy)morphinan 40

40

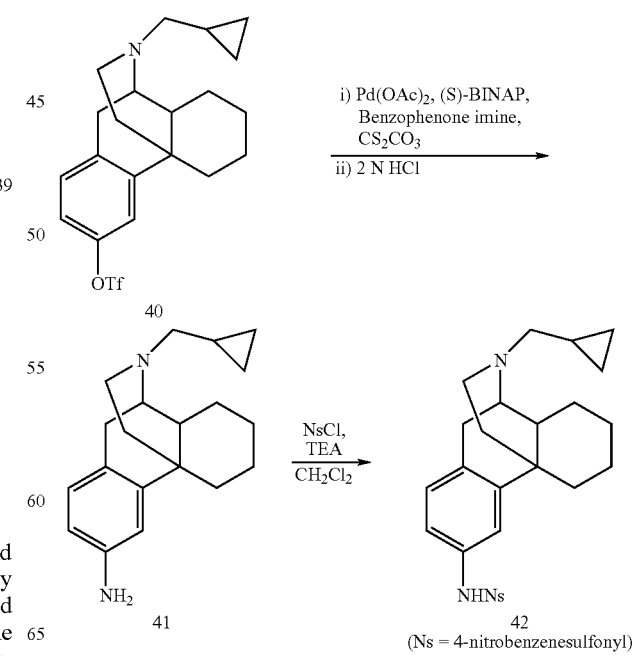

To a solution of compound 38 (50 mg, 0.13 mmol) and TEA (74 μL, 0.53 mmol) in dry $CH_2Cl_2$ (2 mL) was slowly added (bromomethyl)cyclopropane (25 μL, 0.26 mmol) at 0° C. and the mixture stirred for 5 h. Solvent was removed under reduced pressure. The crude product was purified on a silica gel column chromatography (95:5 $CH_2Cl_2$/MeOH) to give a white solid (43 mg, 77% yield): $^1$H NMR (300 MHz, $CDCl_3$) 0.19~2.10 (m, 17H); 2.31 (d, J=13.8 Hz, 1H); 2.47~2.59 (m, 2H); 2.78~2.88 (m, 2H); 3.30 (s, 1H); 7.02~7.06 (m, 1H); 7.13~7.20 (m, 2H).

Preparative Example 1.36

Preparation of Compound 41

A round bottom flask were charged with Pd(OAc)$_2$ (1 mg, 0.0045 mmol), (S)-(−)-BINAP (3 mg, 0.0045 mmol), and Cs$_2$CO$_3$ (22 mg, 0.069 mmol) and flushed with argon. To the mixture N-(1-cyclopropyl)methyl-3-(trifluoromethanesulfonyloxy)morphinan (40) (20 mg, 0.046 mmol) in DMF (1 mL) and benzophenoneimine (13 mg, 0.069 mmol) were added. The mixture was heated at 80° C. for 12 h, then treated with 2 N HCl solution (3 mL) at room temperature for 2 h. Solvent was removed under reduced pressure. The crude product was purified on a silica gel column chromatography (95:5:5 CH$_2$Cl$_2$/MeOH/TEA) to give a white solid (10 mg, 73% yield): $^1$H NMR (300 MHz, CDCl$_3$) 0.15~3.24 (m, 25H); 6.62~6.65 (m, 1H); 6.75 (d, J=2.2 Hz, 1H); 6.94 (d, J=8.2 Hz, 1H).

Preparative Example 1.37

Preparation of Compound 42

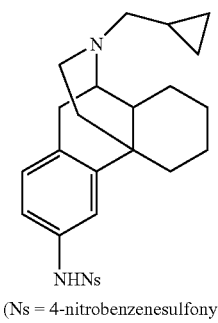

42

(Ns = 4-nitrobenzenesulfonyl)

To a solution of compound 41 (5 mg, 0.017 mol) and TEA (7 ul, 0.051 mmol) in dry CH$_2$Cl$_2$ (1 ml) was slowly added 4-nitrobenzenesulfonyl chloride (7 mg, 0.034 mmol) at 0° C. and the mixture stirred for 1 h. Solvent was removed under reduced pressure. The crude product was purified on a silica gel column chromatography (95:5 CH$_2$Cl$_2$/MeOH) to give a colorless oil (6 mg, 83% yield): $^1$H NMR (300 MHz, CDCl$_3$) 0.19~0.63 (m, 8H); 0.96~2.11 (m, 13H); 2.55~3.53 (m, 6H); 6.83~6.87 (m, 2H); 7.10 (d, J=8.3 Hz, 1H); 8.10 (d, J=8.7 Hz, 2H); 8.38 (d, J=8.7 Hz, 2H).

Preparative Example 1.38

Preparation of Compound 43

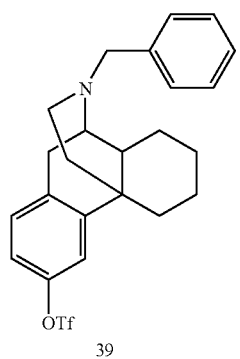

39

1. Pd(OAc)$_2$, (S)-BINAP, Benzophenone imine, Cs$_2$CO$_3$
2. 2 N HCl
3. NsCl, TEA, CH$_2$Cl$_2$

→

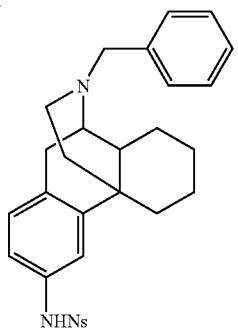

43

(Ns = 4-nitrobenzenesulfonyl)

A round bottom flask was charged with Pd(OAc)$_2$ (1 mg, 0.0045 mmol), (S)-(−)-BINAP (3 mg, 0.0045 mmol), and Cs$_2$CO$_3$ (22 mg, 0.069 mmol) and flushed with argon. Triflate 39 (20 mg, 0.046 mmol) in DMF (1 mL) and benzophenone imine (13 mg, 0.069 mmol) were added. The mixture was heated at 80° C. for 12 h, and then treated with 2 N aq HCl solution (3 mL) at room temperature for 2 h. Solvent was removed under reduced pressure. To a solution of the crude compound and TEA (17 µL, 0.127 mmol) in dry CH$_2$Cl$_2$ (1 mL) was slowly added 4-nitrobenzenesulfonyl chloride (8 mg, 0.041 mmol) at 0° C. and stirred for 1 h. The solvent was concentrated under reduced pressure. The crude product was purified on a silica gel column chromatography (2:1 n-Hexane/EtOAc) to give a colorless oil (6 mg, 83% yield): $^1$H NMR (300 MHz, CDCl$_3$) 0.89~2.06 (m, 12H); 2.46~2.701 (m, 2 H); 2.87 (s, 1H); 3.06 (d, J=18.6 Hz, 1H); 3.54~4.10 (m, 2H); 6.76 (s, 1H); 6.83~6.86 (m, 1H); 7.12 (d, J=8.4 Hz, 1H); 8.04 (d, J=8.8 Hz, 2H).

Preparative Example 1.39

Preparation of 3-vinyl-N-(tert-butyloxycarbonyl)morphinan 44

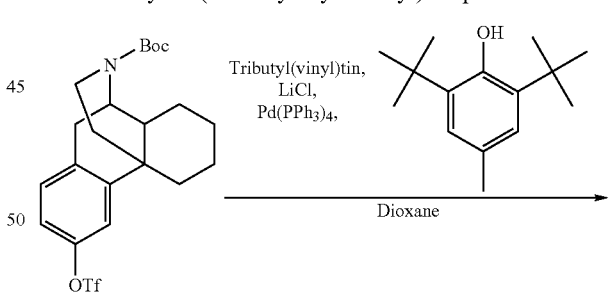

37

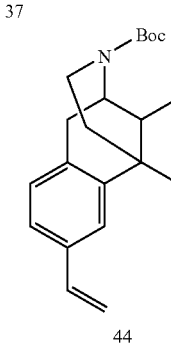

44

-continued

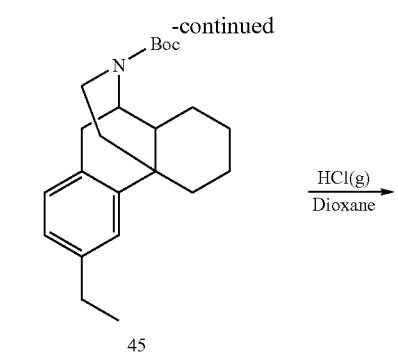

45

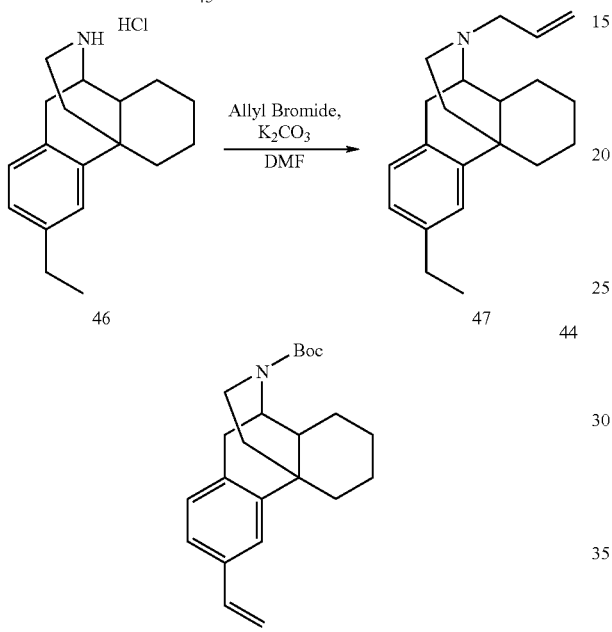

To a stirred solution of 3-O-(trifluoromethansulfonyl)-N-(tert-butyloxycarbonyl)morphinan 37 (18 mg, 0.039 mmol) in dry 1,4-dioxane (0.8 mL) were added tributyl(vinyl)tin (17 μL, 0.059 mmol), LiCl (17.3 μL, 0.117 mmol), Pd(PPh₃)₄ (17.3 μL, 0.174 mmol), and a few crystals of 2,6-di-tert-butyl-4-methylphenol. The resulting suspension was heated to reflux. After starting material disappeared on TLC, solvent was evaporated and column chromatography of the residue gave 8 mg (59%) of the title compound: ¹H NMR (300 MHz, CDCl₃) δ7.25~7.32 (2H, m) 7.05 (1H, d); 6.62 (1H, d.d.); 5.78 (1H, d); 5.20 (1H, d); 4.30 (1H, m); 3.55~4.80 (1H, m); 3.10 (1H, m); 2.30~2.65 (2H, m); 2,05 (1H, m); 1.23 (9H, s); 1.00~1.80 (10H, m).

Preparative Example 1.40

Preparation of 3-Ethyl-N-(tert-butyloxycarbonyl)morphinan, 45

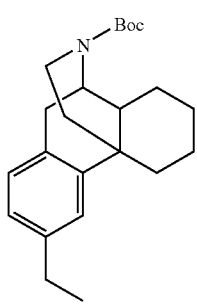

45

To a stirred solution of 3-vinyl-N-(tert-butyloxycarbonyl)morphinan, 44 (10 mg, 0.028 mmol) in dry methanol (1 mL) was added Pd/C (4 mg) and the flask was charged with hydrogen gas in a balloon. After starting material disappeared on TLC, solvent was evaporated and column chromatography of the residue gave 7 mg (70%) of product: ¹H NMR (300 MHz, CDCl₃) δ7.06~7.36 (3H, m); 4.37 (0.5H, s); 4.19 (0.5H, s); 3.88 (1H, dd); 3.11 (1H, m); 2.63 (2H, m); 2.59 (2H, m); 2.44 (1H, m); 1.60~1.80 (4H, m); 1.40~1.60 (9H, d); 0.90~1.40 (9H, m).

Preparative Example 1.41

Preparation of 3-Ethylmorphinan.HCl 46

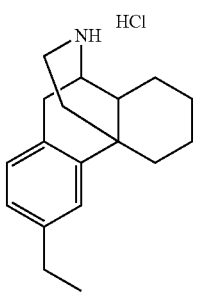

46

To a stirred solution of 3-Ethyl-N-(tert-butyloxycarbonyl)morphinan 45 (6 mg, 0.017 mmol) in dry DCM (1 mL) was added 4N HCl in 1,4-dioxane solution (300 μL) and the mixture stirred for 4 h at room temperature. After starting material was disappeared on TLC, solvent was evaporated. ¹H NMR (300 MHz, CDCl₃) δ7.13~7.46 (3H, m); 3.27 (2H, m); 3.19 (2H, s); 2.88 (1H, m); 2.81 (1H, m); 2.58 (2H, m); 1.10~1.80 (13H, m).

Preparative Example 1.42

Preparation of 3-Ethyl-N-Allylmorphinan 47

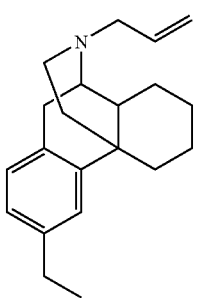

47

To a stirred solution of 3-Ethylmorphinan.HCl 46 (3 mg, 0.01 mmol) in dry DMF (0.6 mL) was added potassium carbonate (5 mg, 0.036 mmol), allyl bromide (5.0 μL, 0.060 mmol) sequentially and the mixture was refluxed. After 2 h, the mixture was dried over anhydrous MgSO₄, filtered, and concentrated. Column chromatography of the product gave -2 mg of white solid. ¹H NMR (300 MHz, CDCl₃) δ 6.89~7.16 (3H, m); 5.80 (1H, d); 5.16~5.30 (2H, m); 4.00~4.30 (1H, dd); 3.68 (2H, t); 3.66 (1H, m); 3.15 (1H, br); 2.68 (2H, m); 2.50 (2H, m); 2.38 (1H, m); 1.10~1.70 (13H, m).

Preparative Example 1.43

Preparation of 3-(1',2'-dihydroxyethyl)-N-(tert-butyloxycarbonyl)morphinan 48

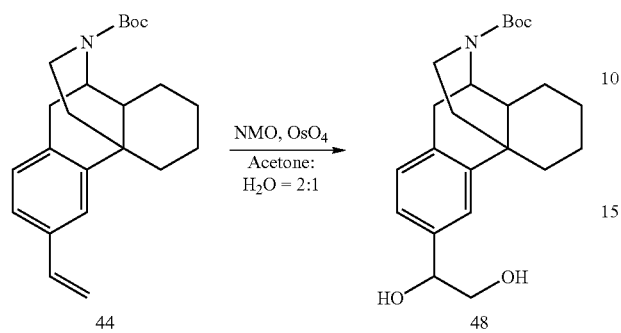

To a stirred solution of 3-vinyl-N-(tert-butyloxycarbonyl)morphinan 44 (10.5 mg, 0.03 mmol) in acetone:water=2:1 solution (0.3 mL) were added N-methylmorpholine-N-oxide (10 μL, 50 wt. % in water), and osmium tetroxide (one drop) sequentially and the mixture was stirred for 2 h at rt. After starting material disappeared on TLC, ethyl acetate (2 mL) and aqueous Na$_2$SO$_3$ solution (2 mL) were poured into the mixture, and the organic layer was separated, dried over MgSO$_4$, and concentrated. Column chromatography gave 10 mg (87%) of the title compound: $^1$H NMR (300 MHz, CDCl$_3$) δ7.29~7.36 (1H, m); 7.17~7.10 (2H, m); 4.79 (1H, d); 4.37 (0.55H, br); 4.19 (0.45H, br); 3.77~3.66 (3H, m); 3.11 (1H, m); 2.72~2.41 (4H, m); 2.03 (1H, m); 1.71~1.04 (19H, m).

Preparative Example 1.44

Preparation of 3-Phenylcarbamoyloxy-N-(3-chloropropyl)morphinan 49

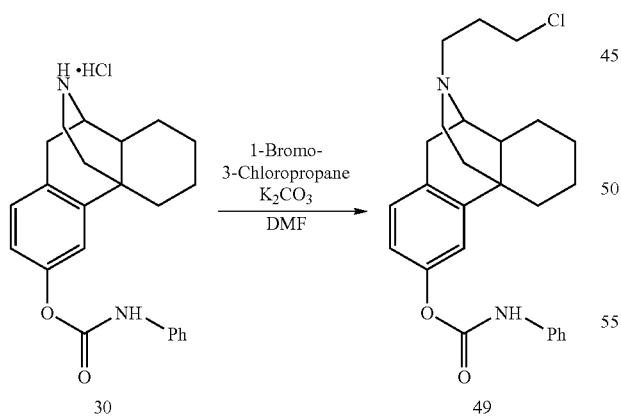

To a stirred solution of 3-phenylcarbamoyloxymorphinan.HCl 30 (2.8 mg, 0.007 mmol) in dry DMF (0.15 mL) was added potassium carbonate (5.4 mg, 0.021 mmol), 1-bromo-3-chloropropane (1.9 μL, 0.042 mmol) sequentially and the mixture was stirred at 50° C. After starting material disappeared on TLC, solvent was concentrated and column chromatography gave 2.1 mg (70%) of the title compound: $^1$H NMR (300 MHz, CDCl$_3$) δ7.35 (4H, m); 7.10 (2H, m); 6.85 (1H, d); 6.75 (1H, d.d.); 6.28 (1H, s); 4.38 (1H, m); 4.10 (2H, t); 3.80 (2H, t); 3.65 (1H, m); 3.14 (1H, d.d.); 2.83 (2H, m); 2.37 (1H, m); 2.25 (2H, m); 1.00~1.80 (10H, m).

Preparative Example 1.45

Preparation of 3-Phenylcarbamoyloxy-N-(methanesulfonyl)morphinan 50

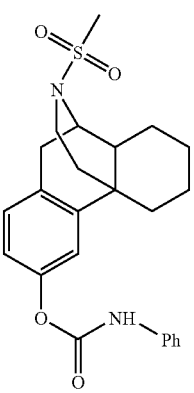

To a stirred solution of 3-O-phenylcarbamoyloxymorphinan.HCl 30 (2.8 mg, 0.007 mmol) and triethylamine (5.4 μL, 0.042 mmol) in dry dichloromethane (0.3 mL) was added methanesulfonylchloride (1.5 μL, 0.021 mmol) and the mixture stirred at room temperature. After starting material disappeared on TLC, solvent was removed and column chromatography gave 2.1 mg (70%) of the title compound: $^1$H NMR (300 MHz, CDCl$_3$) δ7.48 (2H, d); 7.31 (2H, t); 7.15 (3H, m); 7.04 (1H, m); 6.90 (1H, s); 4.11 (1H, m); 3.55 (1H, m); 3.18 (1H, m); 2.93 (3H, s); 2.84 (2H, m); 2.30 (1H, d); 1.00~1.80 (10H, m).

Preparative Example 1.46

Preparation of 3-Phenylcarbamoyloxy-N-acetylmorphinan 51

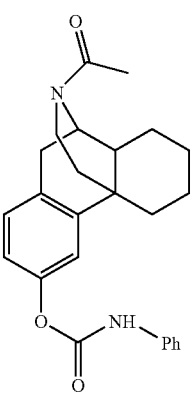

To a stirred solution of 3-O-phenylcarbamoyloxymorphinan.HCl 30 (2.8 mg, 0.007 mmol) and triethylamine (5.4 μL, 0.042 mmol) in dry dichloromethane (0.3 mL) was added acetyl chloride (1.4 μL, 0.021 mmol) and the mixture was stirred at room temperature. After starting material disappeared on TLC, solvent was removed and column chromatography gave 2 mg (70%) of the title compound: $^1$H NMR (300 MHz, CDCl$_3$) δ 7.45 (2H, d); 7.30 (2H, t); 7.15 (3H, m); 7.03 (2H, m); 4.95 (1H, m); 3.55 (1H, m); 3.15 (1H, m); 2.90 (1H, m); 2.75 (1H, m); 2.30 (1H, m); 2.05 (3H, s); 1.00~1.80 (10H, m).

Preparative Example 1.47

Preparation of 3-(3-Chloropropyloxy)-N-(benzyloxycarbonyl)morphinan 52

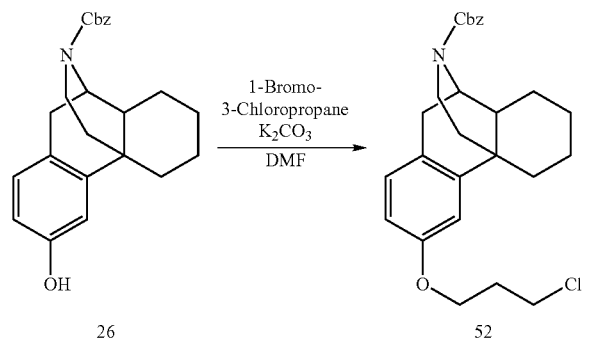

To a stirred solution of 3-hydroxy-N-(benzyloxycarbonyl)morphinan 26 (3.6 mg, 0.009 mmol) in dry DMF (0.16 mL) were added potassium carbonate (4 mg, 0.028 mmol), 1-bromo-3-chloropropane (2.8 μL, 0.028 mmol) sequentially and the mixture was stirred at 50° C. After starting material disappeared on TLC, solvent was removed and column chromatography gave 3 mg (70%) of the title compound: $^1$H NMR (300 MHz, CDCl$_3$) δ 7.30 (5H, m); 7.00 (1H, t); 6.83 (1H, d); 6.70 (1H, d. d.); 5.10 (2H, m); 4.30 (1H, m); 4.05 (2H, t); 3.90 (1H, m); 3.79 (2H, t); 3.05 (1H, m); 2.75 (2H, m); 2.30 (1H, m); 2.15 (2H, m); 1.00~1.80 (10H, m).

Preparative Example 1.48

Preparation of 3-(3-chloropropyloxy)-N-(tert-butyloxycarbonyl)morphinan 53

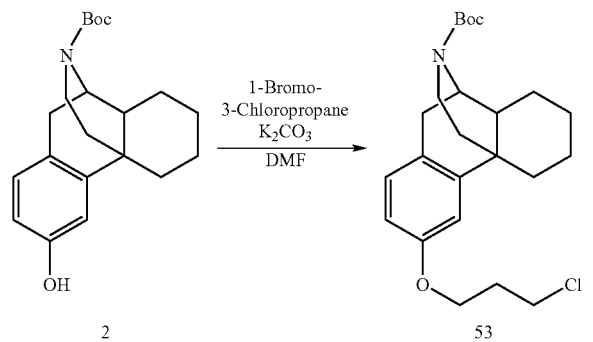

To a stirred solution of 3-hydroxy-N-(tert-butyloxycarbonyl)morphinan (20 mg, 0.058 mmol) in dry DMF (0.3 mL) was added potassium carbonate (24 mg, 0.174 mmol), 1-bromo-3-chloropropane (17.3 μL, 0.174 mmol) sequentially and the mixture was stirred at 50° C. After starting material disappeared on TLC, solvent was removed and column chromatography gave 18 mg (74%) of the title compound: $^1$H NMR (300 MHz, CDCl$_3$) δ 7.05 (1H, m); 6.83 (1H, d); 6.75 (1H, d.d.); 4.28 (1H, d); 4.05 (2H, t); 3.90 (1H, m); 3.83 (3H, t); 3.15 (1H, m); 2.60 (2H, m); 2.30 (1H, m); 2.15 (1H, m); 1.30 (9H, s); 1.00~1.80 (10H, m).

Preparative Example 1.49

Preparation of 3-(3-chloropropyloxy)morphinan.HCl 54

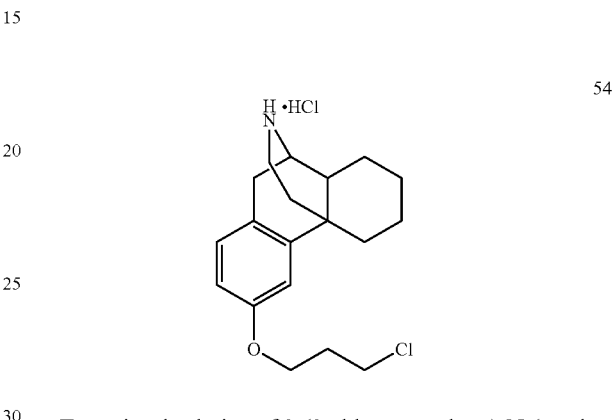

To a stirred solution of 3-(3-chloropropyloxy)-N-(tert-butyloxycarbonyl)morphinan 53 (17 mg, 0.04 mmol) in dry dichloromethane (1.0 mL) was added 4 N HCl in 1,4-dioxane solution (200 μL) and the mixture stirred for 2 h at room temperature. After starting material disappeared on TLC, solvent was concentrated. Simple trituration of the crude product gave 14 mg (97%) of a white solid: $^1$H NMR (300 MHz, CD$_3$OD) δ 7.15 (1H, d); 6.80~7.10 (2H, m); 4.05 (2H, t); 3.78 (2H, t); 3.65 (2H, m); 3.30 (1H, m); 3.10 (2H, m); 2.78 (1H, m); 2.45 (1H, m); 2.18 (2H, m); 1.00~2.00 (10H, m).

Preparative Example 1.50

Preparation of 3-(3-chloropropyloxy)-N-(methanesulfonyl)morphinan 55

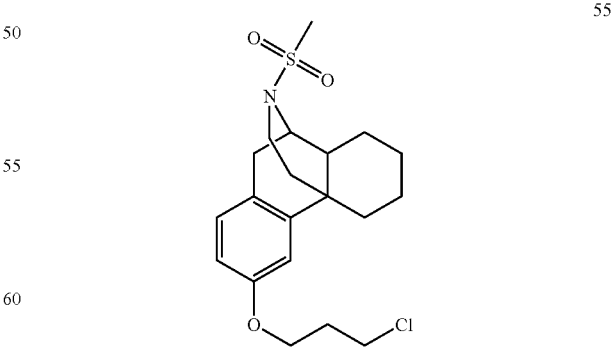

To a stirred solution of 3-(3-chloropropyloxy)morphinan. HCl 54 (3 mg, 0.008 mmol) and triethylamine (7 μL, 0.050 mmol) in dry dichloromethane (0.3 mL) was added methanesulfonylchloride (2 μL, 0.025 mmol) and the mixture was stirred at room temperature. After starting material disappeared on TLC, solvent was removed and column chromatography gave 3 mg (88%) of title compound: $^1$H NMR (300 MHz, CDCl$_3$) δ7.01 (1H, m); 6.85 (1H, d); 6.70 (1H, d.d); 4.05 (3H, m); 3.78 (2H, t); 3.56 (1H, d.d.); 3.15 (1H, d.d.); 2.90 (3H, s); 2.83 (2H, m); 2.32 (1H, m); 2.20 (2H, m); 1.00~1.90 (10H, m).

Preparative Example 1.51

Preparation of
3-(3-chloropropyloxy)-N-acetylmorphinan 56

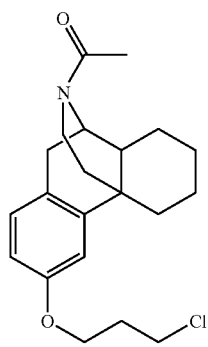

56

To a stirred solution of 3-(3-chloropropyloxy)morphinan. HCl 54 (3 mg, 0.008 mmol) and triethylamine (7 μL, 0.050 mmol) in dry dichloromethane (0.3 mL) was added acetyl chloride (1.8 μL, 0.025 mmol) and the mixture was stirred at room temperature. After starting material disappeared on TLC, solvent was concentrated and column chromatography gave 2.5 mg (82%) of the title compound: $^1$H NMR (300 MHz, CDCl$_3$) δ6.96 (1H, t); 6.83 (1H, d); 6.75 (1H, d. d.); 4.92 (1H, m); 4.15 (2H, t); 3.81 (2H, t); 3.75 (1H, m); 3.12 (1H, m); 2.95 (1H, m); 2.62 (1H, m); 2.30 (1H, m); 2.18 (2H, m); 2.05 (3H, s); 1.00~1.80 (10H, m).

Preparative Example 1.52

Preparation of
3-(3-chloropropyloxy)-N-benzylmorphinan 57

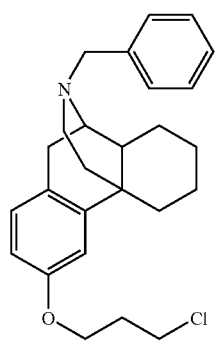

57

To a stirred solution of 3-(3-chloropropyloxy)morphinan. HCl 54 (3 mg, 0.008 mmol) in dry DMF (0.15 mL) was added potassium carbonate (7 mg, 0.024 mmol), benzylbromide (2 μL, 0.032 mmol) sequentially and the mixture was stirred at 50° C. After starting material disappeared on TLC, solvent was concentrated and column chromatography gave 3 mg (87%) of the title compound: $^1$H NMR (300 MHz, CDCl$_3$) δ7.15~7.35 (5H, m); 7.05 (1H, d); 6.80 (1H, s); 6.73 (1H, d); 4.10 (2H, t); 3.55~3.85 (4H, m); 3.05 (1H, m); 2.80 (1H, m); 2.56 (1H, m); 2.40 (1H, m); 2.00~2.30 (4H, m); 1.00~1.90 (10H, m).

Experimental Example 1

Neuroprotective Effect of Morphinan

Experimental Example 1.1

Animals and Drugs

All animals were treated in strict accordance with the NIH Guide for the Humane Care and Use of Laboratory Animals (NIH Guide for the Care and Use of Laboratory Animals, NIH Publication No. 85-23, 1985). Male C57BL/6 mice (Bio Genomics, Inc., Charles River Technology, Gapyung-Gun, Gyeonggi-Do, Korea) weighing about 30±3 g were maintained on a 12:12 h light:dark cycle and fed ad libitum. They were adapted for 2 weeks to the above conditions before carrying out the experiments. Dopaminergic neurotoxins used in this study were 1-methyl-4-phenyl-1,2,5,6-tetrahydropyridine (MPTP; Sigma, St. Louis, Mo.), lipoploysacchrade (LPS; Sigma Chem , St. Louis, Mo.), and methamphetamine (MA; NIDA/NIH, USA).

Male mice received daily MPTP injections (20 mg free base/kg, s.c.) for 7 consecutive days. Each morphinan was administered 30 min prior to every injection of MPTP for last three days (from day $4^{th}$ to day $7^{th}$). Animals were sacrificed 24 h after the last MPTP treatment.

Male mice were anesthetized with chloral hydrate (200 mg/kg, i.p.) and positioned in a small-animal stereotaxic apparatus. Injection of LPS into striatal region was made using the stereotaxic coordinates, measured from bregma (Franklin and Paxinos, 1997): +0.7 mm posterior, ±1.0 lateral, −3.4 ventral. LPS (2 μg in a volume of 2 μl of PBS) was injected into both sides of the striatum over a period of 2 min, and the injection needle was kept in place for 2 min after the injection. Control animals received striatal injection with PBS. Each morphinan was administered two times (4 h and 40 min, and 40 min) before intrastriatal injection with LPS (10, 28).

Because MA induced hyperthermia and neurotoxicity can be blocked by lowering the ambient temperature during the drug treatment (22, 29), the mice were housed in a temperature-controlled (22.0±0.5° C.) colony room, which was controlled at 50±5% humidity under filtered positive pressure ventilation on a 12-hr/12-hr dark cycle with diets and water ad libitum. Mice received four injections of MA hydrochloride (7.5 mg/kg, i.p. as a free base) at 2-hr intervals (22, 29). Colonic temperatures were recorded 60 min after each treatment. Colonic temperatures were measured using thermometer (Thermoscan, San Diego, Calif.). Animals were returned to the same home cage after final measurement of colonic temperature. Mice were sacrificed at 3 days after the final injection of MA (29). Each morphinan was administered two times, 4 h and 40 min, and 40 min before first MA treatment.

Experimental Example 1.2

Morphinans

All solutions were freshly made using distilled deionized water or saline. DM hydrobromide was obtained from Sigma Chemical Co. (St. Louis, Mo.). Dextrorphan (DX) tartrate, 3-allyloxy-17-methylmorphinan (AM) hydrobromide, 3-cyclopropylmethoxy-17-methylmorphinan (CM) hydrobromide, and 3-hydroxymorphinan (HM) hydrobromide (24), and dimemorfan (DF) phosphate were synthesized (38, 41, 46) (FIG. 1). Each compound was injected i.p. in a volume of 0.1 ml/10 g.

Experimental Example 1.3

Locomotor Activity and Locomotor Pattern

C57 BL/6 mice received each compound (20 or 40 mg/kg, i.p./day) once a day for 7 days. Ten min after the last treatment with each drug, locomotor activity was measured for 30 min. After measuring the locomotor activity (i.e. 40 min after the last drug injection), the 'absolute turn angular' was analyzed in a 3-min monitoring period using an automated video-tracking system (Noldus Information Technology, Wagenin, The Netherlands) to examine locomotor patterns. Locomotor facilitation at the borders (margins) of the test box was defined as marginal activity (circling behavior), respectively (13, 25, 27). Eight test boxes (40×40×30 cm high) were operated simultaneously by an IBM computer. Animals were studied individually during locomotion in each test box, where they were adapted for 10 min before starting the experiment. A printout for each session showed the pattern of the ambulatory movements of the test box. The distance traveled in cm by the animals in horizontal locomotor activity was analyzed (13, 25, 27). Data were collected and analyzed between 0900 and 1700 hr.

Experimental Example 1.4

Conditioned Place Preference (Psychological Dependence)

As a control, C57 BL/6 mice received an i.p. injection of saline just before entering the white or black compartment. Each compound (20 or 40 mg/kg, i.p.) dissolved in saline (0.1 ml/10 g) was administered immediately before the mice were placed in the white compartment (37).

On day 1, the mice were pre-exposed to the test apparatus for 5 min. The guillotine doors were raised and the mice were allowed to move freely between the two compartments. On day 2, the time each mouse spent in each compartment was recorded for 15 min. On days 3, 5, 7, 9, 11, and 13, the mice were injected with each drug before being confined to the white compartment, the non-preferred side, for 40 min. On days 4, 6, 8, 10, and 12, the mice were injected with saline before being confined to the black compartment, the preferred side, for 40 min. On day 14, the guillotine doors were raised. The mice were initially placed in the tunnel and the time spent by the mice in the two compartments was recorded for 15 min. The scores were calculated from the differences in the time spent in the white compartment in the testing and pre-testing phases (13, 27, 37). Data were analyzed between 0900 and 1700 hr.

Experimental Example 1.5

Determination of Dopamine and its Metabolites

Brains were rapidly removed and cut into 1 mm coronal sections on ice. The striatum was punched using a fine pasteur pipette (3, 21, 22), and stored at −70° C. DA and its metabolites, 3,4-dihydroxyphenylacetic acid (DOPAC) and homovanilic acid (HVA) were measured by HPLC-eletrochemical detection (3, 21, 22). Briefly, the striatum was homogenized in 0.2 M perchloric acid containing 3,4-dihydroxybenzylamine as an internal standard (10 mg wet weight of tissue per ml). The homogenate was centrifuged and a 20-µl aliquot of the supernatant was injected into the HPLC equipped with an ODS-$C_{18}$ column. The mobile phase was comprised of 26 ml of acetonitrile, 21 ml of tetrahydrofuran and 960 ml of 0.15 M monochloroacetic acid (pH 3.0) containing 50 mg/l of EDTA and 200 mg/l of sodium octyl sulfate. The amount of DA, DOPAC and HVA were determined by comparison of peak height ratio of tissue sample with standards, and were expressed in nanograms per 100 mg of wet weight of tissue.

Experimental Example 1.6

Immunocytochemistry

The coronal sections containing hippocampus were processed for tyrosine hydroxylase (TH) immunocytochemistry. Prior to overnight incubation with the primary antibody, sections were prewashed in 0.2% Triton X-100 for 15 min, followed by 4% normal goat serum for 20 min. After a 24 h incubation with the primary antiserum, sections were then incubated with a secondary biotinylated antiserum (1:800 dilution) for 1 h. Sections were always washed three times with PBS (pH 7.4) between each incubation step. The avidin-biotin complex method (ABC Kits, Vector Laboratories, Inc.) with 3,3'-diaminobenzidine tetrahydrochloride as the chromogen was used to visualize immunoreactive cells. The antibodies against TH (24-27, 49, 61) was diluted 2,000 times. Total neuronal population was corrected by the method of Abercrombie (1) under the image analysis system (Optimas version 6.2; Neurolucida program-contrast correcting system was included for normalizing in background signals) (3, 22).

Experimental Example 1.7

Statistics

The data were analyzed by Fischer LSD test, ANOVA with-Duncan's new multiple test and -with repeated measures. Statistical significance was defined as $p<0.05$.

Results

Experimental Example 1.8

Changes in Locomotor Activity Following Repeated Administration of Morphinans or Phencyclidine (PCP)

Figure 2:
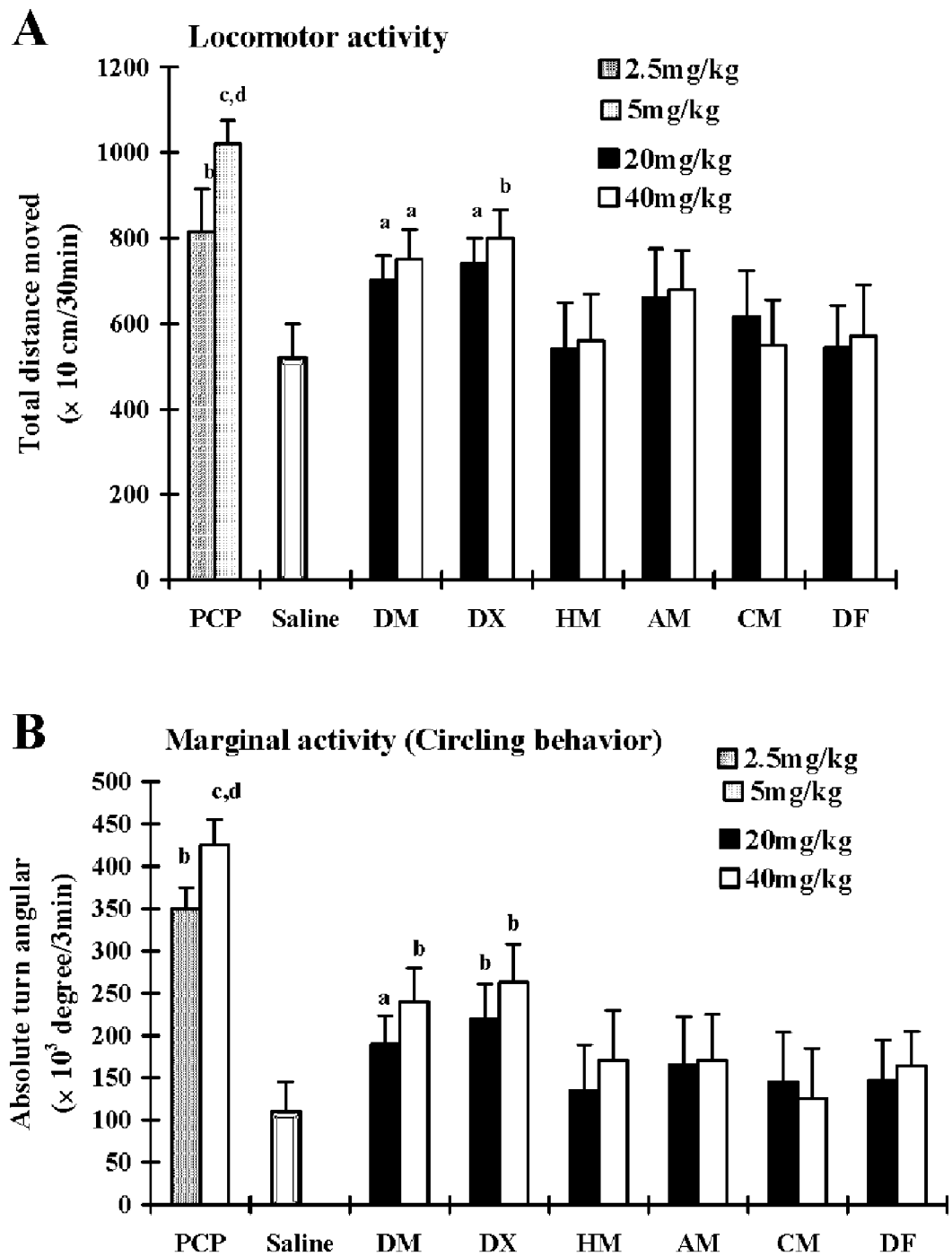
FIGS. 2A-2B show changes in locomotor activity following repeated administration of morphinan or phencyclidine (PCP). DM=dextromethorphan, DX=dextrorphan, HM=3-hydroxymorphinan, AM=3-allyloxy-17-methylmorphinan, CM=3-cyclopropylmethoxy-17-methylmorphinan, DF=dimemorfan. In 2A, 'total distance moved in cm' by the animals in the horizontal locomotor activity was measured for 30 min after final treatment. In 2B, after measuring locomotor activity, the 'absolute turn angular' parameter was analyzed in a 3-min monitoring period using an automated video tracking system in order to examine marginal activity (circling behavior). Each value is the mean±S.E.M. of 10 animals. $^{a}P<0.05$, $^{b}P<0.01$, $^{c}P<0.001$ vs. Saline, $^{d}P<0.05$ vs PCP 2.5 mg/kg (ANOVA with DMR test).
Figure 3:
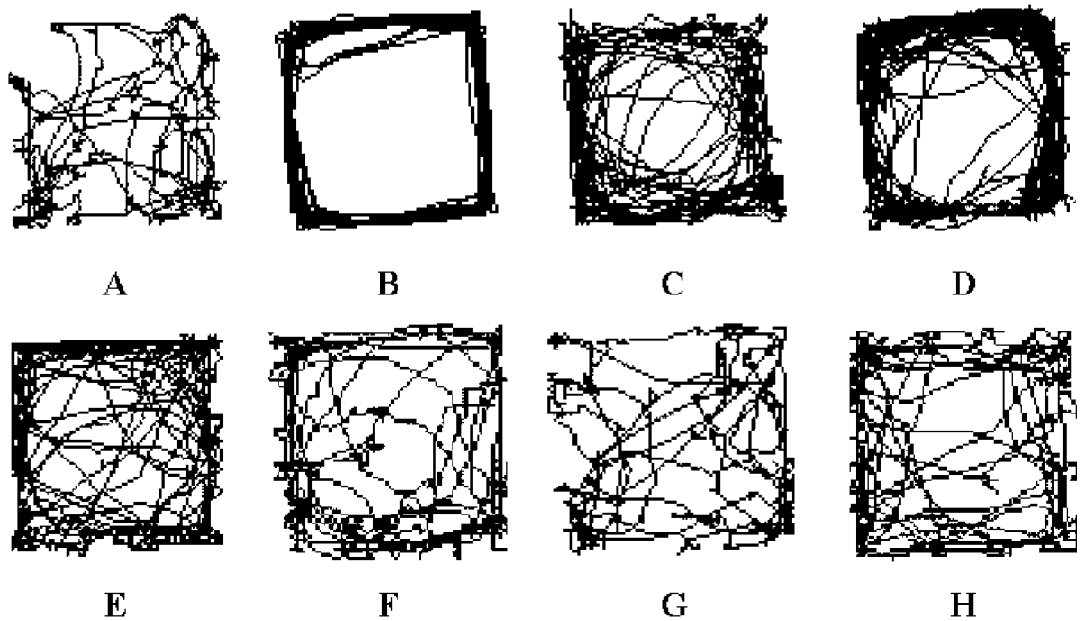
FIGS. 3A-3H show the tracings of a representative locomotor pattern; A. Saline injection, intraperitoneal (i.p.), B. Phencyclidine (PCP) 5 mg/kg, i.p., C. Dextromethorphan (DM) 40 mg/kg, i.p., D. Dextrorphan (DX) 40 mg/kg, i.p., E. 3-Hydroxy-morphinan (HM) 40 mg/kg, i.p., F. 3-Allyloxy-17-methylmorphinan (AM) 40 mg/kg, i.p., G. 3-Cyclopropylmethoxy-17-methylmorphinan (CM) 40 mg/kg, intrapentoneal (i.p.), H. Dimemorfan (DF) 40 mg/kg, i.p. Note the peculiar increase in the marginal activity (circling behavior) after treatments with PCP, DX or DM.
Figure 4:
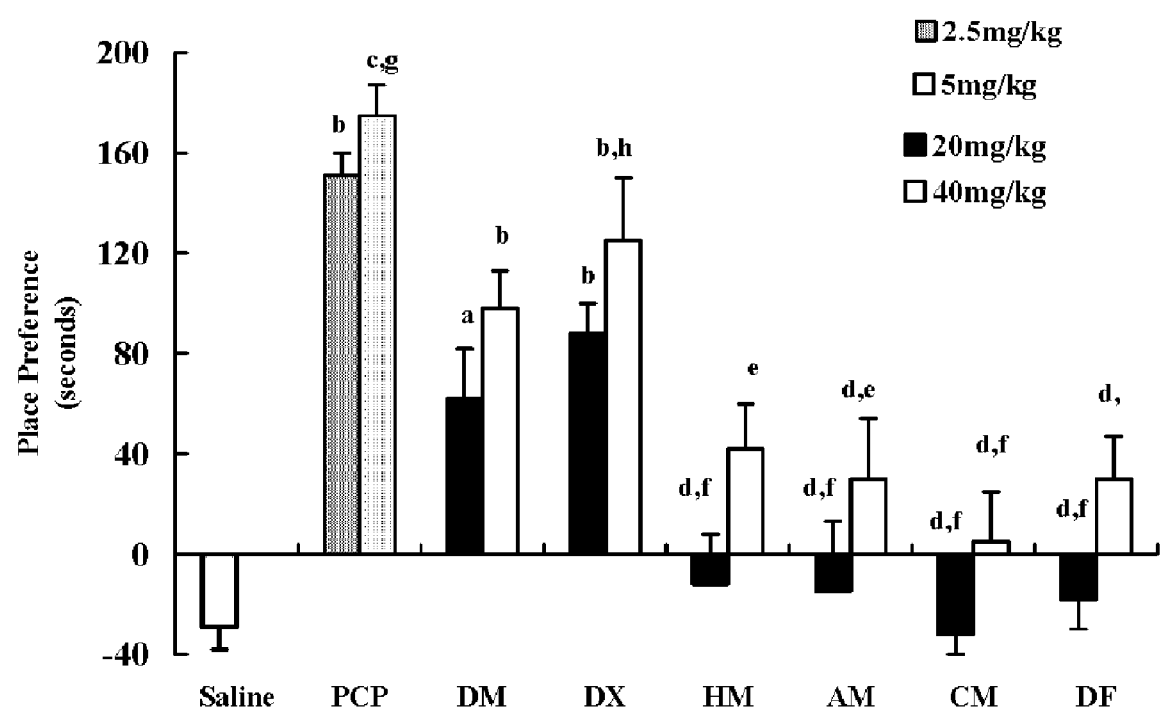
FIG. 4 shows changes in conditioned place preference (CPP) profile following repeated administration of morphinan or phencyclidine (PCP). DM=dextromethorphan, DX=dextrorphan, HM=3-hydroxymorphinan, AM=3-allyloxy-17-methylmorphinan, CM=3-cyclopropylmethoxy-17-methylmorphinan, DF=dimemorfan. Each value is the mean±S.E.M. of 15 animals. $^{a}P<0.05$, $^{b}P<0.01$, $^{c}P<0.001$ vs. Saline, $^{d}P<0.05$ vs corresponding dose of DM, $^{e}P<0.05$, $^{f}P<0.01$ vs. corresponding dose of DX, $^{g}P<0.05$ vs. PCP 2.5 mg/kg, $^{h}P<0.05$ vs. DX 20 mg/kg (ANOVA with DMR test).

The behavioral data are summarized in FIGS. 2-4. Saline-injected animals showed basal locomotor activity. Repeated administration of DX or DM (20 or 40 mg/kg) significantly increased locomotor activity. This effect appeared to be more pronounced in the animals treated with DX than in those treated with DM. The behavioural profile induced by DX is comparable to that of PCP. Although treatment with AM appeared to increase locomotor activity slightly, the locomotor activity following treatment with HM, CM or DF was comparable to that with saline (FIG. 2A). DX induced a significant increase in marginal activity (circling behaviour) in a dose-related manner (DX 20 or 40 mg/kg vs. saline, p<0.01). The behavioral effect induced by DX was similar to that of PCP (PCP 2.5 vs. 5.0 mg/kg, p<0.05). In contrast, DM also induced a significant increase in marginal activity (DM 20 or 40 mg/kg vs. saline, p<0.05). However, HM, AM, CM, and DF did not significantly affect marginal activity versus the saline group (FIG. 2B). PCP produced much stronger stereotypies (i.e. circling behaviors≈marginal activities) than seen in any other group (FIGS. 2A and B).

Saline-treated animals did not show any significant locomotor pattern. The locomotor patterns were significantly altered after treatment with PCP, DM, and DX. PCP, DM, and DX produced marginal activity (circling behaviour). By contrast, HM, AM, CM and DF did not produce significant marginal activity in any locomotor pattern (FIG. 3).

Experimental Example 1.9

Changes of Conditioned Place Preference (CPP) Profile Following Repeated Administration of Morphinans or Phencyclidine (PCP)

The saline-treated animals did not show any CPP effects. DX-treated animals produced CPP in a dose-dependent manner (DX 20 or 40 mg/kg vs. saline, p<0.01; DX 20 vs. 40 mg/kg, p<0.05). As with DX, treatment with DM also produced CPP (DM 20 mg/kg vs. saline, p<0.05; DM 40 mg/kg vs. saline, p<0.01). The most significant CPP followed PCP (PCP 5 mg/kg vs. saline, p<0.001; PCP 2.5 vs. 5.0 mg/kg, p<0.05). By contrast, HM, CM, AM and DF-treated animals showed almost no CPP effects compared with saline-treated animals (FIG. 4).

Experimental Example 1.10

Figure 5:
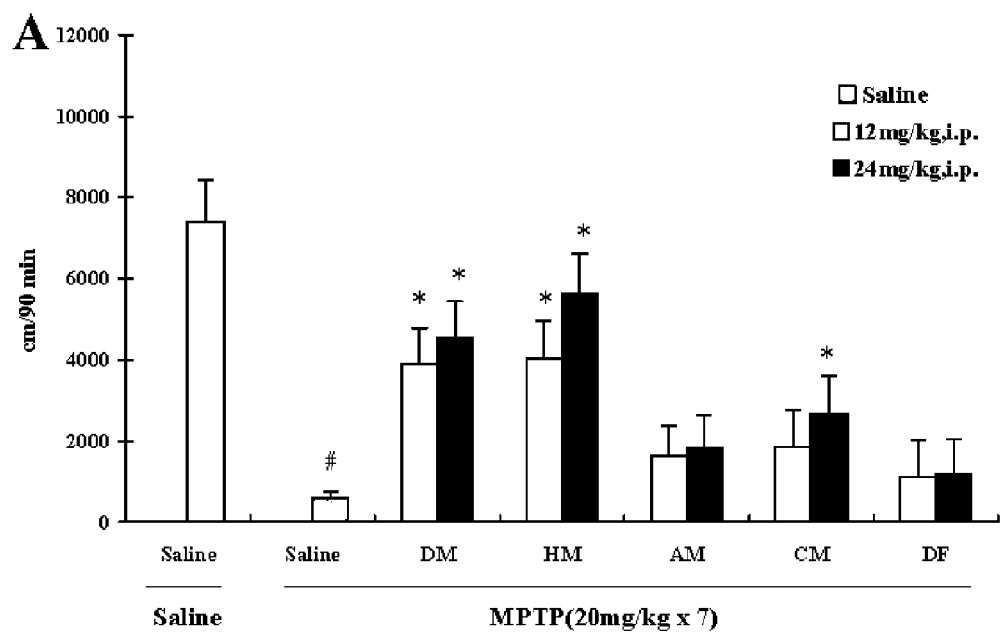
FIGS. 5A-5B show effects of morphinan analogs on the locomotor activity (A) and locomotor pattern (B) induced by MPTP in mice. Each value is the mean±S.E.M. of 10 animals (A). $^{\#}P<0.01$ vs. Saline+Saline, *P<0.01 vs. Saline+MPTP. A significant reduction in locomotor activity/pattern in the animals treated with MPTP, is significantly increased in the presence of HM or DM. This attenuation is more pronounced in the animal treated with HM.
Figure 5:
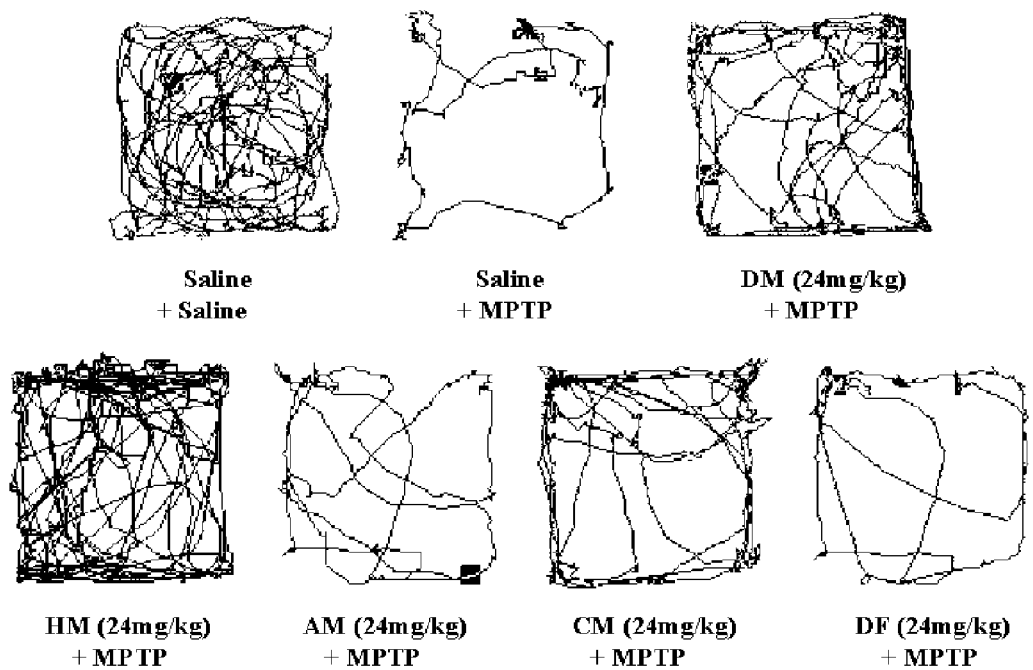

Effects of Morphinans on Hypokinesia (Reduction in Locomotor Activity) and Dopamine Loss Induced by MPTP Repeated treatment with MPTP (20 mg/kg/day×7) significantly reduced locomotor activity (Saline+Saline vs. Saline+MPTP, P<0.01). Pretreatment with CM (Saline+MPTP vs. CM 24 mg/kg+MPTP, P<0.05), DM (Saline+MPTP vs. DM 12 or 24 mg/kg+MPTP, P<0.01) or HM (Saline+MPTP vs. HM 12 or 24 mg/kg+MPTP, P<0.01) significantly prevented MPTP-induced reduction in locomotor activity (FIG. 5A). Their behavioral effects were consistent with their locomotor patterns (FIG. 5B). However, neither AM nor DF affected significantly the locomotor hypoactivity induced by MPTP.

The levels of DA, DOPAC and HVA in the striatum from mice treated with MPTP is presented in Table 1. No significant difference was observed in the animals that did not receive MPTP. MPTP treatment significantly decreased DA (P<0.01), DOPAC (P<0.01) and HVA (P<0.01); these reductions were significantly protected by pretreatment with DM (24 mg/kg; DA; P<0.05, DOPAC; P<0.05, HVA; P<0.05), HM (24 mg/kg) (DA; P<0.01, DOPAC; P<0.01, HVA; P<0.01) or CM (DA; P<0.05, DOPAC; P<0.05, HVA; P<0.05). However, AM and DF did not alter reductions in DA, DOPAC and HVA induced by MPTP.

TABLE 1

Contents of dopamine (DA), 3,4-dihydroxyphenylacetic acid (DOPAC), and homovanillic acid (HVA) in the striatum from 1-methyl-4-phenyl-1,2,3,6-tetrahydropyridine (MPTP)-treated mice with or without morphinans.

| Compound | Concentration (ng/100 mg wet tissue) DA | Concentration (ng/100 mg wet tissue) DOPAC | Concentration (ng/100 mg wet tissue) HVA |
|---|---|---|---|
| Saline + Saline | 1110 ± 116 | 152 ± 14 | 123 ± 14 |
| Saline + MPTP | 398 ± 45$^a$ | 46 ± 7$^a$ | 54 ± 6$^a$ |
| DM 12 + MPTP | 520 ± 67 | 69 ± 9 | 82 ± 9 |
| DM 24 + MPTP | 708 ± 82$^b$ | 85 ± 10$^b$ | 98 ± 11$^b$ |
| HM 12 + MPTP | 582 ± 74 | 68 ± 7 | 84 ± 8 |
| HM 24 + MPTP | 896 ± 79$^c$ | 98 ± 9$^c$ | 104 ± 10$^c$ |
| AM 12 + MPTP | 468 ± 52 | 54 ± 6 | 69 ± 5 |
| AM 24 + MPTP | 539 ± 64 | 66 ± 8 | 78 ± 7 |
| CM 12 + MPTP | 489 ± 69 | 58 ± 6 | 68 ± 9 |
| CM 24 + MPTP | 587 ± 76$^b$ | 78 ± 10$^b$ | 89 ± 7$^b$ |
| DF 12 + MPTP | 403 ± 55 | 44 ± 6 | 62 ± 7 |
| DF 24 + MPTP | 397 ± 55 | 52 ± 7 | 68 ± 6 |

Male mice that received daily MPTP injections (20 mg/kg, s.c.) for 7 consecutive days. Each morphinan was administered 30 min before every injection of MPTP for last three days. Animals were sacrificed at 24 h after the last MPTP injection. Each value is the mean±S.E.M. of 8 animals. $^a$P<0.01 vs. Sal+Sal, $^b$P<0.05 vs. Sal+MPTP, $^c$P<0.01 vs. Sal+MPTP (ANOVA with DMR test).

Figure 6:
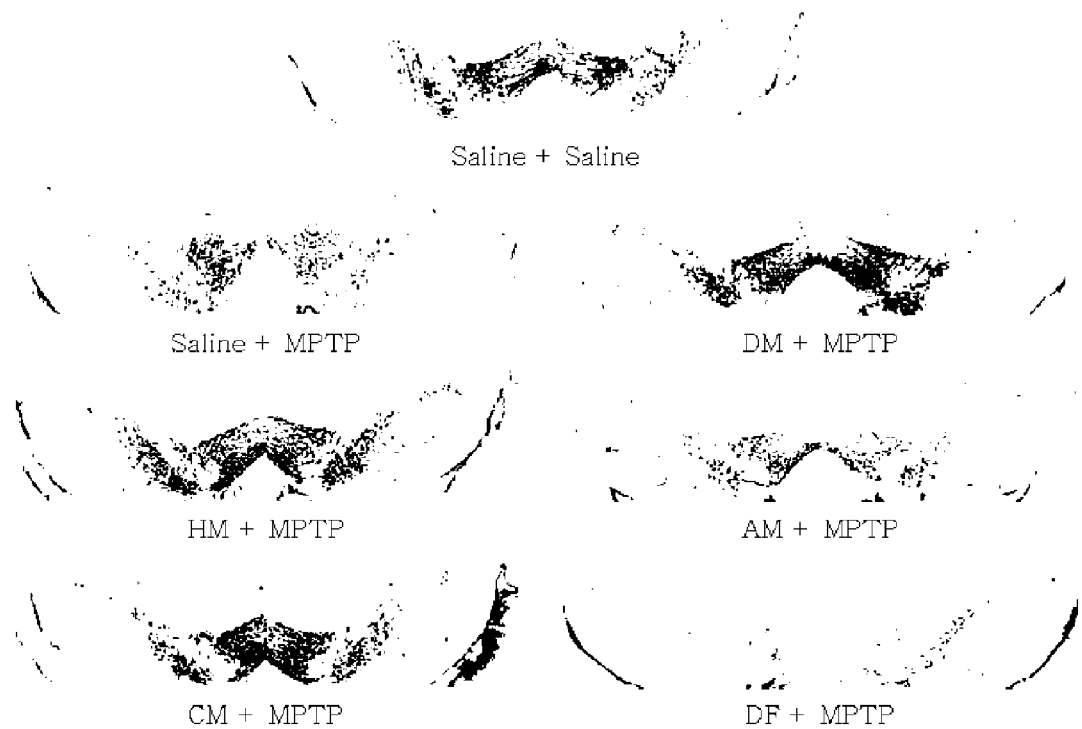
FIGS. 6A-6B. 6A shows effects of morphinan analogs (24 mg/kg, i.p.) on the tyrosine hydroxylase-like immunoreactivities (TH-IR) in the substantia nigra (SN) dopaminergic neurons from mice treated with MPTP. Magnification=40×. In 6B, each value is the mean±S.E.M. of 5 animals. Total numbers of the TH-positive neurons throughout the SN pars compacta were counted. TH-positive neurons with clearly stained somata were identified and counted using a microscope equipped with graded eyepiece. Total neuronal number was corrected for section thickness by the method of Abercrombie (1) under image analysis system (Optimas version 6.2). $^{\#}P<0.01$ vs. Saline+Saline, *P<0.05 vs. Saline+MPTP (Fischer LSD test).
Figure 6:
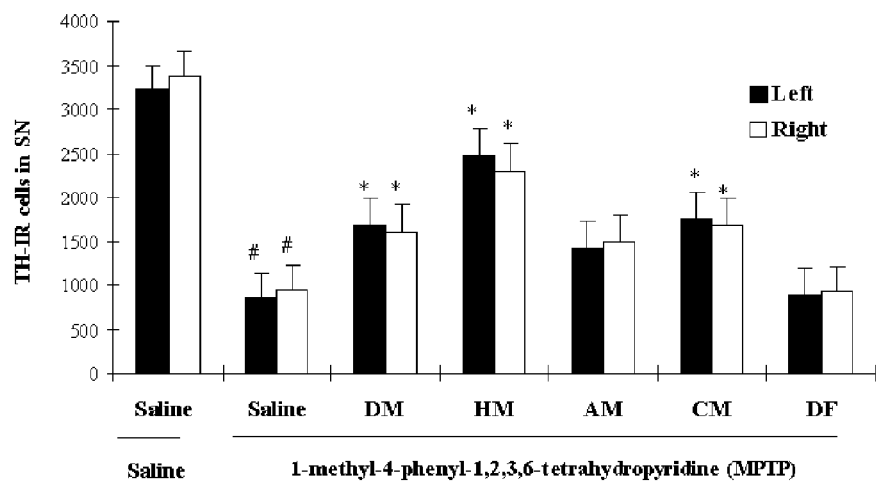

The TH-like immunoreactivities (TH-IR) as influenced by MPTP treatment in combination with morphinans are shown in FIG. 6. Each animal receiving saline exhibited well-preserved TH-IR. Treatment with MPTP significantly decreased (P<0.01) the number of TH-positive cells. Pretreatment with HM (24 mg/kg) (P<0.05) DM (24 mg/kg) (P<0.05) or CM (24 mg/kg) (P<0.05) significantly attenuated the decrease in TH-positive cells induced by MPTP. The results show that the DA levels in the striatum are consistent with the TH-IR in the SN following treatment with MPTP.

Experimental Example 1.11

Effects of Morphinans on Hypokinesia (Reduction in Locomotor Activity) and Dopamine Loss Induced by Lipopolysaccharide (LPS)

Figure 7:
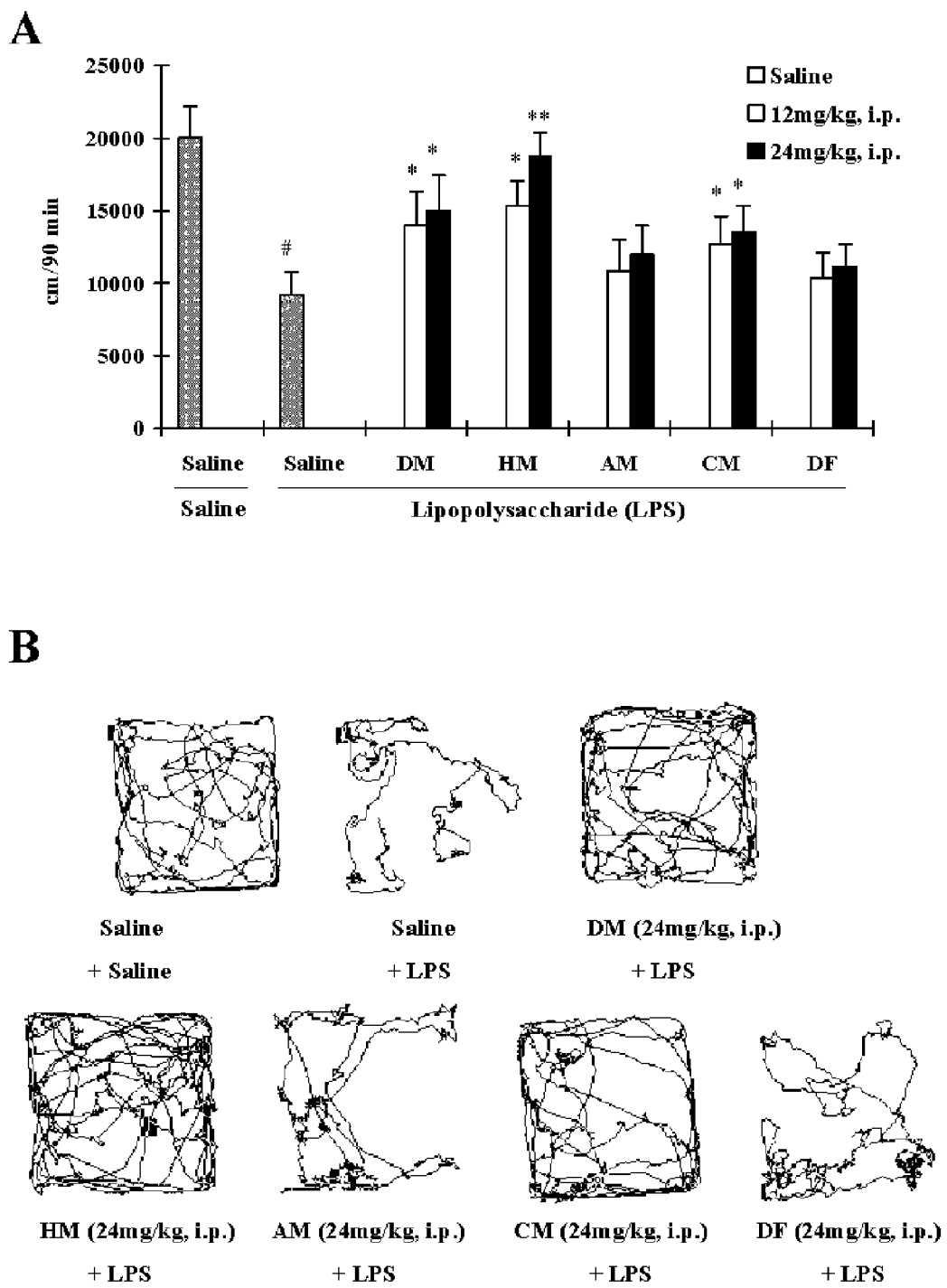
FIGS. 7A-7B show effects of morphinan analogs on the locomotor activity (A) and locomotor pattern (B) induced by LPS in mice. Each value is the mean±S.E.M. of 10 animals (A). $^{\#}P<0.01$ vs. Saline+Saline, *P<0.05 vs. Saline+LPS, **P<0.01 vs. Saline+LPS. A significant reduction in locomotor activity/pattern in the animals treated with LPS, is significantly increased in the presence of HM or DM. The attenuation is more pronounced in the animal treated with HM.

Bilateral intrastriatal injection of LPS (20 μg×2) significantly reduced locomotor activity (Saline+Saline vs. Saline+LPS, P<0.01). Pretreatment with CM (Saline+LPS vs. CM 12 or 24 mg/kg+LPS, P<0.05), DM (Saline+LPS vs. DM 12 or 24 mg/kg+LPS, P<0.05) or HM (Saline+LPS vs. HM 12 or 24 mg/kg+LPS, P<0.05 or P<0.01) significantly prevented LPS-induced decrease in locomotor activity (FIG. 7A). These behavioral effects paralleled their locomotor patterns (FIG. 7B). However, neither AM nor DF were effective in attenuating locomotor hypoactivity induced by LPS.

The levels of DA, DOPAC and HVA in the striatum from mice treated with LPS is presented in Table 2. No significant difference is observed among the animals in the absence of LPS. Intrastriatal injection with LPS significantly decreased DA (P<0.01), DOPAC (P<0.01) and HVA (P<0.01); these reductions were significantly protected by pretreatment with DM (24 mg/kg; DA; P<0.01, DOPAC; P<0.02, HVA; P<0.02), HM (24 mg/kg) (DA; P<0.01, DOPAC; P<0.01, HVA; P<0.02) or CM (24 mg/kg) (DA; P<0.05, DOPAC; P<0.05, HVA; P<0.05). However, AM and DF did not alter LPS-induced reductions in DA, DOPAC and HVA levels.

TABLE 2

Contents of dopamine (DA), 3,4-dihydroxyphenylacetic acid (DOPAC), and homovanillic acid (HVA) in the striatum from lipopolysaccharide (LPS)-treated mice with or without morphinans.

| Compound | Concentration (ng/100 mg wet tissue) DA | Concentration (ng/100 mg wet tissue) DOPAC | Concentration (ng/100 mg wet tissue) HVA |
|---|---|---|---|
| Saline + Saline | 1012 ± 123 | 149 ± 16 | 128 ± 12 |
| Saline + LPS | 448 ± 45$^a$ | 47 ± 5$^a$ | 58 ± 7$^a$ |
| DM 12 + LPS | 612 ± 76 | 68 ± 7 | 82 ± 9 |
| DM 24 + LPS | 892 ± 92$^d$ | 105 ± 12$^b$ | 98 ± 8$^b$ |
| HM 12 + LPS | 682 ± 70 | 83 ± 10 | 86 ± 8 |
| HM 24 + LPS | 916 ± 98$^d$ | 112 ± 11$^d$ | 102 ± 10$^b$ |
| AM 12 + LPS | 454 ± 55 | 64 ± 8 | 75 ± 6 |
| AM 24 + LPS | 452 ± 49 | 66 ± 7 | 70 ± 8 |
| CM 12 + LPS | 482 ± 54 | 70 ± 7 | 83 ± 6 |
| CM 24 + LPS | 684 ± 56$^c$ | 86 ± 9$^c$ | 89 ± 7$^c$ |
| DF 12 + LPS | 635 ± 65 | 54 ± 7 | 62 ± 8 |
| DF 24 + LPS | 459 ± 58 | 59 ± 8 | 63 ± 7 |

Injection of LPS into striatal region was made using the stereotoxic coordinates, measured from bregma: +0.7 mm posterior, ±1.0 mm laterior, −3.4 mm ventral. LPS (2 μg in a volume of 2 μl of PBS) was injected to both sides of striatum. Each morphinan was administered two times, 4 h and 40 min, and 40 min before intrastriatal injection with LPS. Mice were sacrificed at 3 weeks after LPS treatment. Each value is the mean±S.E.M. of 8 animals. $^a$P<0.01 vs. Sal+Sal, $^b$P<0.02 vs. Sal+LPS, $^c$P<0.05 vs. Sal+LPS, $^d$P<0.01 vs. Sal+LPS (ANOVA with DMR test).

Figure 8:
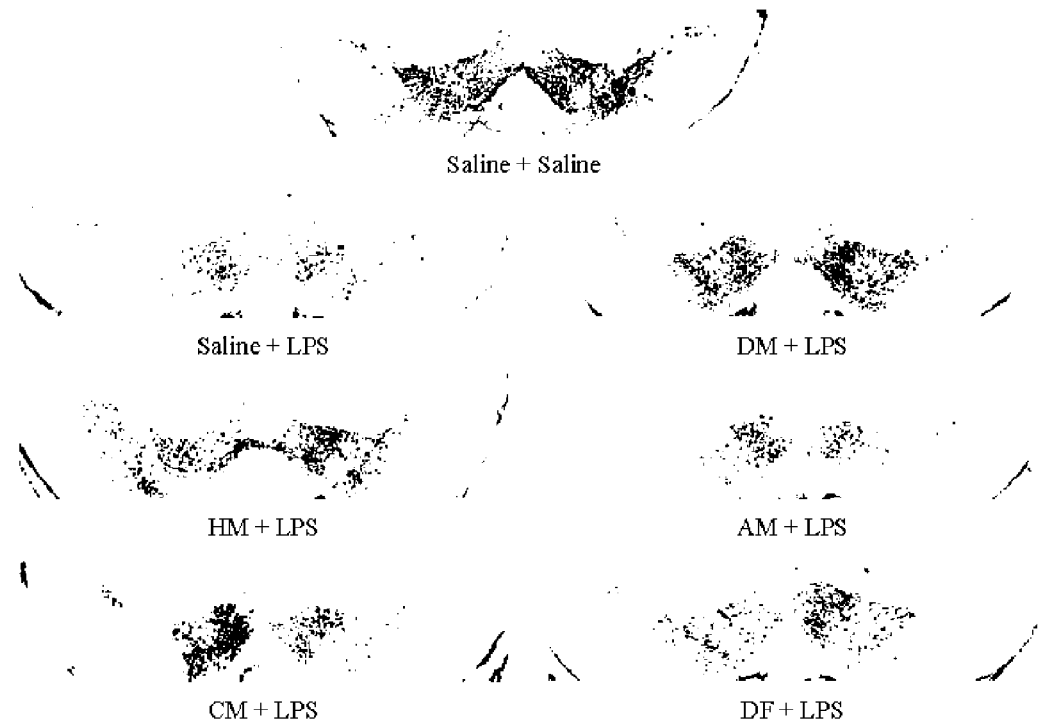
FIGS. 8A-8B. 8A shows effects of morphinan analogs (24 mg/kg, i.p.) on the tyrosine hydroxylase-like immunoreactivities (TH-IR) in the substantia nigra (SN) dopaminergic neurons from mice treated with LPS. Magnification=40×. In 8B, each value is the mean±S.E.M. of 5 animals. Total numbers of the TH-positive neurons throughout the SN pars compacta were counted. TH-positive neurons with clearly stained somata were identified and counted using a microscope equipped with graded eyepiece. Total neuronal number was corrected for section thickness by the method of Abercrombie (1) under image analysis system (Optimas version 6.2). $^{\#}P<0.01$ vs. Saline+Saline, *P<0.05 vs. Saline+MPTP, (Fischer LSD test).
Figure 8:
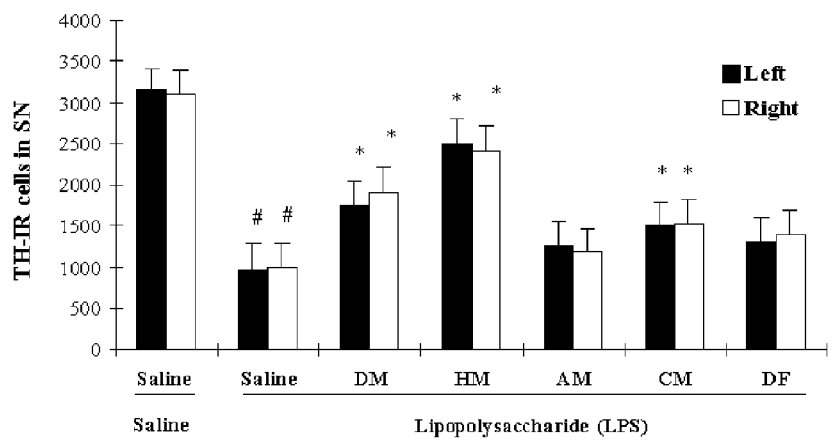
Figure 9:
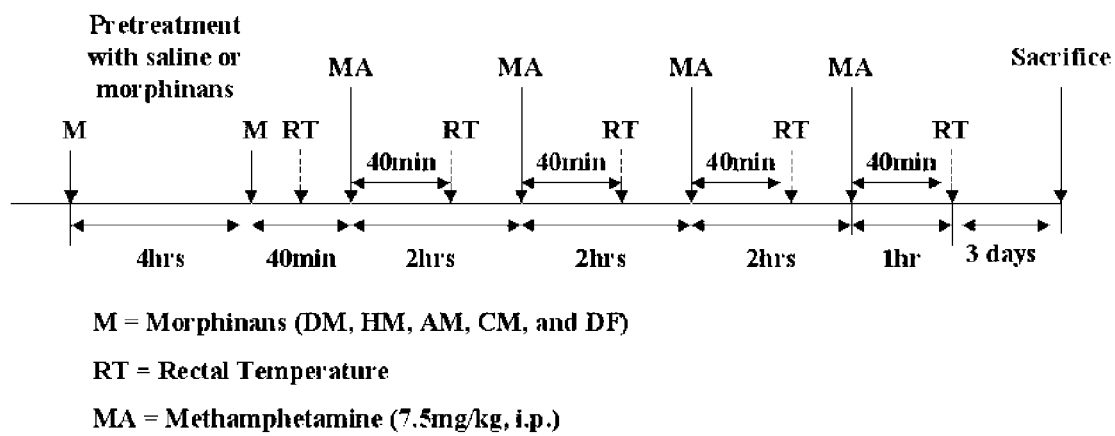
FIG. 9 shows experimental schedule for methamphetamine (MA) study. Mice received 4 injections of MA.HCl (7.5 mg/kg, i.p. as a free base) at 2 hr intervals. Rectal temperature was recorded at 40 min after each MA treatment. Each morphinan was administered two times, 4 h and 40 min, and 40 min before first MA injection. Mice were sacrificed at 3 days after final MA injection.

The TH-like immunoreactivities (TH-IR) following LPS treatment with or without morphinans are shown in FIG. 8. Each animal receiving saline or morphinan alone showed well-preserved TH-IR. Treatment with LPS significantly decreased (P<0.01) the number of TH-positive cells. Pretreatment with HM (24 mg/kg) (P<0.05), DM (24 mg/kg) (P<0.05) or CM (24 mg/kg) (P<0.05) significantly attenuated the reduction in TH-positive cells caused by administering LPS. The results show that the DA levels in the striatum correspond with the nigral TH-IR following treatment with LPS.

Experimental Example 1.12

Effects of Morphinans on Hyperthermia, Hypokinesia, and Dopamine (DA) Loss Induced by Methamphetamine (MA)

Figure 10:
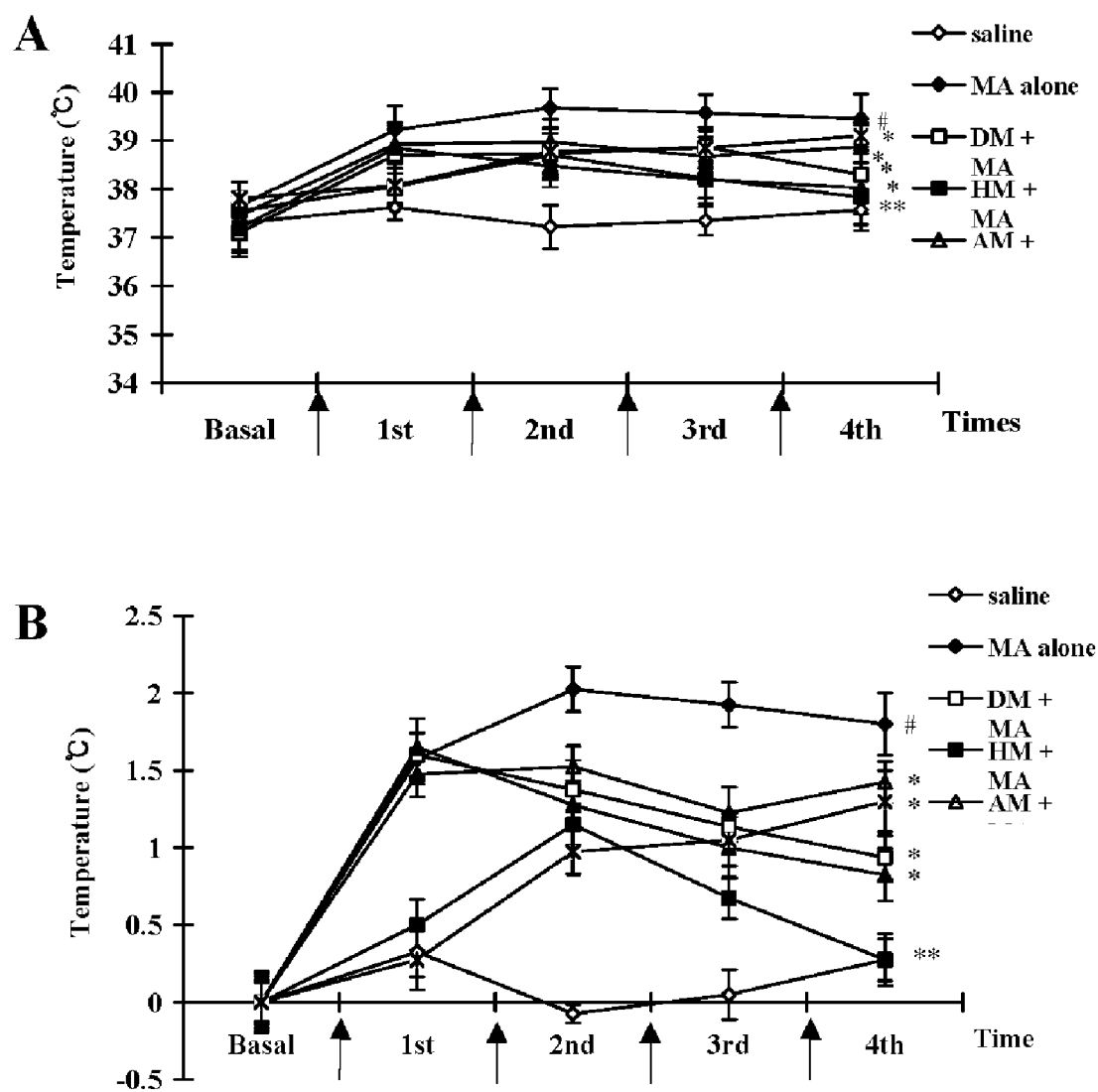
FIGS. 10A-10B show effect of morphinans on the methamphetamine (MA)-induced hyperthermia. Mice received i.p. injections of MA (four injections of 7.5 mg/kg each) at 2-h intervals under the ambient temperature of 22.0±0.5° C. Temperatures were recorded at 40 min after each MA treatment (Arrow=MA injection). HM was the most effective in attenuating MA-induced hyperthermia. Each value is the mean±S.E.M. of 12 animals. #$P<0.01$ vs. Saline, *$P<0.05$ vs. MA alone, **$P<0.01$ vs. MA alone (ANOVA for repeated measures).

It is well recognized that dopaminergic toxicity after MA treatment is linked to MA-induced hyperthermia. MA-induced hyperthermia (as measured by rectal temperature, Saline vs. MA, P<0.01) is attenuated by all morphinans used in this study. HM is the most efficacious (MA alone vs. 24 mg/kg HM+MA, P<0.01) among the five morphinans (MA alone vs. 24 mg/kg of DM, AM, CM or DF+MA, P<0.05) in attenuating hyperthermia induced by MA (FIG. 10).

Figure 11:
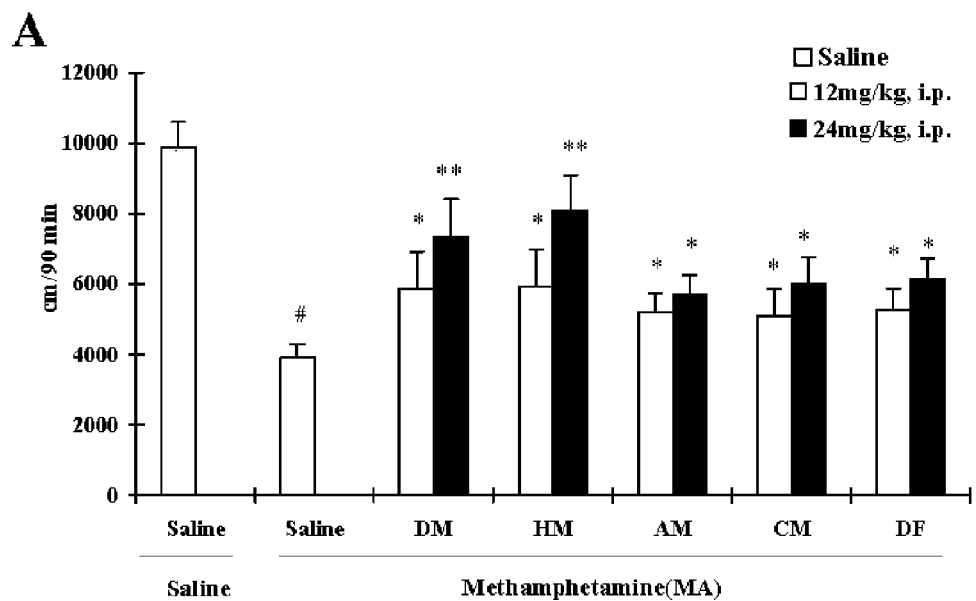
FIGS. 11A-11B show effects of morphinan analogs on the locomotor activity (A) and locomotor pattern (B) induced by methamphetamine (MA) in mice. Each value is the mean±S.E.M. of 10 animals (A). #$P<0.01$ vs. Saline+Saline, *$P<0.01$ vs. Saline+MA. A significant reduction in locomotor activity/pattern in the animals treated with MA, is significantly increased in the presence of HM or DM. The attenuation is more pronounced in the animal treated with HM.
Figure 11:
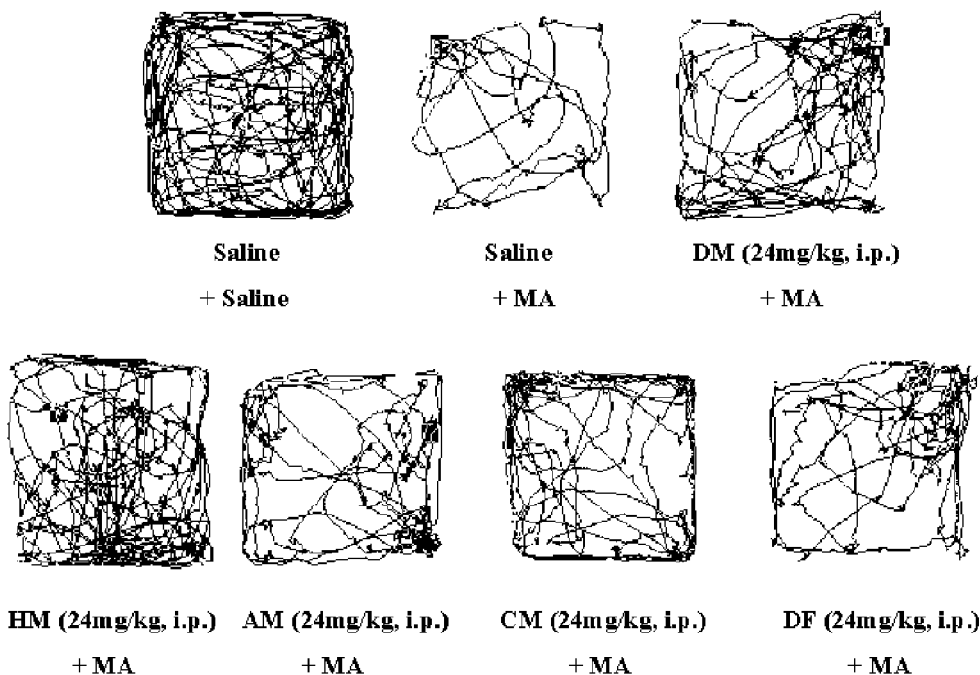

A significantly reduced locomotor activity (Saline+Saline vs. Saline+MA, P<0.01) was observed at 3 days after final treatment with MA (7.5 mg/kg×4, in a two hour's interval). Pretreatment with morphinans significantly prevented MA-induced reduction in locomotor activity (FIG. 11A). Their behavioral effects were consistent with their locomotor patterns (FIG. 11B). HM appeared to be the most effective in preventing reduction in motor activity after MA treatment (MA alone vs. 12 and 24 mg/kg of DM (P<0.05 and P<0.01), HM (P<0.05 and P<0.01), AM (P<0.05), CM (P<0.05), and DF (P<0.05)). The pharmacological effects of DM are comparable to those of HM.

The levels of DA, DOPAC and HVA in the striatum from mice treated with MA are presented in Table 3. No significant differences were observed among the animals that were not administered MA levels. MA treatment significantly decreased DA (P<0.01), DOPAC (P<0.01) and HVA (P<0.01); these reductions were significantly protected by pretreatment with DM (24 mg/kg; DA; P<0.02, DOPAC; P<0.05, HVA; P<0.05), HM (24 mg/kg) (DA; P<0.01, DOPAC; P<0.01, HVA; P<0.02), AM (24 mg/kg; DA; P<0.05, DOPAC; P<0.05, HVA; P<0.05), CM (24 mg/kg; DA; P<0.02, DOPAC; P<0.05, HVA; P<0.05) or DF (24 mg/kg; DA; P<0.05, DOPAC; P<0.05, HVA; P<0.05).

TABLE 3

Contents of dopamine (DA), 3,4-dihydroxyphenylacetic acid (DOPAC), and homovanillic acid (HVA) in the striatum from methamphetamine (MA)-treated mice with or without morphinans.

| Compound | Concentration (ng/100 mg wet tissue) DA | Concentration (ng/100 mg wet tissue) DOPAC | Concentration (ng/100 mg wet tissue) HVA |
|---|---|---|---|
| Saline + Saline | 1104 ± 120 | 142 ± 16 | 122 ± 12 |
| Saline + MA | 469 ± 45$^a$ | 57 ± 6$^a$ | 54 ± 7$^a$ |
| DM 12 + MA | 625 ± 74 | 83 ± 9 | 82 ± 9 |
| DM 24 + MA | 782 ± 72$^c$ | 98 ± 11$^b$ | 94 ± 8$^b$ |
| HM 12 + MA | 685 ± 64 | 88 ± 10 | 82 ± 8 |
| HM 24 + MA | 864 ± 82$^d$ | 103 ± 9$^d$ | 100 ± 11$^c$ |
| AM 12 + MA | 601 ± 62 | 89 ± 9 | 79 ± 9 |
| AM 24 + MA | 749 ± 64$^b$ | 96 ± 10$^b$ | 92 ± 10$^b$ |
| CM 12 + MA | 668 ± 81 | 82 ± 10 | 83 ± 9 |
| CM 24 + MA | 777 ± 66$^c$ | 99 ± 10$^b$ | 94 ± 12$^b$ |
| DF 12 + MA | 603 ± 65 | 79 ± 11 | 79 ± 7 |
| DF 24 + MA | 762 ± 81$^b$ | 94 ± 9$^b$ | 92 ± 10$^b$ |

Male mice received 4 injections of MA-HCl (7.5 mg/kg, i.p. as a free base) at 2 hr intervals. Each morphinan was administered two times, 4 h and 40 min, and 40 min before first MA injection. Mice were sacrificed at 3 days after final MA injection. Each value is the mean±S.E.M. of 8 animals. $^a$P<0.01 vs. Sal+Sal, $^b$P<0.05 vs. Sal+MA, $^c$P<0.02 vs. Sal+MA $^d$P<0.01 vs. Sal+MA (ANOVA with DMR test).

Figure 12:
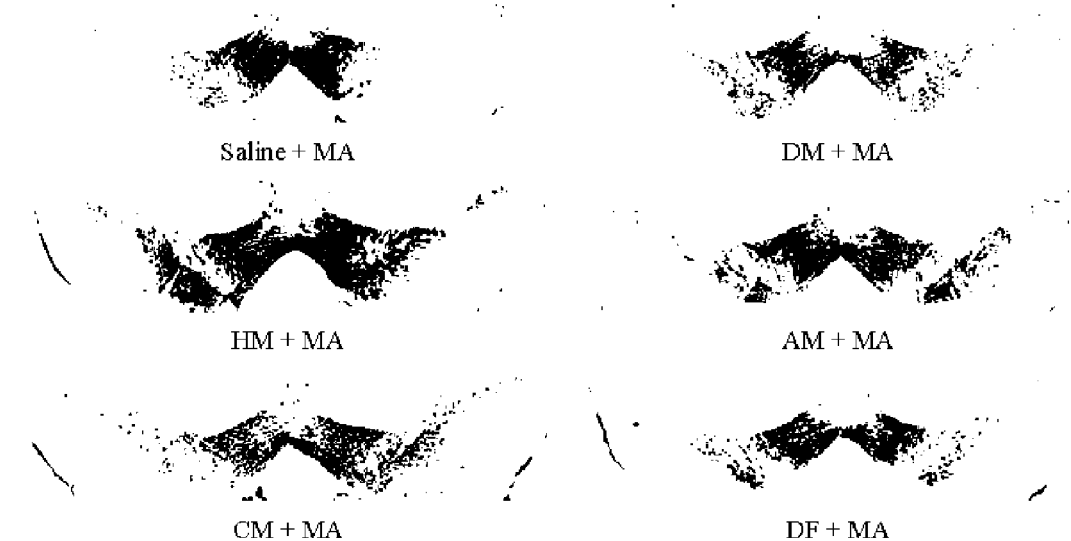
FIGS. 12A-12B show effects of morphinan analogs (24 mg/kg, i.p.) on the tyrosine hydroxylase-like immunoreactivities (TH-IR) in the substantia nigra (SN) dopaminergic neurons from mice treated with methamphetamine (MA). Magnification=40×. In 12B, each value is the mean±S.E.M. of 5 animals. Total numbers of the TH-positive neurons throughout the SN pars compacta were counted. TH-positive neurons with clearly stained somata were identified and counted using a microscope equipped with graded eyepiece. Total neuronal number was corrected for section thickness by the method of Abercrombie (1) under image analysis system (Optimas version 6.2). #$P<0.01$ vs. Saline+Saline, *$P<0.05$ vs. Saline+MA (Fischer LSD test).
Figure 12:
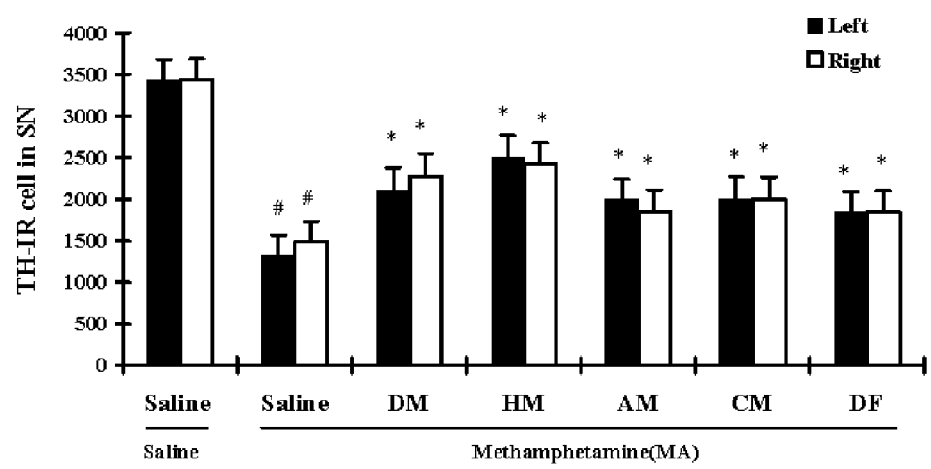

The nigral TH-like immunoreactivities (TH-IR) following MA treatment with or without morphinans are shown in FIG. 12. Each animal receiving saline or each morphinan alone exhibited well-preserved TH-IR. Treatment with MA significantly decreased (P<0.01) the number of TH-positive cells. Pretreatment with HM (24 mg/kg) (P<0.05), DM (24 mg/kg) (P<0.05), AM (24 mg/kg) (P<0.05), CM, (24 mg/kg) (P<0.05), and DF (24 mg/kg) (P<0.05) significantly attenuated the decrease in TH-positive cells induced by MA. Consistently, the results show that the striatal DA levels are consistent with the nigral TH-IR following treatment with MA in the presence of or in the absence of morphinans.

Experimental Example 2

Effect of Morphinan on Cannabinoid CB1 Receptor

Experimental Example 2.1

Figure 13:
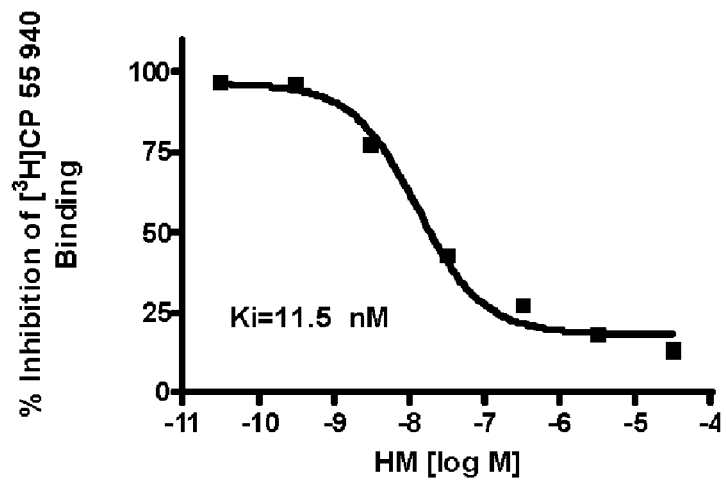
FIG. 13 shows displacement of specific binding of [3H]CP 55,940, a CB1 receptor agonist, in rat cerebral cortex membranes. Each value denotes the mean of 3 independent experiments.
Figure 14:
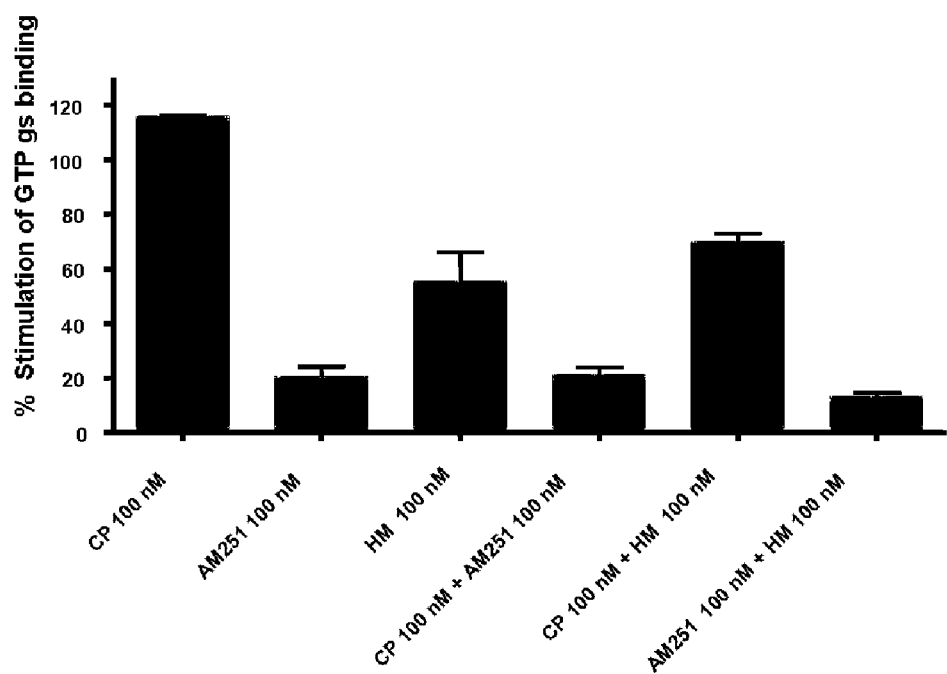
FIG. 14 shows CB1 antagonistic property (a partial agonist) of HM (3-hydroxymorphinan). CP=CP 55,940, a selective CB1 agonist, AM-251=a selective CB1 antagonist.

HM has a High Affinity for Cannabinoid CB1 Site, and Possesses a CB1 Receptor Antagonistic Property Since recent investigation has suggested that blockade of cannabinoid CB1 receptor shows beneficial effects in response to Parkinsonian model, it was examined whether 3-hydroxymorphinan (HM), which is the most efficacious morphinan on dopaminergic damage among dextrorotatory morphinans that were examined, exhibited a high affinity for the cannabinoid CB1 site. HM has a high affinity (Ki=11.5 nM) for the cannabinoid CB1 site (FIG. 13) and HM possesses CB1 receptor antagonistic properties. A selective CB1 agonist, CP55,940 [1α, 2β-(R)-5α]-(−)-5-(1,1-dimethyl)-2-[5-hydroxy-2-(3-hydroxypropyl)cyclohexyl-phenol] 100 nM significantly stimulated GTP γS binding by about 120%, while a selective CB1 antagonist, AM251 100 nM, inhibited its binding by approximately 20%. CP 55940-induced stimulation in GTP γS binding was significantly attenuated in the presence of AM 251 [N-(piperidin-1-yl)-5-(4-iodophenyl)-(2,4-dichlorophenyl)-4-methyl-1H-pyrazole-3-carboxamide]. HM 100 nM inhibited this binding by about 60%. CP 55940-induced increased binding was decreased by the treatment with HM. AM 251 decreased by about one third HM-induced binding. Thus, HM is a partial agonist of CB1 receptor, as well as a CB1 antagonist (FIG. 14).

Experimental Example 2.2

Figure 15:
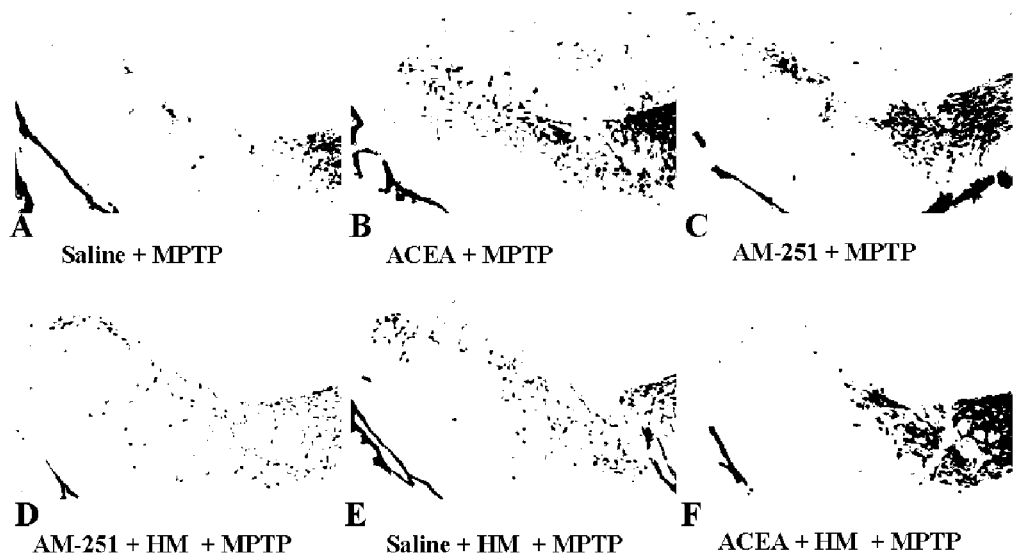
FIGS. 15A-15F show representative photographs of substantia nigra immunostained with tyrosine hydroxylase at 1 week after last MPTP administration in the substantia nigra. Neuroprotective effect of HM was counteracted by ACEA, a CB1 agonist. CB1 agonist or antagonist was administered 45 min before every MPTP, while HM was injected 30 min before every MPTP (20 mg/kg, i.p./day×7). Compounds were administered for 7 days post-final MPTP. Magnification=40×.

HM Attenuates MPTP-induced Reduced Tyrosine Hydroxylase-like Immunoreactivity (TH-IR) in Substantia Nigra of the Mice One day after final treatment with MPTP (20 mg/kg, i.p./day×7) a significant reduction of TH-IR is seen. This reduction of TH-IR was attenuated by the treatment with AM 251. Combined treatment with AM-251 (0.3 mg/kg, i.p.) and HM (20 mg/kg, i.p.) was more effective than treatment solely with AM-251 in response to MPTP-induced loss in TH-IR. The effect of this combination is equipotent to that of HM alone against MPTP. However, ACEA (arachidonyl-2-chloroethylamide) (2 mg/kg, i.p.) counteracted HM's neuroprotective action, indicating that HM plays a role, at least in part, as a CB1 receptor antagonist (FIG. 15). Thus, the neuroprotective action of HM is counteracted by a CB1 agonist, ACEA.

Experimental Example 2.3

Figure 16:
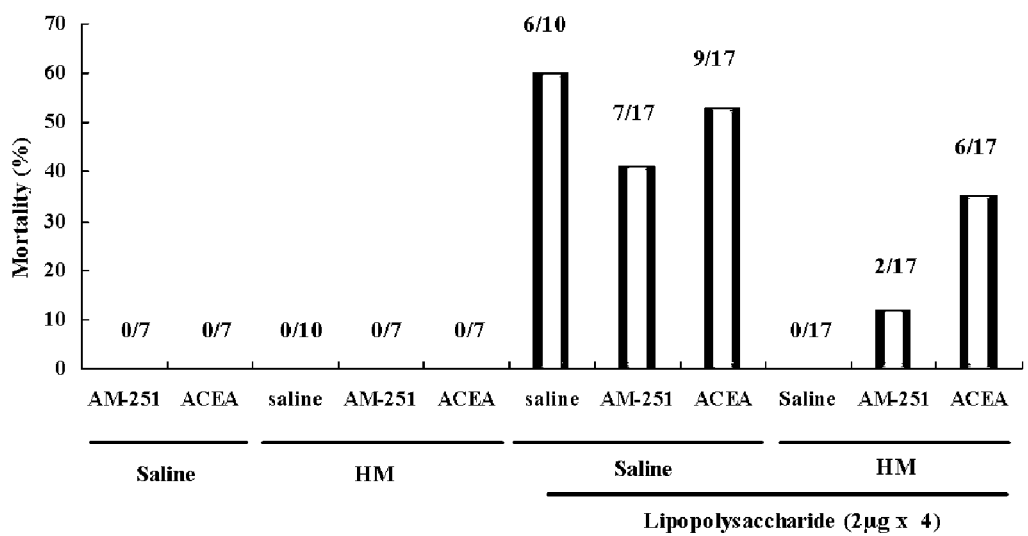
FIG. 16 shows effects of ACEA, a CB1 receptor agonist or AM-251, a CB1 receptor antagonist on the action of HM in response to lipopolysaccharide (LPS)-induced mortality. Mortality was observed by 2 weeks after bilateral LPS intrastriatal injection (one side: 2 μg×2). Note combined treatment of HM (20 mg/kg) did not produce mortality induced by LPS. HM (20 mg/kg) with or without ACEA (2 mg/kg)/AM-251 (0.3 mg/kg) was injected one a day for 2 weeks after LPS. First treatment of ACEA or AM-251 was performed at 45 min, and of HM was done at 30 min post-LPS.

HM Prevents LPS-induced Mortal Effects, and Attenuates LPS-Induced Reduced Tyrosine Hydroxylase-like Immunoreactivity (TH-IR) in Substantia Nigra of the Mice No animal died in the absence of LPS. Six out of ten mice died in two weeks after bilateral intrastriatal injection with LPS (one side; 2 μg×2). Neither AM-251 nor ACEA significantly changed LPS-induced mortality. No animal died in the HM pretreated LPS treated mice. ACEA reversed HM-induced protective (anti-mortal) effect. AM-251 also appears to block LPS-induced mortality (FIG. 16).

Figure 17:
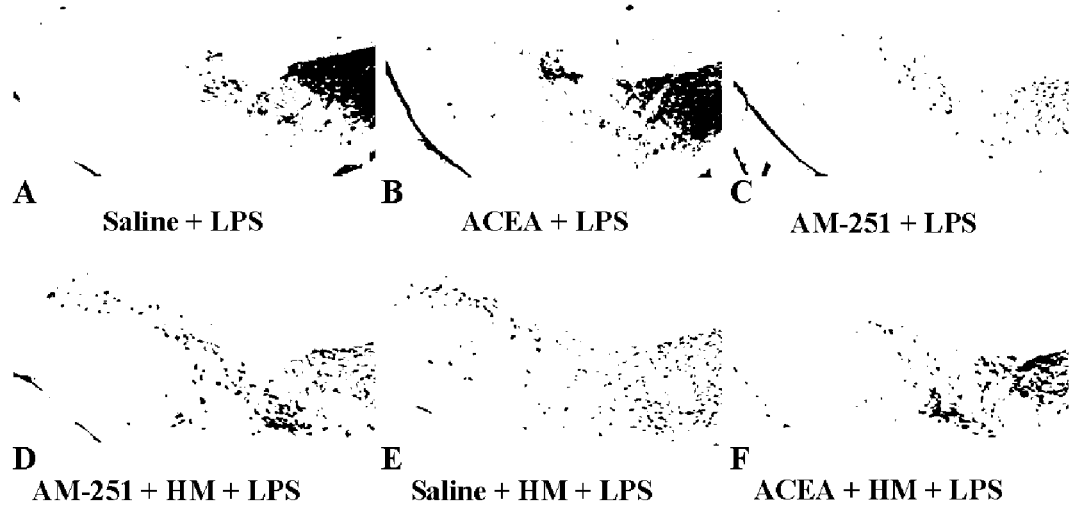
FIGS. 17A-17F show representative photographs of substantia nigra immunostained with tyrosine hydroxylase at 2 weeks after last LPS administration in the substantia nigra. Neuroprotective effect of HM was counteracted by ACEA, a CB1 agonist. Magnification=40×.

ACEA did not alter LPS-induced reduction in TH-IR, but AM-251 attenuates this reduction. Combined treatment of AM-251 with HM was more effective in protecting neuronal loss induced by LPS. This neuroprotective effect is comparable to that of HM alone in response to LPS insult. ACEA counteracted HM's protective effect on the LPS-induced loss in TH-IR (FIG. 17).

Experimental Example 2.4

Figure 18:
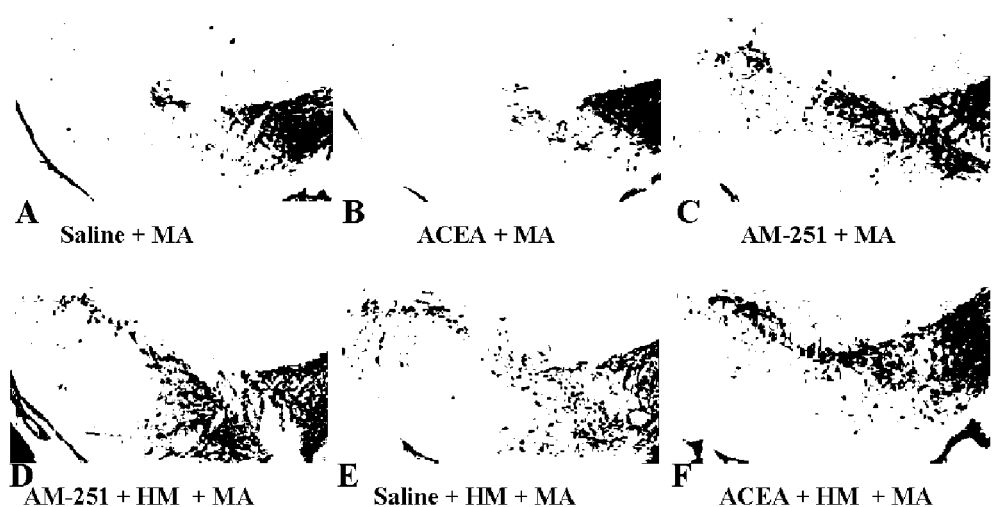
FIGS. 18A-18F show representative photographs of substantia nigra immunostained with tyrosine hydroxylase at 3 days after last methamphetamine (MA) administration in the substantia nigra. Neuroprotective effect of HM was counteracted by ACEA, a CB1 agonist. Compounds were administered 3 days before and after MA injection. Every treatment of ACEA (2 mg/kg) or AM-251 (0.3 mg/kg) was done 15 min prior to HM (20 mg/kg). Methods on first pretreatment of the drug were as follows; ACEA or AM-251 treated at 45 min before MA, while HM was done 30 min before MA. Animals were sacrificed at 72 h after final MA. Magnification=40×.

HM Prevents Methamphetamine (MA)-induced Reduction in Tyrosine Hydroxylase-like Immunoreactivity (TH-IR) in Substantia Nigra of the Mice Similar to the above mentioned two neurotoxins, MA-induced dopaminergic damage was noted. ACEA did not alter MA-induced reduction in TH-IR, but AM-251 attenuates this reduction. Combined treatment with AM-251 and HM was more efficacious in preventing reduction in TH-IR induced by MA. This neuroprotective effect is comparable to that of HM alone on the MA toxicity. ACEA reversed HM's protective effect on the MA-induced decrease in TH-IR (FIG. 18).

Experimental Example 2.5

Figure 19:
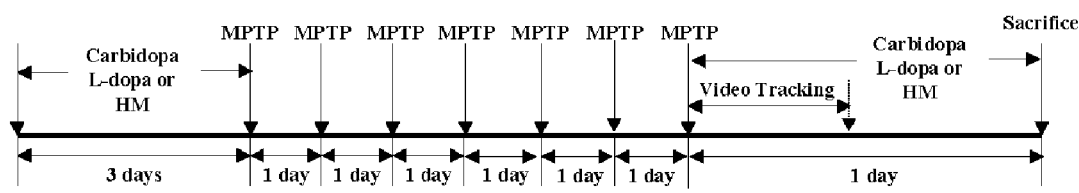
FIG. 19 shows experimental schedule for the evaluation of HM's effect in comparison with L-dopa with or without carbidopa in MPTP model.
Figure 20:
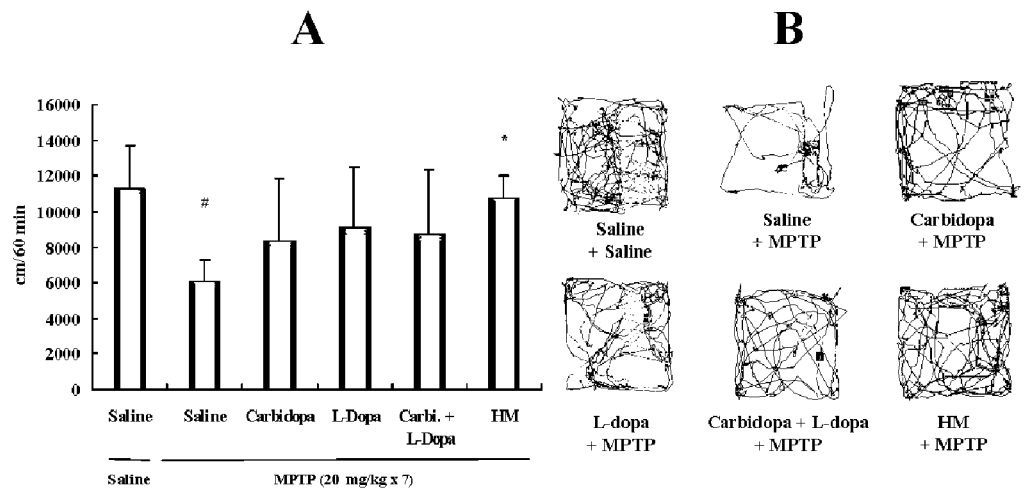
FIGS. 20A-20B show effects of carbidopa, L-dopa, carbidopa+L-dopa and HM on the changes in locomotor activity (A) and locomotor pattern (B) induced by MPTP in mice. Each value is the mean±S.E.M. of ten animals. *$P<0.05$ vs. Saline+MPTP, #$P<0.01$ vs. Saline+Saline (ANOVA with DMR test).

HM is More Effective than L-Dopa, Carbidopa, or Carbidopa Plus L-dopa in Preventing MPTP-induced Reductions in the Locomotor Activity and Nigral TH-IR in Mice A prescription drug for treating Parkinsonian patients is L-dopa or carbidopa plus L-dopa. Thus, the neuroprotective effects of HM was compared with L-dopa, carbidopa, or carbidopa plus L-dopa. As shown in FIG. 19, mice received MPTP (20 mg/kg, s.c.) once a day for consecutive seven days. Locomotor activity was examined for 60 min after final treatment of MPTP. Mice were sacrificed at 24 h after final MPTP administration. HM (24 mg/kg, i.p.), L-dopa (200 mg/kg, p.o.) with or without carbidopa (20 mg/kg, p.o.) was administered for 2 weeks before first MPTP challenge.

Figure 21:
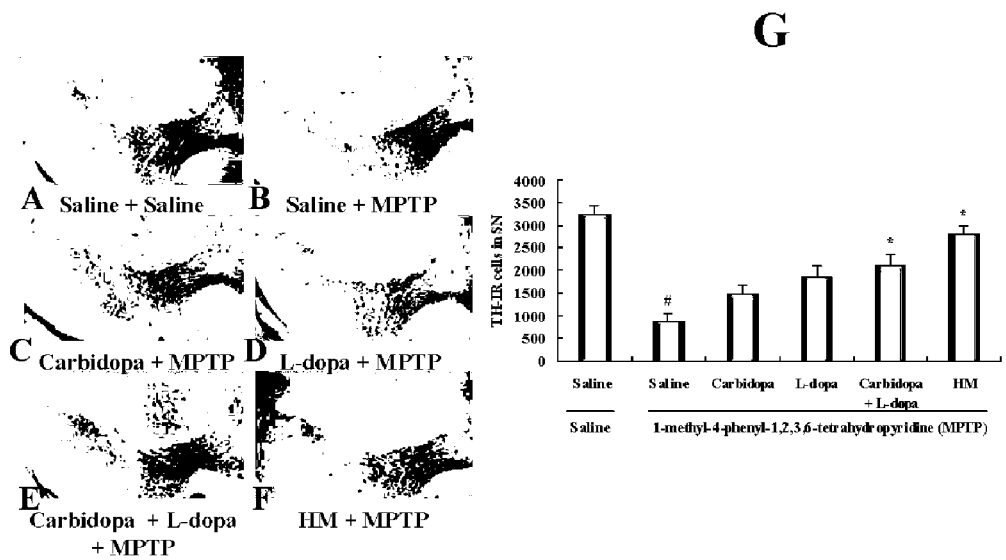
FIGS. 21A-21G show effects of carbidopa, L-dopa, carbidopa+L-dopa and HM on the nigral tyrosine hydroxylase-like immunoreactivity (TH-IR) of the mice treated with MPTP. Each value is the mean±S.E.M. of 5 animals. Total numbers of the TH-positive neurons throughout the substantia nigra pars compacta were counted. #$P<0.01$ vs. Saline+Saline, *$P<0.05$ vs. Saline+MPTP (ANOVA with DMR test). Magnification=40×.

MPTP induced a significant decrease (P<0.01 vs. saline treatment) in locomotor activity. However, the activity appeared to increase in the presence of L-dopa, carbidopa, and carbidopa plus L-dopa. HM significantly increased (P<0.05 vs. saline+MPTP) hypoactivity induced by MPTP. Consistently, MPTP-induced nigral loss in TH-IR (P<0.01 vs. Saline treatment) was significantly attenuated in the presence of carbidopa plus L-dopa (P<0.05 vs. saline+MPTP) or HM (P<0.05 vs. saline+MPTP). These results suggest that HM is more effective than L-dopa or carbidopa plus L-dopa (FIG. 21).

Experimental Example 2.6

Figure 22:
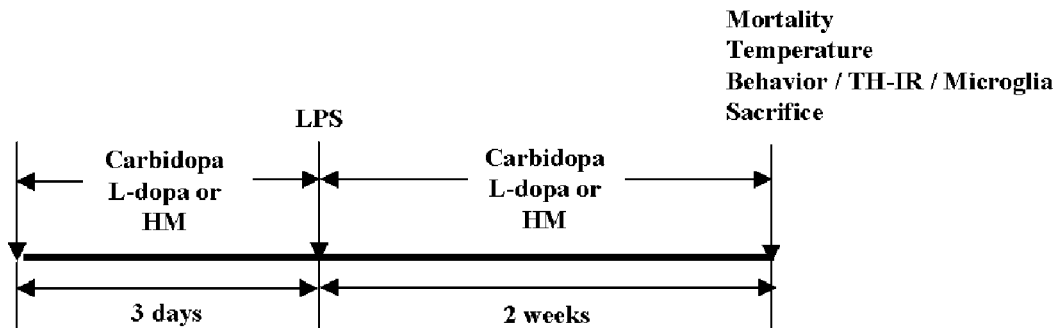
FIG. 22 shows experimental schedule for the evaluation of HM's effect in comparison with L-dopa with or without carbidopa in LPS model.
Figure 23:
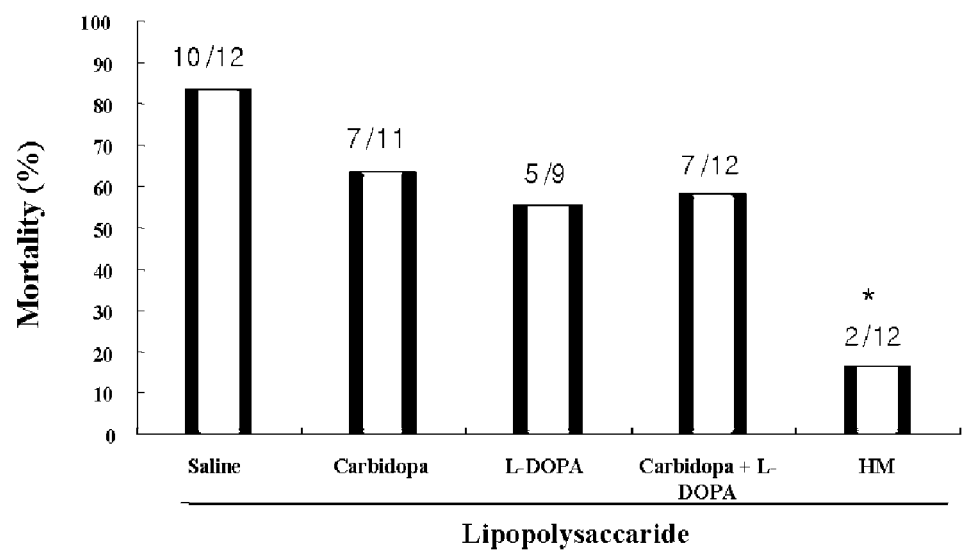
FIG. 23 shows effects of carbidopa, L-dopa, carbidopa plus L-dopa or HM in response to mortality induced by LPS. Mortality was observed by 2 weeks after LPS injection. *$P<0.01$ vs. Saline+LPS ($x^2$-test).

HM is More Effective than L-dopa, Carbidopa, or Carbidopa Plus L-dopa in Preventing LPS-induced Mortal Effects, Reductions in the Locomotor Activity, Nigral TH-IR, and Proliferation in Microglial Cell in Mice The neuroprotective effect of HM was compared with L-dopa, carbidopa, or carbidopa plus L-dopa in response to dopaminergic damage induced by LPS. Experimental schedule is shown in FIG. 22. Intrastriatal injection of LPS (2 μg×4/head) produced high mortality (ten animals died out of twelve animals in the 2 weeks after LPS administration). Although pretreatment with carbidopa alone, L-dopa alone, or carbidopa plus L-dopa appears to attenuate mortality induced by LPS, protective effect of HM is most pronounced (Saline+LPS vs. HM+LPS, P<0.01, Chi-square test) than that of carbidopa alone, L-dopa alone, or carbidopa plus L-dopa (FIG. 23).

Figure 24:
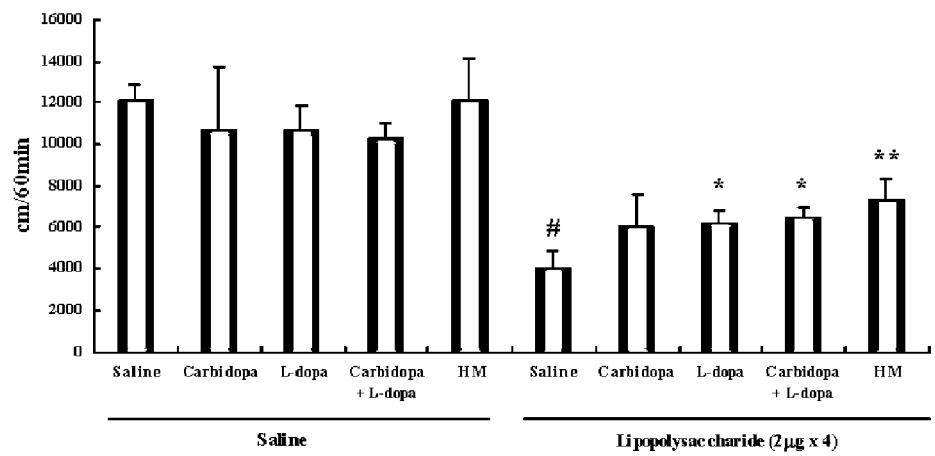
FIG. 24 shows effects of HM, carbidopa, L-dopa, carbidopa plus L-dopa on the hypolocomotion induced by LPS in mice. Each value is the mean±S.E.M. of ten animals. #$P<0.01$ vs. Saline+Saline, *$P<0.05$ vs. Saline+LPS, **$P<0.01$ vs. Saline+LPS (ANOVA with DMR test).
Figure 25:
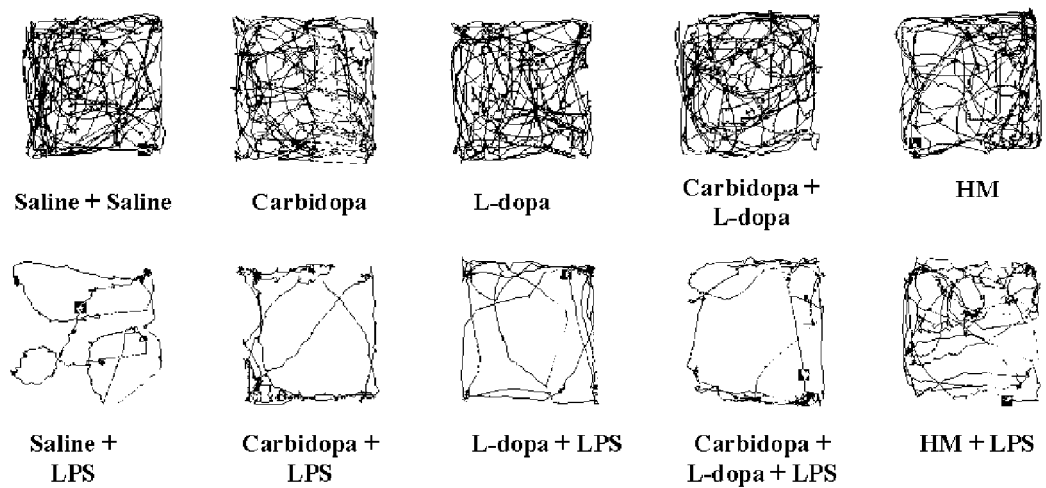
FIG. 25 shows the representative locomotor pattern on the effects of carbidopa, L-dopa, carbidopa+L-dopa and HM in response to LPS in mice.

Locomotor activity was examined for 60 min at 3 weeks after LPS treatment. LPS-induced significant reduction (P<0.01 vs. saline treatment) in locomotor activity was attenuated by L-dopa (P<0.05), carbidopa+L-dopa (P<0.05) or HM (P<0.01) (FIGS. 24 and 25).

Figure 26:
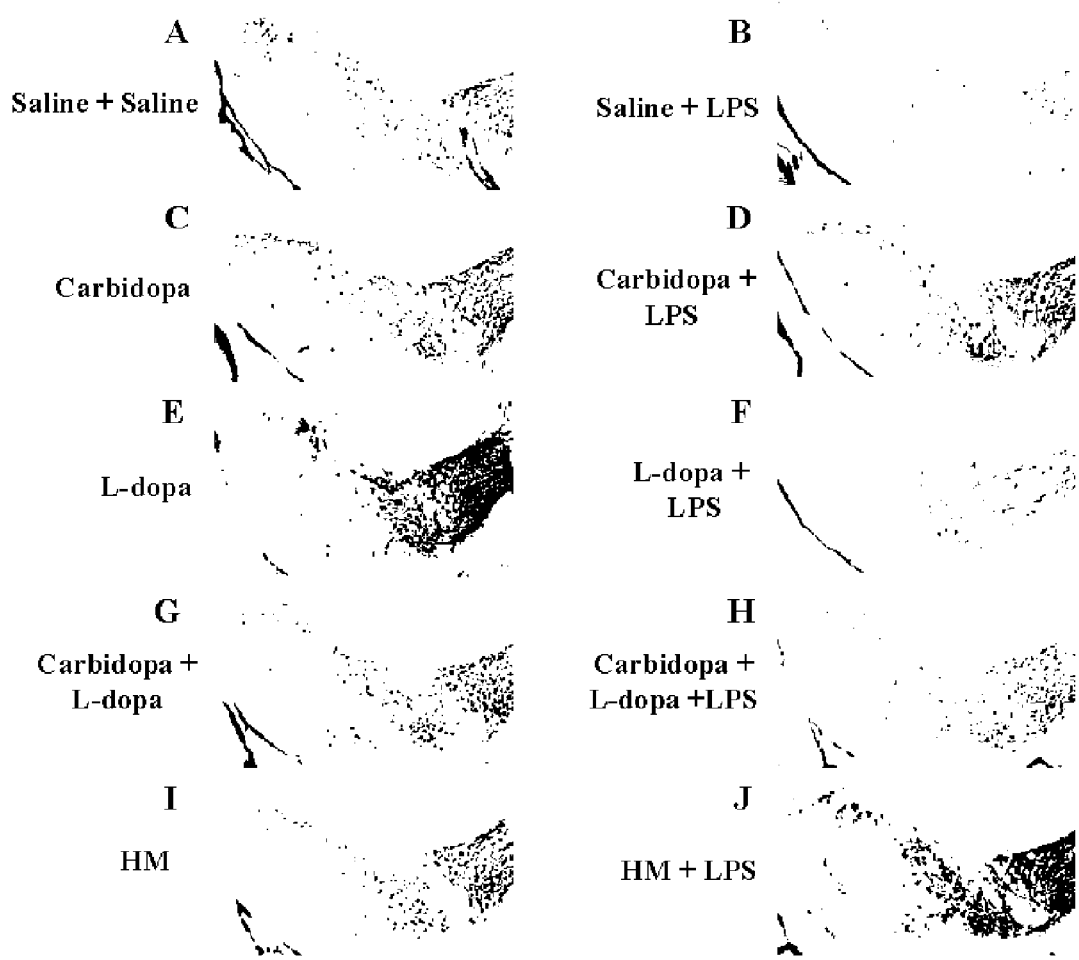
FIGS. 26A-26J show representative photomicrographs on the effects of carbidopa, L-dopa, carbidopa plus L-dopa or HM on the LPS-induced reduction in TH-IR. Magnification=40×.
Figure 27:
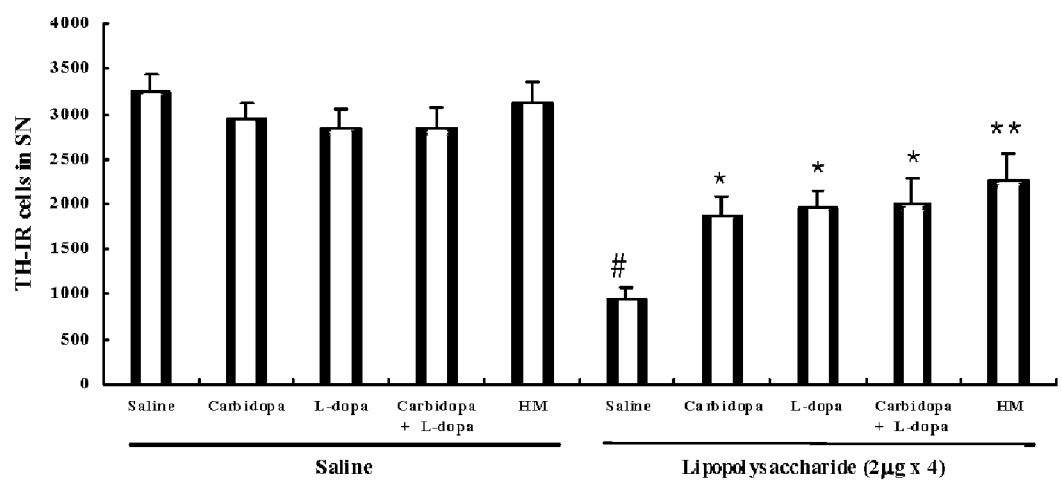
FIG. 27 show effects of carbidopa, L-dopa, carbidopa+L-dopa and HM on the nigral tyrosine hydroxylase-like immunoreactivity (TH-IR) of the mice treated with LPS. Each value is the mean±S.E.M. of ten animals. #$P<0.01$ vs. Saline+Saline, *$P<0.05$ vs. Saline+LPS, **$P<0.01$ vs. Saline+LPS (ANOVA with DMR test).

TH-IR in the substantia nigra was not changed at all in the absence of LPS. LPS-induced loss in TH-IR was significantly attenuated by the treatment of carbidopa (P<0.05), L-dopa (P<0.05), carbidopa+L-dopa (P<0.05), and HM (P<0.01). HM is the most effective in attenuating LPS-induced reduction in TH-IR (FIGS. 26 and 27).

Figure 28:
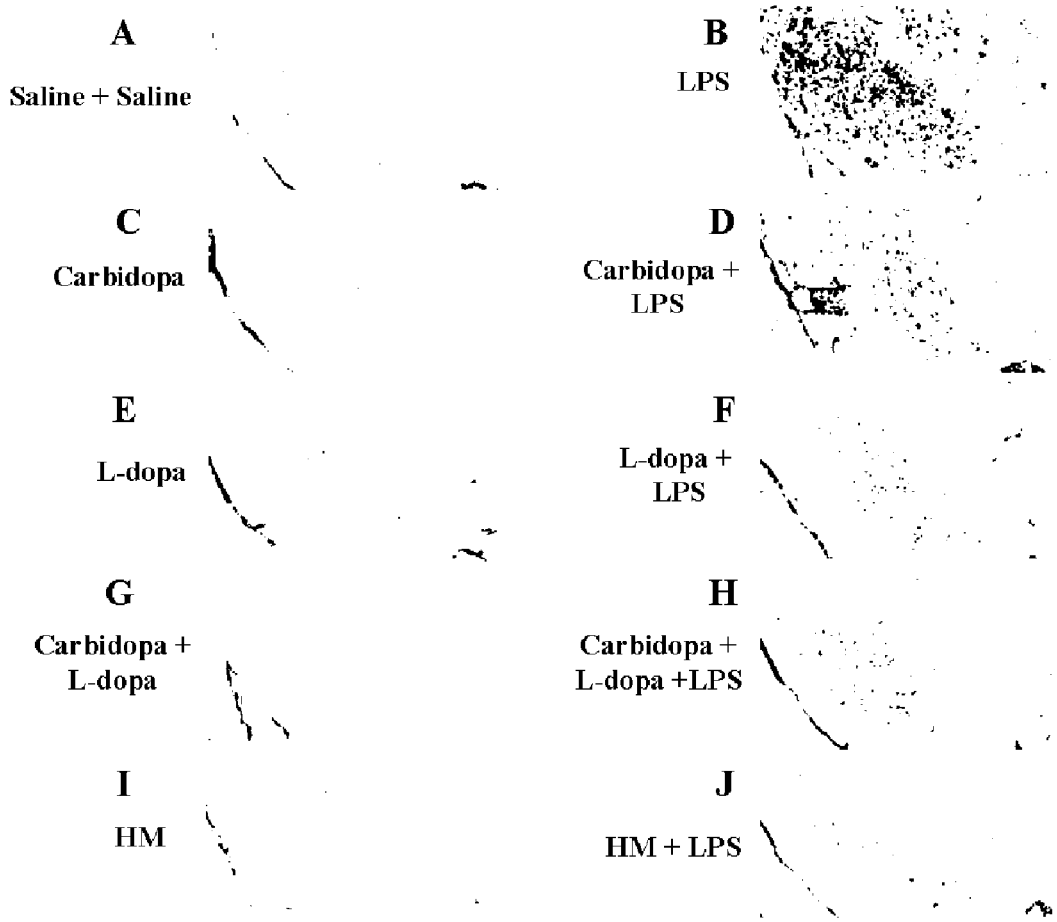
FIG. 28 shows representative photomicrographs on the induction of microglial cell as labeled by F4/80 in the substantia nigra of the mice. Magnification=40×.
Figure 29:
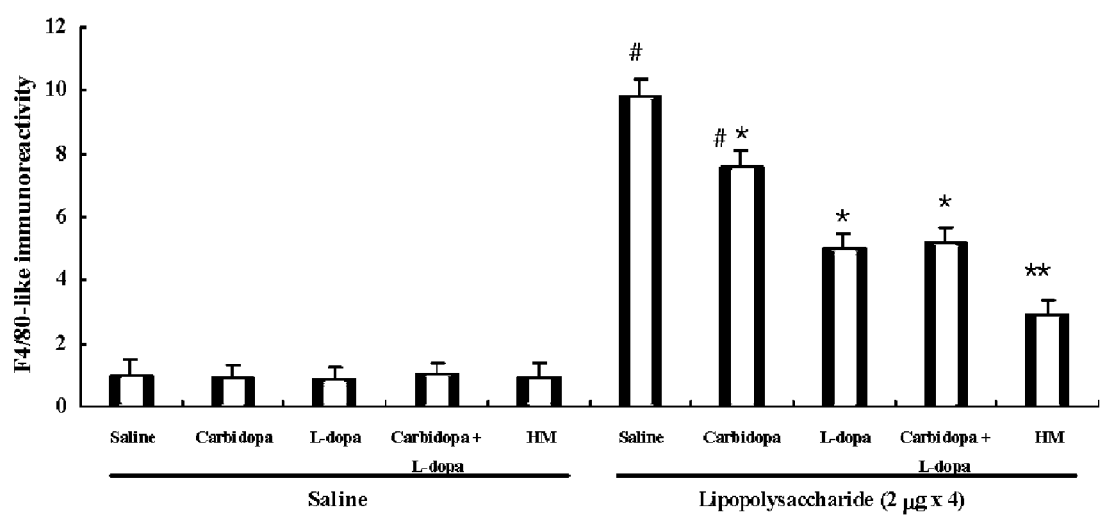
FIG. 29 shows effects of carbidopa, L-dopa, carbidopa+L-dopa and HM on the nigral increases in F4/80 immunoreactivity of the mice treated with LPS. Each value is the mean±S.E.M. of 6 animals. #$P<0.01$ vs. Saline+Saline, *$P<0.05$ vs. Saline+LPS, **$P<0.01$ vs. Saline+LPS (ANOVA with DMR test).

A very little induction of microglia as labeled by F/80-like immunoreactivity was observed in the absence of LPS. However, LPS-induced microglial cell proliferation was significantly enhanced (P<0.01) as compared with saline treated group. This F4/80-like immunoreactivity was significantly attenuated by the treatment of carbidopa (P<0.05), L-dopa (P<0.05), carbidopa+L-dopa (P<0.05), and HM (P<0.01). HM is the most effective in attenuating LPS-induced increase in F4/80-like immunoreactivity (FIGS. 28 and 29).

Experimental Example 2.7

HM is More Effective than L-dopa, Carbidopa, or Carbidopa Plus L-dopa in Preventing Methamphetamine (MA)-induced Hyperthermia, Reductions in the Locomotor Activity, Nigral TH-IR in Mice.

Figure 30:
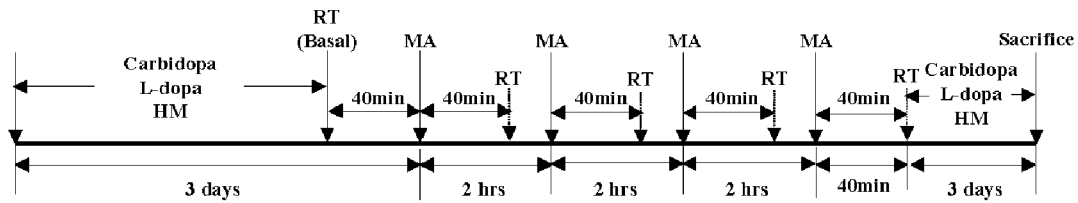
FIG. 30 shows experimental schedule for the evaluation of HM's effect in comparison with L-dopa with or without carbidopa; Methamphetamine model.
Figure 31:
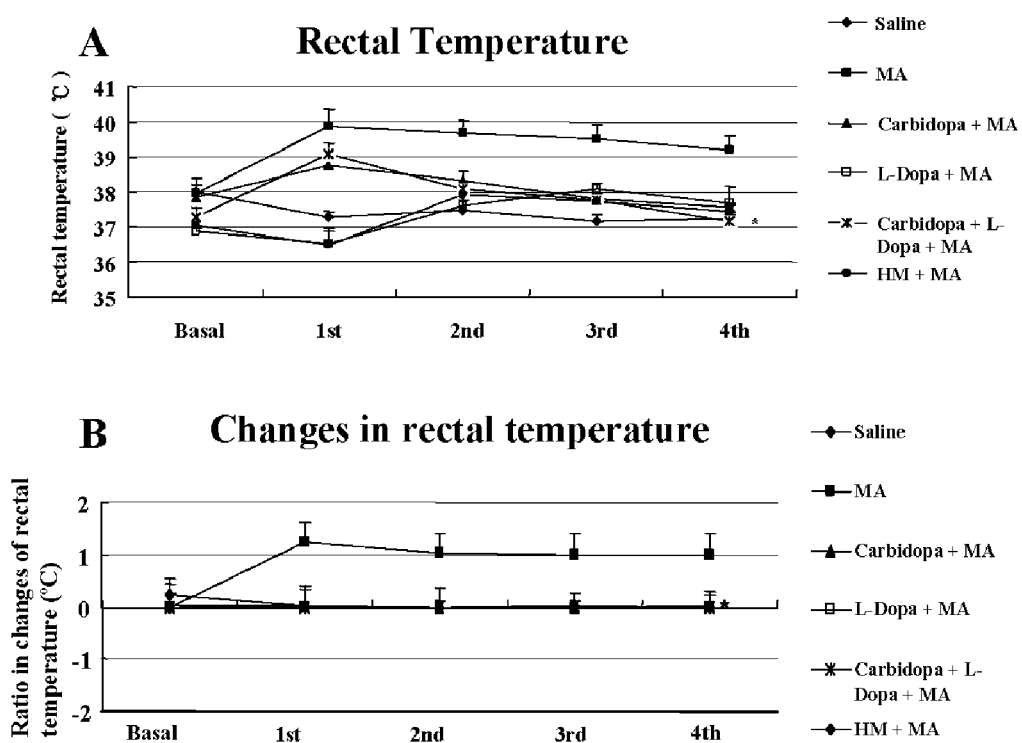
FIGS. 31A-31B show effect of drugs on the MA-induced hyperthermia. Mice received MA injections as 2 hrs' time interval under the ambient temperature of 22.0±0.5° C. Each value is the mean±S.E.M. of 6 animals. #P<0.01 vs. Saline, *P< 0.01 vs. MA alone (ANOVA for repeated measures).

Experimental paradigm for MA with or without compounds is in FIG. 30. Treatment with MA (7.5 mg/kg, i.p.× four times as two hour time interval) produces hyperthermia (P<0.01). Pretreatment of carbidopa, L-dopa, carbidopa+L-dopa or HM significantly attenenuated (P<0.01) MA-induced hyperthermia (FIG. 31).

Figure 32:
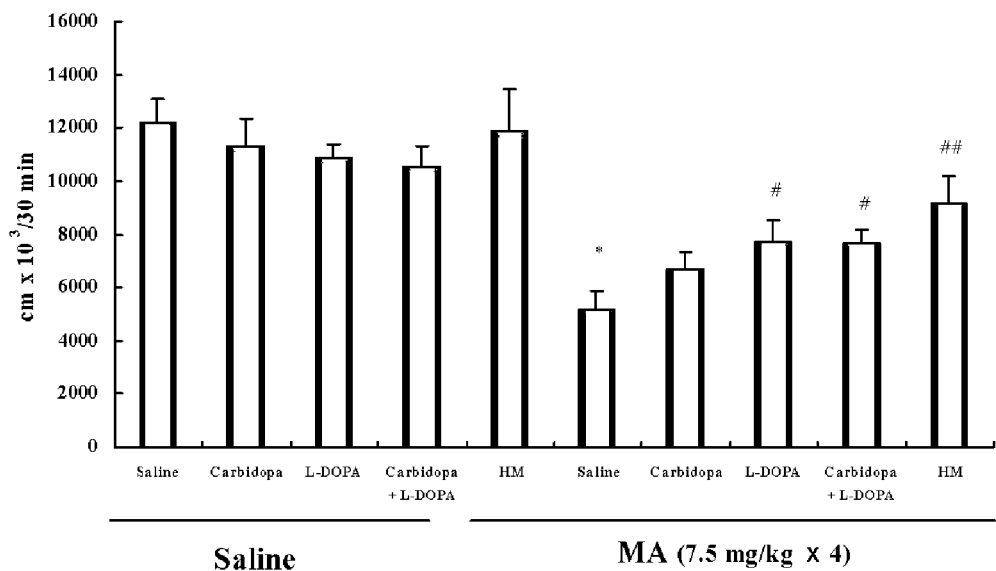
FIG. 32 shows effects of HM, carbidopa, L-dopa, carbidopa plus L-dopa on the hypolocomotion induced by MA in mice. Each value is the mean±S.E.M. of ten animals. *P<0.01 vs. Saline+Saline, #P<0.05 vs. Saline+LPS, ##P<0.01 vs. Saline+LPS (ANOVA with DMR test).

A significant reduction (P<0.01) in locomotor activity at 3 days after MA injections was significantly enhanced by the treatment of L-dopa, carbidopa+L-dopa or HM. Effect of HM is more efficacious than that of L-dopa or carbidopa+L-dopa (FIG. 32).

Figure 33:
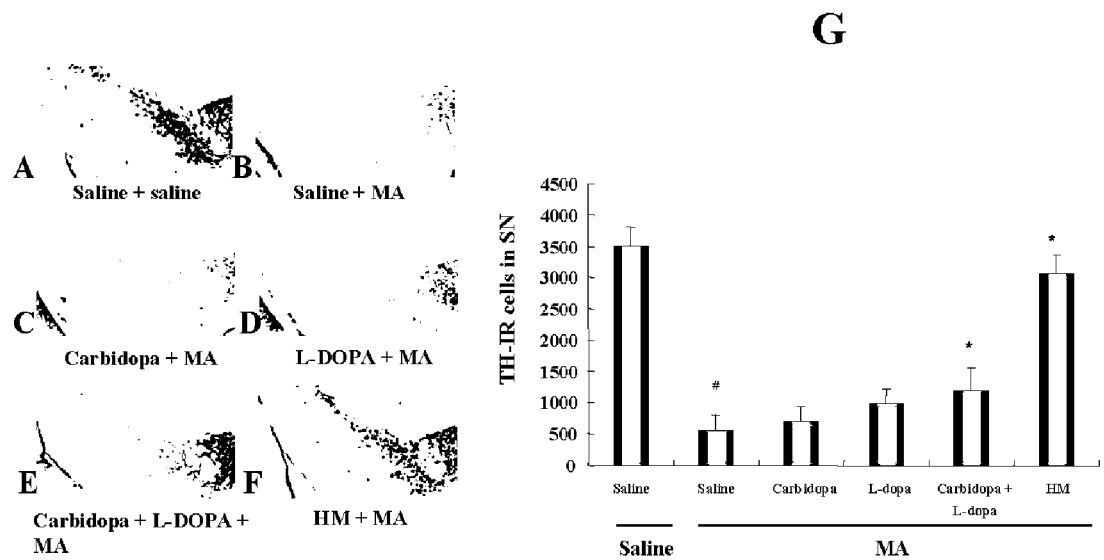
FIGS. 33A-33G show effects of carbidopa, L-dopa, carbidopa plus L-dopa, and HM on the nigral tyrosine hydroxylase-like immunoreactivity (TH-IR) of the mice treated with MA. Each value is the mean±S.E.M. of 5 animals. Total numbers of the TH-positive neurons throughout the substantia nigra pars compacta were counted. #P<0.01 vs. Saline+Saline, *P<0.05 vs. Saline+MA (ANOVA with DMR test). Magnification=40×.

MA-induced nigral loss in TH-IR was significantly observed (Saline treated group vs. saline+MA, P<0.01). Although this reduction was significantly attenuated by the treatment of carbidopa+L-dopa, HM's effect was more pronounced than that of carbidopa+L-dopa (FIG. 33).

Experimental Example 3

Effects of Morphinan on Drug Dependence

Beneficial effects of dextrorotatory morphinans on drug dependence was determined. The effects of morphinans on the behavioural side effects induced by cocaine or methamphetamine (MA) was also examined. Effects of dextrorotatory morphinans, in particular, dextromethorphan (DM), 3-methoxymorphinan (MM), 3-hydroxymorphinan (HM), 3-allyloxy-17-methoxymorphinan (AM), 3-cyclopropyl-17-methoxymorphinan (CM) and dimemorfan (DF) on the changes in the locomotor activity, conditioned place preference (CPP) or fos-related antigen-immunoreactivity (FRA-IR) was examined after prolonged treatment with cocaine or MA. Prolonged treatment with cocaine (5 or 20 mg/kg, i.p./day×7) significantly enhanced locomotor activity. Combined treatment with DM (15 or 30 mg/kg, i.p.) attenuated hyper-locomotor activity induced by a high dose of cocaine (20 mg/kg). However, DM (30 mg/kg) significantly enhanced locomotor activity induced by a low dose of cocaine (5 mg/kg). Similarly, although MM (15 or 30 mg/kg) attenuated locomotor activity induced by a high dose of cocaine change, MM did not alter locomotor activity induced by a low dose of cocaine (5 mg/kg), suggesting that these morphinans shift their dose-response curve to the left. In contrast, other morphinans (HM, AM, CM and DF) consistently attenuated locomotor activity induced by a low dose of cocaine, although their actions on the locomotor activity induced by a high of cocaine were not uniform. These four morphinans shifted their dose-response curve consistently to the right. Their profile of behavioural effects is parallel with that of striatal FRA-IR. Since morphinans (in particular HM) have relatively high affinity for the cannabinoid CB1 site and recent investigation suggests blockade of CB1 receptor offer a novel approach for preventing drug dependence, it was examined whether CB1 receptor is involved in the pharmacological action of HM in response to cocaine-induced psychological dependence as measured by conditioned place preference (CPP) and behavioural sensitization. Cocaine-induced CPP was significantly observed. A CB1 receptor agonist, ACEA (2 mg/kg, i.p.) produced CPP. However, neither HM (20 mg/kg) nor a CB1 receptor antagonist, AM 251 (0.3 mg/kg, i.p.) exhibited CPP. ACEA did not alter cocaine-induced CPP, but AM 251 or HM attenuated cocaine-induced CPP. Mice pretreated with cocaine (10 mg/kg, i.p./day×7) at one month before a single dose of cocaine (10 mg/kg, i.p.) significantly increased locomotor activity, as compared with mice receiving a single dose of cocaine (10 mg/kg.i.p.), suggesting that cocaine-induced behavioural sensitization was clearly induced in this experimental paradigm. Although HM significantly attenuated cocaine sensitization, neither ACEA nor AM 251 did significantly change cocaine sensitization.

Prolonged treatment with MA (1 mg/kg, i.p./day×7) increased locomotor activity. Combined treatment with DM (20 mg/kg, i.p.) did not alter MA-induced locomotor activity. However, DF (20 mg/kg, i.p.), AM (20 mg/kg, i.p.) or CM (20 mg/kg, i.p.) significantly attenuated (P<0.05) locomotor activity induced by MA. These behavioural effects are in line with the profile of the striatal FRA-IR in the mice. Pretreated MA (1 mg/kg, i.p./day×7) at seven days before a single challenge of MA (1 mg/kg, i.p.×1) produced significant increase in locomotor activity, indicating that behavioural sensitization induced by MA occurred. Although DM did not affect MA sensitization, each morphinan dose of 20 mg/kg (DF, AM, CM or HM) significantly attenuated (P<0.05) MA sensitization. Neither ACEA (2 mg/kg, i.p.) nor AM 251 (0.3 mg/kg, i.p.) affected MA sensitization. However, ACEA significantly counteracted HM's pharmacological action on MA sensitization, while AM 251 did not significantly influence HM's effects.

MA-induced CPP was noted. ACEA alone produced its own CPP (P<0.05 vs. Saline-treated group). In contrast, ACEA did not affect CPP produced by MA. However, AM251 or HM significantly blocked CPP produced by MA. ACEA reversed HM's pharmacological action in response to CPP produced by MA, but AM 251 did not significantly affect HM's action.

Taken together, morphinan analogs, particular, DF, AM, CM and HM possess an anti-psychotropic potential in response to cocaine or MA. In particular, HM-mediated pharmacological action is, at least in part, via blockade of CB 1 receptor.

Experimental Example 3.1

Animals and Treatments

All animals were handled in accordance with the NIH guidelines for the humane care of laboratory animals. Male C57BL/6 mice (Bio Genomics, Inc., Charles River Technology, Gapyung-Gun, Gyeonggi-Do, Korea) weighing about 25 g were maintained on a 12:12 h light:dark cycle and fed ad libitum. They were adapted to these conditions for 2 weeks before the experiment. All the rodents were drug and seizure naive before testing. Cocaine (NIDA/NIH, Rockville, Md.) or methamphetamine (MA; NIDA/NIH, Rockville, Md.) was dissolved in sterilized saline.

Experimental Example 3.2

Conditioned Place Preference (Psychological Dependence)

The control mice received an i.p. injection of saline just before entering the white or black compartment. Cocaine or MA dissolved in saline was administered immediately before the mice were placed in the white compartment. To test the effect of cocaine alone or MA alone or in combination with exemplified morphinans (DM, HM, AM, CM or DF), each morphinan was administered 2 hr before cocaine or saline injection.

On day 1, the mice were pre-exposed to the test apparatus for 5 min. The guillotine doors were raised and the mice were allowed to move freely between the two compartments. On day 2, the time each mouse spent in each compartment was recorded for 15 min. On days 3, 5, 7, 9, 11, and 13, the mice were injected with cocaine before being confined to the white compartment, the non-preferred side, for 20 min. On days 4, 6, 8, 10, and 12, the mice were injected with saline before being confined to the black compartment, the preferred side, for 20 min. On day 14, the guillotine doors were raised. The mice were initially placed in the tunnel and the time spent by the mice in the two compartments was recorded for 15 min. The scores were calculated from the differences in the time spent in the white compartment in the testing and pre-testing phases.

Experimental Example 3.3

Locomotor Activity

Locomotor activity was measured using an automated video-tracking system (Noldus Information Technology, Wagenin, The Netherlands). Eight test boxes (40×40×30 cm high) were operated simultaneously by an IBM computer. Animals were studied individually during locomotion in each test box, where they were adapted for 5 min before starting the experiment. A printout for each session showed the pattern of the ambulatory movements of the test box. The distance traveled in cm by the animals in horizontal locomotor activity was analyzed. Data were collected and analyzed between 0900 and 1700 h.

Experimental Example 3.4

Fos-related Antigen Immunoreactivity (FRA-IR)

FRA-IR in the striatum was induced at maximal levels at 18 h after the final cocaine/MA injection. Therefore, brains were removed and used for immunocytochemical analysis at 18 h after the final cocaine/MA treatment. The coronal sections containing striatum were processed for FRA immunocytochemistry. Prior to overnight incubation with the primary antibody, sections were pre-washed in 0.2% Triton X-100 for 15 min, followed by 4% normal goat serum for 20 min. After a 24 h incubation with the primary antiserum, sections were then incubated with a secondary biotinylated antiserum (1:800 dilution) for 1 h. Sections were always washed three times with PBS (pH 7.4) between each incubation step. The avidin-biotin complex method (ABC Kits, Vector Laboratories, Inc.) with 3,3'-diaminobenzidine tetrahydrochloride as the chromogen was used to visualize immunoreactive cells. The FRA antibody was used at 1:2,000 as the optimal dilution. The FRA-IR in the striatum was calculated using image analysis systems with a polaroid digital microscopic camera (Optimas version 6.2).

Experimental Example 3.5

Statistical Analysis

Significance was analyzed with Student's t-test for paired data and with ANOVA for repeated measures. A significant level of less than 0.05 was accepted for comparisons.

Experimental Example 3.6

Figure 34:
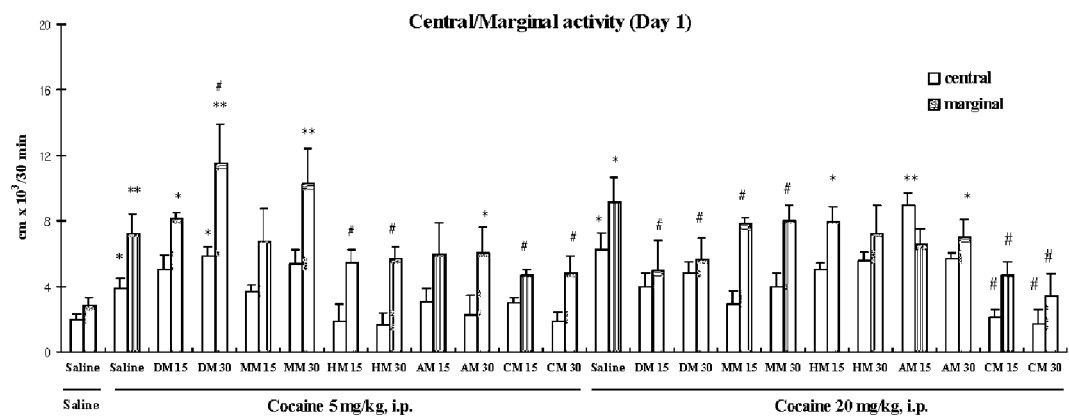
FIGS. 34A-34B show effect of morphinans on the cocaine-induced hyperactivity in the mice. Morphinans (15 and 30 mg/kg, i.p.) were administered 30 minutes prior to cocaine (5 and 20 mg/kg, i.p.). Central activity means relatively non-specific locomotor activity in the center of the box. Marginal activity means circling behaviors. All treatments were performed for 7 days. Each value is the mean±S.E.M. of 6 animals. *P<0.05 vs. saline, **P<0.01 vs. saline, #P<0.05 or ##P<0.01 vs. saline+corresponding dose of cocaine (ANOVA with DMR test).
Figure 34:
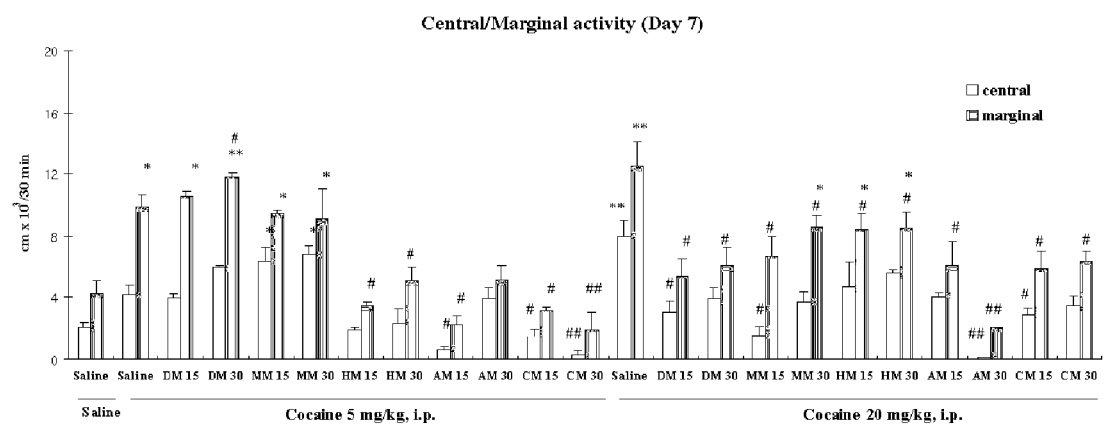
Figure 35:
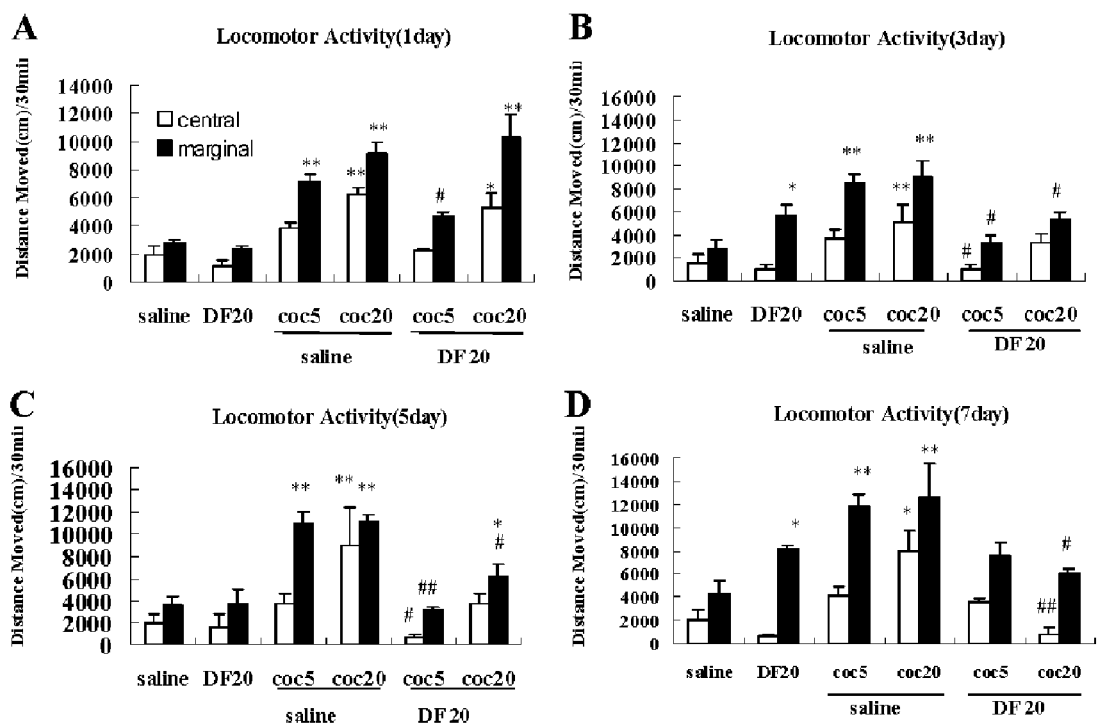
FIGS. 35A-35D show effect of dimemorfan (DF) on cocaine-induced hyperactivity in the mice. DF (20 mg/kg, i.p.) was administered 30 minutes prior to cocaine (5 and 20 mg/kg, i.p.). All treatments were performed for 7 days. Each value is the mean±S.E.M. of 6 animals. *P<0.05 vs. saline, **P<0.01 vs. saline, #P<0.05 vs. corresponding control, ##P<0.01 vs. corresponding control (ANOVA with DMR test).

The Effects of Morphinans (DM, MM, AM, CM, HM and DF) on Cocaine-induced Hyperlocomotion in Mice Saline alone did not significantly alter locomotor activity. Cocaine (5 or 10 mg/kg) caused an increase in locomotor activity over time. The increase in locomotor activity was more pronounced following the $7^{th}$ cocaine challenge than first challenge. Although treatment with DM or MM (15 or 30 mg/kg) (30 min before cocaine) attenuated (either dose of DM or MM plus 20 mg/kg of cocaine vs. 20 mg/kg of cocaine, P<0.05) the high dose of cocaine-induced hyperactivity, 30 mg/kg of DM enhanced locomotor activity produced by a low dose of cocaine (5 mg/kg, i.p.). Similarly, either dose of MM did not influence locomotor activity mediated by a low dose of cocaine. In contrast, other morphinans are consistently effective in attenuating locomotor activity induced by a low dose of cocaine. Combined, they shift their dose response curve to the right, suggesting that they have anti-psychotomimetic effects (FIGS. 34 and 35).

Experimental Example 3.7

Figure 36:
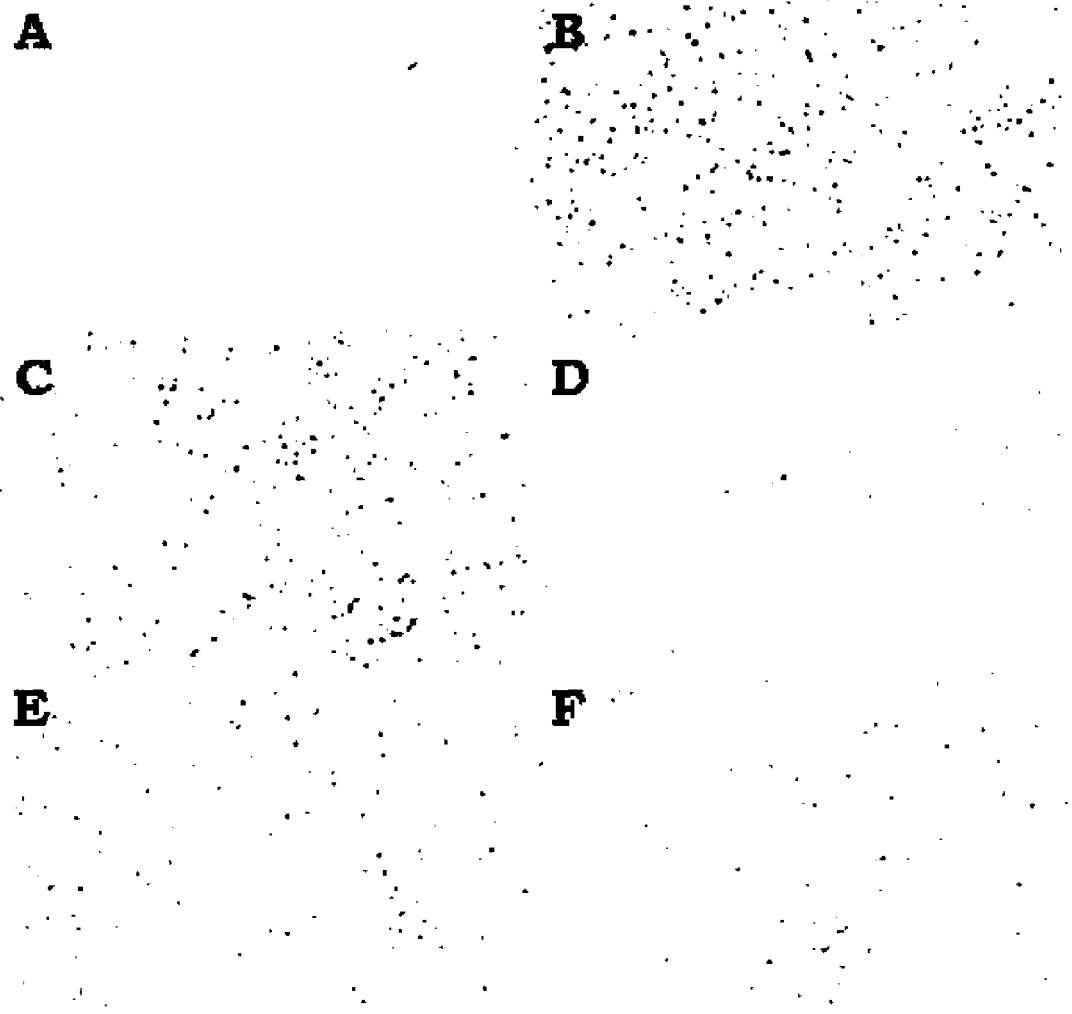
FIGS. 36A-36F show representative photomicrographs showing Fos-related antigen-immunoreactive neurons in the dorsolateral striatum of mice brains. A: Saline, B: DM (20 mg/kg, i.p.)+Cocaine (5 mg/kg, i.p.), C: Cocaine (5 mg/kg, i.p.), D: DF (20 mg/kg, i.p.)+Cocaine, E: AM (20 mg/kg, i.p.)+Cocaine, F: CM (20 mg/kg, i.p.)+Cocaine. Magnification=100×.

The Effects of Morphinans (DM, MM, AM, CM, HM and DF) on Cocaine-induced Fos-related Antigen-immunoreactivity (FRA-IR) in the Striatum of the Mice One of the important transcription factors in the neuronal adaptation/stimulation induced by psychotropic agent, FRA was barely expressed without cocaine. Prolonged treatment with cocaine (5 mg/kg) markedly induced FRA-IR in the striatum. Neither DM nor MM affects this induction of FRA-IR mediated by cocaine. In contrast, cocaine-caused FRA-IR was apparently attenuated by the treatment with DF, AM, CM or HM (FIG. 36).

Experimental Example 3.8

Figure 37:
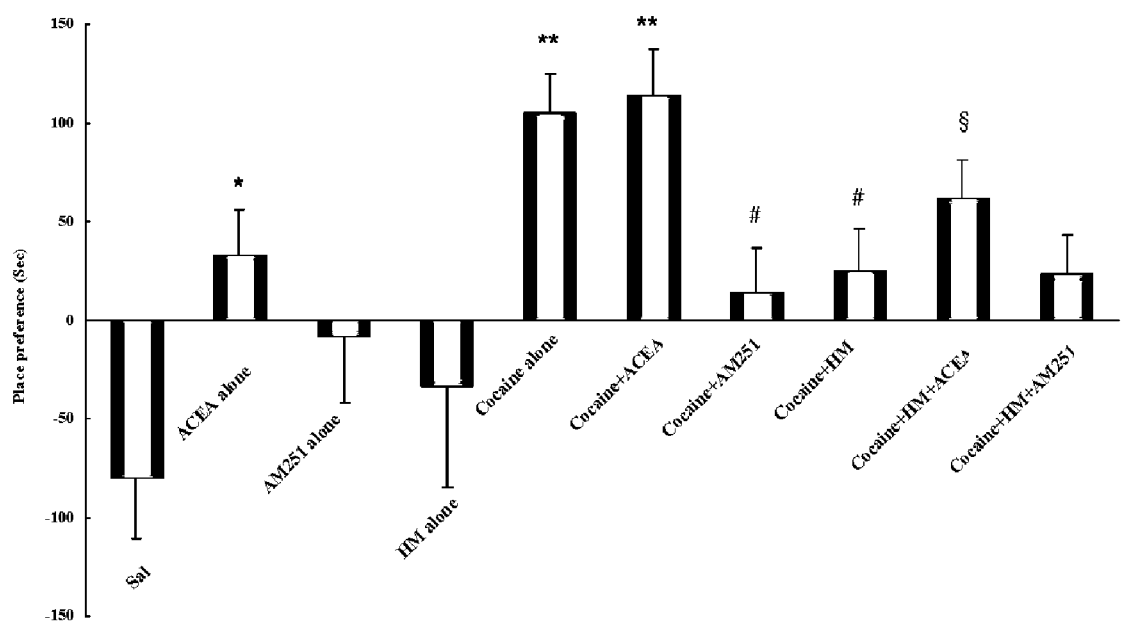
FIG. 37 shows effect of cannabinoid CB1 receptor modulation on the HM-mediated action in response to cocaine-induced conditional place preference. Each value is the mean±S.E.M. of 10 animals. *P<0.05 or **P<0.01 vs. Sal-treated group, #P<0.05 vs. cocaine, §P<0.05 vs. Coc+HM (ANOVA with DMR test).

The Effects of Cannabinoid CB1 Receptor Agonist (ACEA) or CB1 Receptor Antagonist (AM 251) on HM-Mediated Pharmacological Action in Response to Cocaine-induced CPP Neither saline-, AM 251 (0.3 mg/kg)-treated nor HM (20 mg/kg)-treated animals showed any CPP response. In contrast, ACEA (2 mg/kg)-treated animals showed CPP effects (P<0.05 vs. saline-treated animals). Cocaine (10 mg/kg) induced significant CPP effects (P<0.01). ACEA did not alter CPP effects by cocaine. However, AM 251 or HM significantly reduced (P<0.05) the CPP produced by cocaine. AM 251 did not affect HM's effect in response to cocaine-induced CPP. In contrast, ACEA appears to counteract the cocaine-induced CPP (FIG. 37).

Experimental Example 3.9

Figure 38:
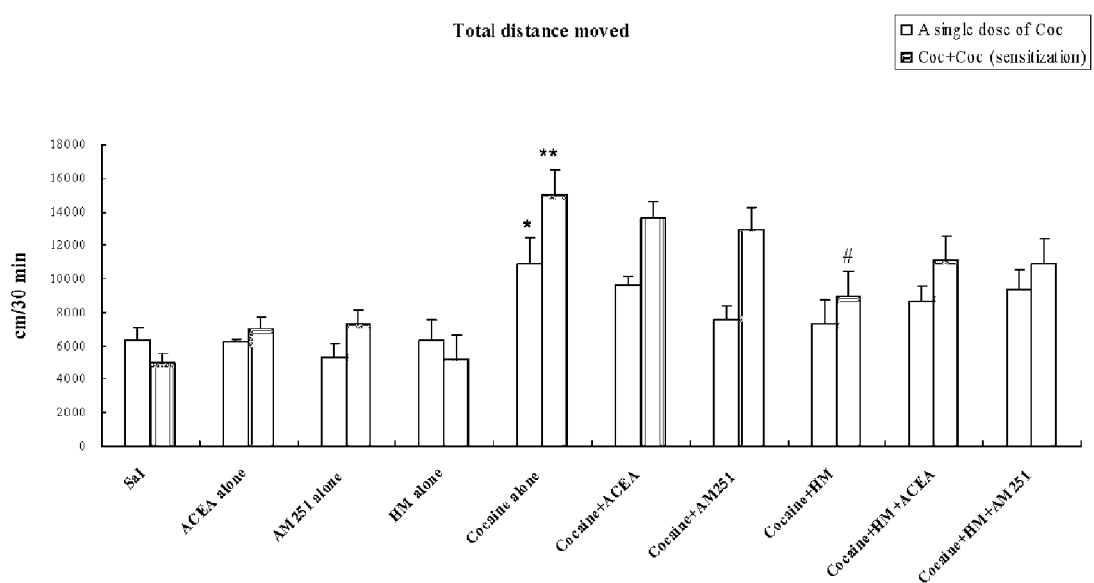
FIG. 38 shows effect of cannabinoid CB1 receptor modulation on the HM-mediated action in response to cocaine-induced behavioral sensitization. Each value is the mean±S.E.M. of 10 animals. *P<0.05 or **P<0.01 vs. Sal, #P<0.05 vs. cocaine alone (ANOVA with DMR test).

The Effects of Cannabinoid CB1 Receptor Agonist (ACEA) or CB1 Receptor Antagonist (AM 251) on HM-mediated Pharmacological Action in Response to Cocaine-induced Behavioural Sensitization Neither saline-, AM 251 (0.3 mg/kg)-, ACEA (2 mg/kg)-treated nor HM (20 mg/kg)-treated animals showed any specific behavioural effects. Cocaine induced significant behavioural sensitization locomotor activity of the animals receiving a single challenge of cocaine vs. locomotor activity of animals pretreated with cocaine (10 mg/kg/day, i.p.×7) at one month before a single challenge of cocaine, $P<0.01$]. Neither ACEA nor AM 251 alter behavioural sensitization by cocaine. However, HM significantly reduced ($P<0.05$) the behavioural sensitazation produced by cocaine. Neither ACEA nor AM 251 significantly alter HM's effect in response to cocaine-induced sensitization (FIG. 38).

Experimental Example 3.10

Figure 39:
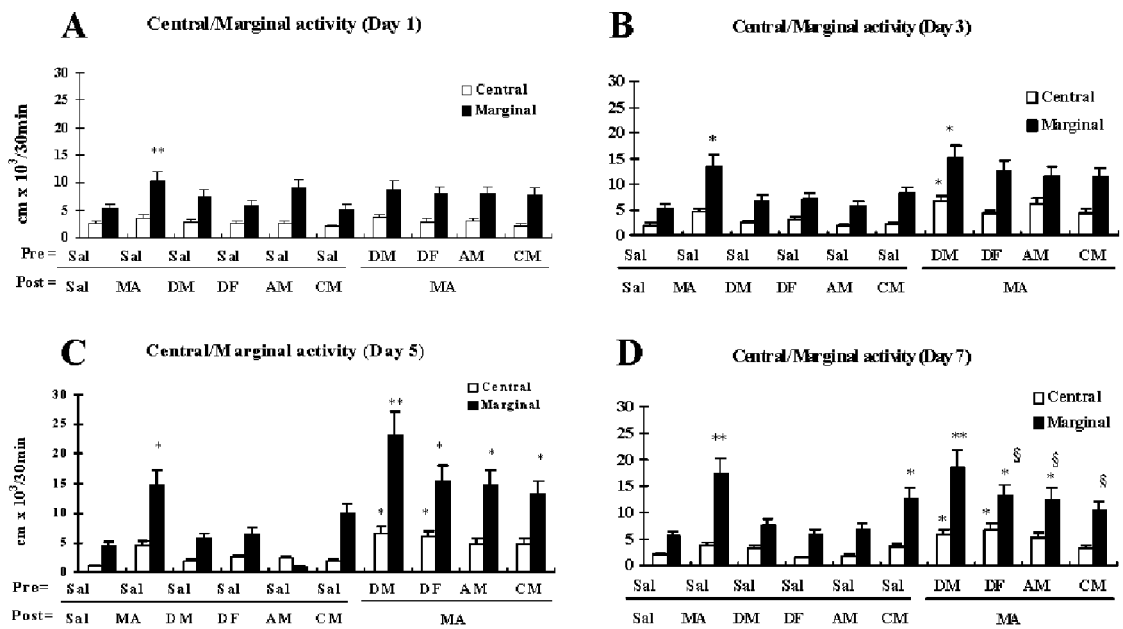
FIGS. 39A-39D show effect of morphinans on the MA-induced hyperactivity in the mice. Each morphinan (20 mg/kg, i.p.) was administered 30 minutes prior to MA (1 mg/kg, i.p.). All treatments were performed for 7 days. Each value is the mean±S.E.M. of 6 animals. *P<0.05 vs. saline, **P<0.01 vs. saline, §P<0.05 vs. Sal+MA (ANOVA with DMR test).

The Effects of Morphinans (DM, DF, AM, or CM) on Methamphetamine (MA)-induced Hyperlocomotion in Mice Saline alone did not significantly alter locomotor activity. MA (1 mg/kg) caused an increase in locomotor activity over time. Treatment with DM (20 mg/kg) (30 min before every MA) did not affect MA (1 mg/kg, i.p./day×7)-induced hyperactivity. In contrast, DF, AM or CM are consistently effective in attenuating hyperlocomotion induced by MA. (FIG. 39).

Experimental Example 3.11

Figure 40:
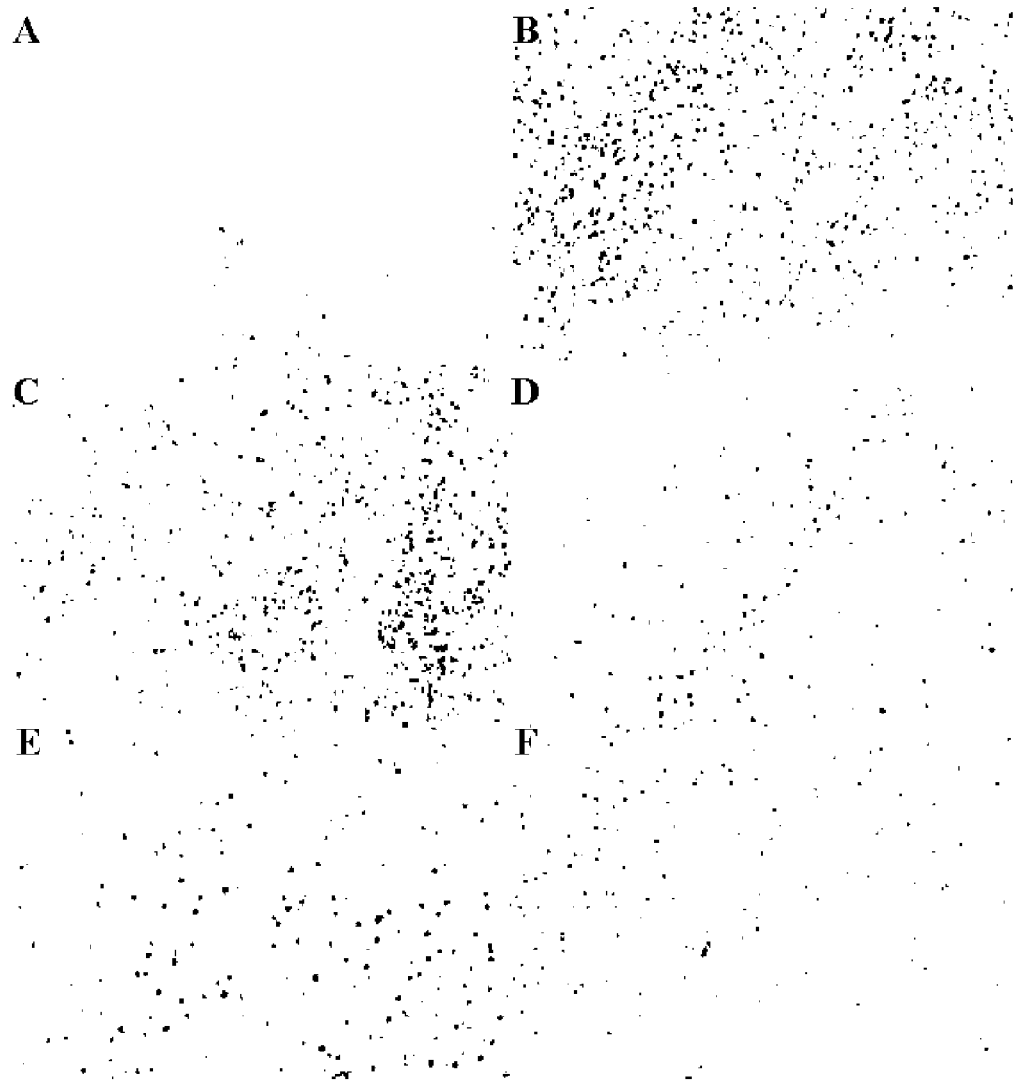
FIG. 40 shows representative photomicrographs showing Fos-related antigen-immunoreactive neurons in the dorsolateral striatum of mice brains. A: Saline, B: MA (1 mg/kg, i.p.), C: DM (20 mg/kg, i.p.)+MA, D: DF (20 mg/kg, i.p.)+MA, E: AM (20 mg/kg, i.p.)+MA, F: CM (20 mg/kg, i.p.)+MA. Magnification=100×.

The Effects of Morphinans (DM, DF, AM or CM) on Methamphetanine (MA)-induced Fos-Related Antigen-immunoreactivity (FRA-iR) in the Striatum of the Mice Little induction of FRA-IR was observed in the absence of MA. Prolonged treatment with MA (1 mg/kg, i.p./day×7) markedly induced FRA-IR in the striatum. DM did not affect this induction of FRA-IR mediated by MA. In contrast, MA-induced FRA-IR was apparently attenuated by the treatment with DF, AM, or CM (FIG. 40).

Experimental Example 3.12

Figure 41:
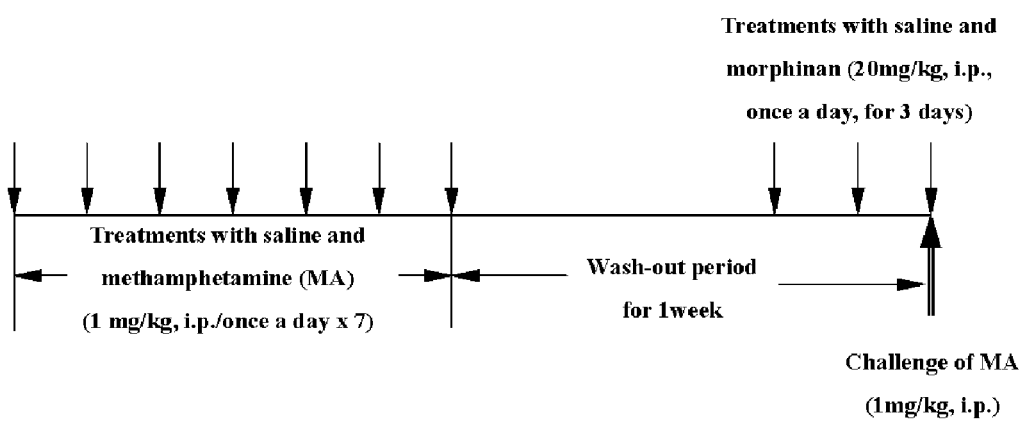
FIGS. 41A-41B show effects of morphinans on the MA-induced sensitization in the mice. Morphinans (20 mg/kg, i.p.) were administered last 3 days of wash-out period. Each value is the mean±S.E.M. of 6 animals. *P<0.05 vs. Sal+Sal, **P<0.01 vs. Sal+Sal, #P<0.05 vs. corresponding dose of Sal+MA (ANOVA with DMR test).
Figure 41:
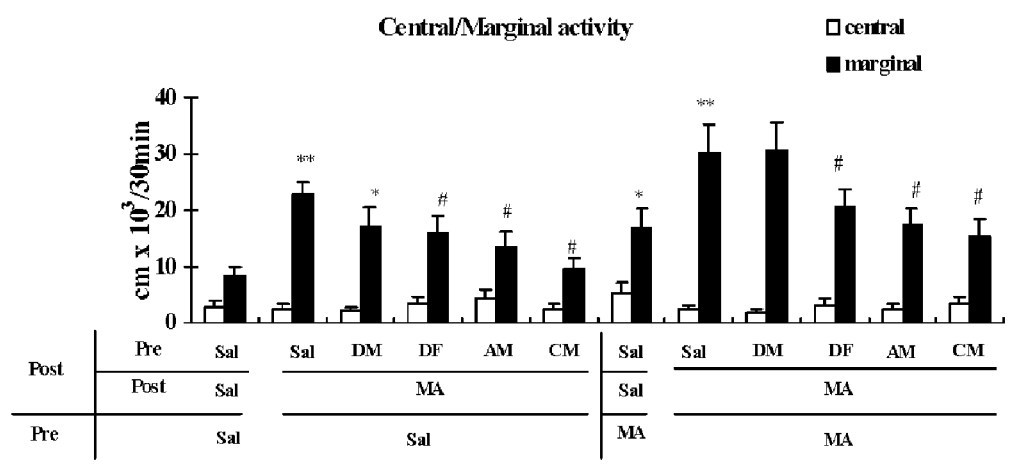

The Effects of DM, DF, AM or CM in Response to Methamphetamine (MA)-induced Behavioural Sensitization Saline-treated animals did not show any specific behavioural effects under the video-tracking system. MA induced significant behavioural sensitization [locomotor activity of the animals receiving a single challenge of MA vs. locomotor activity of animals pretreated with MA (1 mg/kg, i.p./day×7) at one week before a single challenge of MA, $P<0.05$]. DM (20 mg/kg, i.p.) did not alter behavioural sensitization by MA. However, with a 20 mg/kg dosage of the DF, AM or CM, the MA-evoked behavioural sensitazation was significantly reduced ($P<0.05$) (FIG. 41).

Experimental Example 3.13

Figure 42:
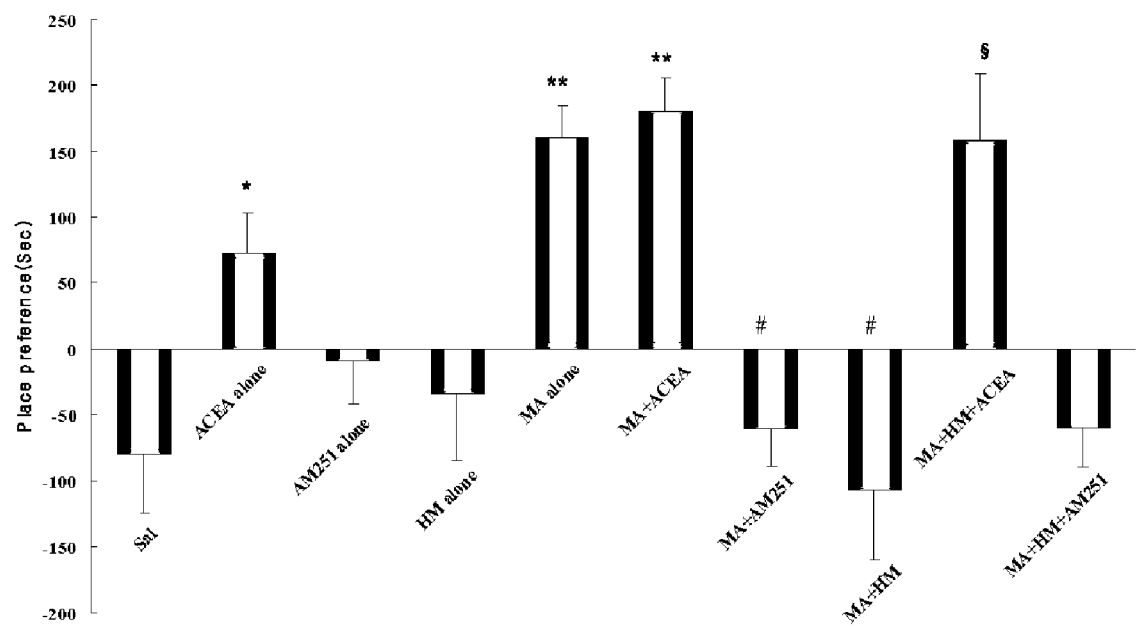
FIG. 42 shows effect of cannabinoid CB1 receptor modulation on the HM-mediated action in response to MA-induced conditioned place preference. Each value is the mean±S.E.M. of 10 animals. *P<0.05 or **P<0.01 vs. Sal, #P<0.01 vs. MA alone, §P<0.01 vs. MA+HM (ANOVA with DMR test).

The Effects of Cannabinoid CB1 Receptor Agonist (ACEA) or CB1 Receptor Antagonist (AM 251) on HM-mediated Pharmacological Action in Response to MA-induced CPP Neither saline-, AM 251 (0.3 mg/kg, i.p.)-treated nor HM (20 mg/kg)-treated animals showed any CPP responses. In contrast, ACEA (2 mg/kg, i.p.)-treated animals showed CPP effects ($P<0.05$ vs. saline-treated animals). MA produced significant CPP effects ($P<0.01$). ACEA did not alter CPP effects by MA. However, AM 251 ($P<0.05$) or HM ($P<0.01$) significantly reduced the CPP produced by MA. AM 251 did not significantly affect HM's effect in response to MA-induced CPP. In contrast, ACEA significantly counteracted ($P<0.01$) HM's effects on the MA-induced CPP (FIG. 42).

Experimental Example 3.14

Figure 43:
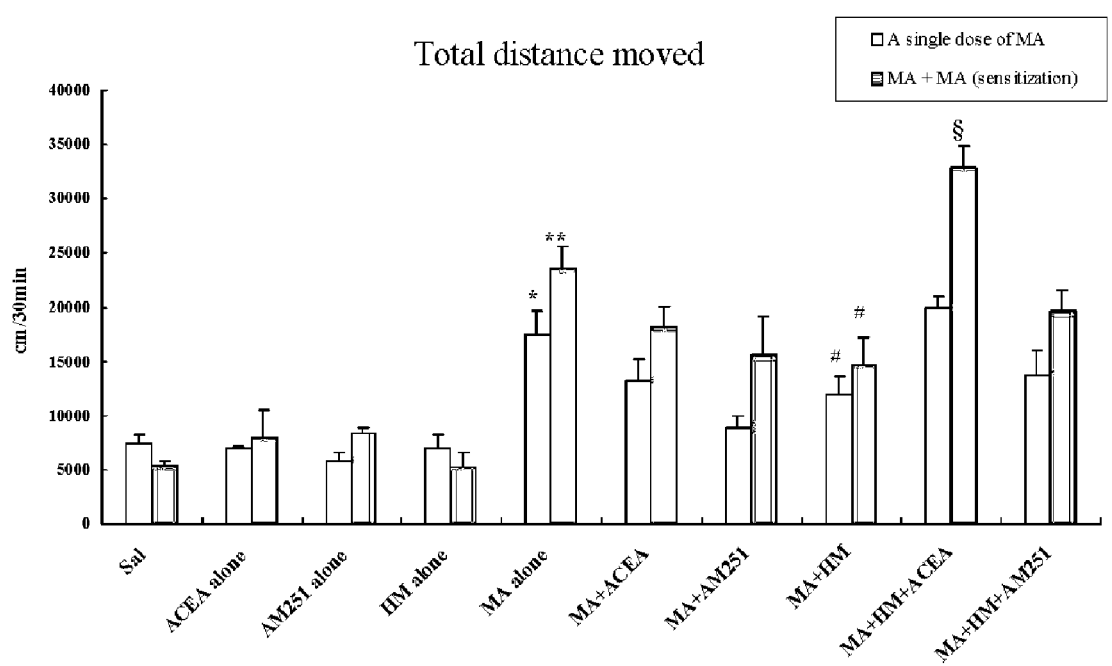
FIG. 43 shows effect of cannabinoid CB1 receptor modulation on the HM-mediated action in response to MA-induced behavioral sensitization. Each value is the mean±S.E.M. of 10 animals. *P<0.02, **P<0.01 vs. Sal, #P<0.05 vs. MA alone, §P<0.01 vs. MA+HM (ANOVA with DMR test).

The Effects of Cannabinoid CB1 Receptor Agonist (ACEA) or CB1 Receptor Antagonist (AM 251) on HM-mediated Pharmacological Action in Response to Methamphetamine (MA)-induced Behavioural Sensitization Neither saline-, AM 251 (0.3 mg/kg)-, ACEA (2 mg/kg)-treated nor HM (20 mg/kg)-treated animals showed any behavioural effects. MA induced significant behavioural sensitization [locomotor activity of the animals receiving a single challenge of MA vs. locomotor activity of animals pretreated with MA (1 mg/kg, i.p./day×7) at one week before a single challenge of MA, $P<0.01$]. Neither ACEA nor AM 251 influenced behavioural sensitization by cocaine. However, HM significantly reduced ($P<0.05$) the behavioural sensitazation produced by MA. Although ACEA significantly reversed HM's effect ($P<0.05$) on the MA-induced sensitization, AM 251 did not affect MA sensitization (FIG. 43).

REFERENCES

1. Abercrombie M. Estimation of nuclear population from microtome sections, Anat. Rec. 1946; 94: 239-247.

2. Ault D T, Radeff J M, Werling L L. Modulation of [$^3$H]dopamine release from rat nucleus accumbens by neuropeptide Y via a sigma1-like receptor. J. Pharmacol Exp Ther 1998; 284:553-560.

3. Bing G, Zhang Y, Watanabe Y, McEwen B S, Stone E A. Locus coeruleus lesions potentiate neurotoxic effects of MPTP in dopaminergic neurons of the substantia nigra. Brain Res. 1994; 668: 261-265.

4. Carlsson M L. Are the disparate pharmacological profiles of competitive and uncompetitive NMDA antagonists due to different baseline activities of distict glutamatergic pathways? (Hypothesis). J Neural Transm [Gen Sect] 1993; 94: 1-10

5. Choi D W. Dextrorphan and dextromethorphan attenuate glutamate neurotoxicity. *Brain Res.* 1987; 403: 333-336.

6. Domino E F, Sheng J. N-methyl-D-aspartate receptor antagonist and dopamine D1 ans D2 agonist interactions in 1-methyl-4-phenyl-1,2,3,6-tetrahysropyridine-induced hemi-parkinsonian monkeys. J. pharmacol Exp Ther. 1993; 264:221-225

7. Chou Y C, Liao J F, Chang W Y, Lin M F, Chen C F. Binding of dimemorfan to sigma-1 receptor and its anticonvulsant and locomotor effects in mice, compared with dextromethorphan and dextrorphan. Brain Res 1999; 821:516-519.

8. Cranston J W, Yoast R. Abuse of dextromethorphan. Arch. Fam. Med. 1999; 8: 99-100

9. Ferkany J W, Borosky S A, Clissold D B, Pontecorvo M J, Dextromethorphan inhibits NMDA induced convulsions. Eur J Pharmacol 1988; 151:151-154.

10. Gao H M, Hong J S, Zhang W, Liu B. Synergistic dopaminergic neurotoxicity of the pesticide rotenone and inflammogen lipopolysaccharide: Relevance to the etiology of Parkinson's disease. J. Neurosci 2002; 22:782-790

11. Hayashi T, Su T P. Sigma-1 receptor ligands: potential in the treatment of neuropsychiatries disorders. CNS Drugs 2004; 18:269-284.

12. Holzman S G, Discriminative stimulus effects of dextromethorphan in the rat. Psychopharmacology 1994; 116: 249-254.

13. Jhoo W K, Shin E J, Lee Y H, Cheon M A, Oh K W, Kang S Y, Lee C, Yi B C, Kim H C. Dual effects of dextromethorphan on cocaine-induced conditioned place preference in mice. Neurosci. Lett. 2000; 288:76-80.

14. Kaur S, Starr M S. Antiparkinsonian action of dextromethorphan in the reserpine-treated mouse. Eur J Pharmacol 1995; 280:159-166.

15. Kim H C, Jhoo W K. Alterations in motor activity induced by high dose oral administration of dextromethorphan throughout two consecutive generations in mice. Arch Pharm Res 1995; 18:146-152.

16. Kim H C, Jhoo W K, Kwon M S, Hong J S. Effects of chronic dextromethorphan administration on the cellular immune responses in mice. Arch Pharm Res. 1995 18; 267-270.

17. Kim H C, Pennypacker K, Bing G, Bronstein D, McMillian M, Hong J S. The effect of dextromethorphan on kainic acid-induced seizures in the rat. Neurotoxicology 1996; 17:375-386.

18. Kim H C, Suh H W, Bronstein D, Bing G, Wilson B, Hong J S. Dextromethorphan blocks opioid peptide gene expression in the rat hippocampus induced by kainic acid, Neuropeptides 1997; 31:105-112.

19. Kim H C, Lee P H, Jhoo W K. The complex pharmacological action of dextromethorphan; requirement of development of neuroprotective dextromethorphan analogs with negligible psychotomimetic effects. *International Symposium on the* Molecular Monitoring in the Neuroscience Field, Nagoya, Japan. 1998; 3:1-2.

20. Kim H C, Bing G, Jhoo W K, Ko K H, Kim W K, Lee D C, Shin E J, Hong J S. Dextromethorphan modulates the AP-1 DNA binding activity induced by kainic acid. Brain Res 1999; 824:125-132.

21. Kim H C, Jhoo W K, Choi D Y, Im D H, Shin E J, Suh J H, Floyd R A, Bing G. Protection of methamphetamine nigrostriatal toxicity by dietary selenium. Brain Res. 1999; 851: 76-86.

22. Kim H C, Jhoo W K, Shin E J, Bing G. Selenium deficiency potentiates methamphetamine-induced nigral neuronal loss; comparison with MPTP model. Brain Res. 2000; 862:247-252.

23. Kim H C, Ko K H, Kim W K, Shin E J, Kang K S, Shin C Y, Jhoo W K. Effects of dextromethorphan on the seizures induced by kainate and the calcium channel angonist BAY k-8644: Comparison with the effects of dextrorphan. Behav. Brain Res. 2001; 120:169-175.

24. Kim H C, Nabeshima T, Jhoo W K, Ko K H, Kim W K, Shin E J, Cho M, Lee P H. Anticonvulsant effects of new morphinan derivatives. Bioorg. Med. Chem. Lett. 2001; 11: 1651-1654.

25. Kim H C, Bing G, Shin E J, Jhoo H S, Cheon M A, Lee S H, Choi K H, Kim J L, Jhoo W K. Dextromethorphan affects cocaine-mediated behavioral pattern in parallel with a long-lasting fos-related antigen-immunoreactivity. Life Sci. 2001; 69: 615-624.

26. Kim H C, Bing G, Jhoo W K, Kim W K, Shin E J, Im D H, Kang K S, Ko K H. Metabolism to dextrorphan is not essential for dextromethorphan's anticonvulsant activity against kainate in mice. Life Sci 2003; 72:769-783.

27. Kim H C, Shin C Y, Seo D O, Jhoo J H, Jhoo W K, Kim W K, Shin E J, Lee Y H, Lee P H, Ko K H. New morphinan derivatives with negligible psychotropic effects attenuate convulsions induced by maximal electroshock in mice. Life Sci. 2003; 72: 1883-1895.

28. Kim W G, Mohney R P, Wilson B, Jeohn G H, Liu B, Hong J S. Regional difference in susceptibility to lipopolysaccharide-induced neurotoxicity in the rat brain: role of microglia. J. Neurosci. 2000; 20:6309-6316.

29. Kita T, Wagner G C, Nakashima T. Current research on methamphetamine-induced neurotoxicity: animal model of monoamine disruption. J. Pharmacol Sci 2003; 92:178-195.

30. Klockgether, T, Turski L, Honore T, Zhang Z, Gash D M, Kurlan R, Greenmayre J T. The AMPA receptor antagonist NBQX has antiparkinsonian effects in monoamine depleted rats and MPTP treated monkeys. Ann Neurol 1991; 30: 717-723

31. Kobayashi T, Matsuno K, Murai M, Mita S. Sigma1 receptor subtype is involved in the facilitation of cortical dopaminergic transmission in the rat brain. Neurochem Res 1997; 22:1105-1109.

32. Lipton S A. Prospects for clinically tolerated NMDA antagonists: open channel blockers and alternative redox states of nitric oxide Trends Nuerosci 1993; 16: 527-532.

33. Liu Y, Qin L, Li G, Zhang W, An L, Liu B, Hong J S, Dextromethorphan protects dopaminergic neurons against inflammation-mediated degeneration through inhibition microglial activation. J. Pharmacol Exp Ther 2003; 305:212-218.

34. Löbscher W, Hönack D. Differences in anticonvulsant potency and adverse effects between dextromethorphan and dextrorphan in amygdala-kindled and non-kindled rats. Eur J Pharmacol 1993; 238:191-200.

35. Montastruc J L. Recent advances in the clinical pharmacology of Parkinson's disease. Therapie 1991; 29:293-303.

36. Montastruc J L, Rascol O, Senard J M. Current status of dopamine agonists in Parkinson's disease management. Drugs 1993; 46:384-393.

37. Mucha R F, Van der Kooy D, O'Shaughnessy M, Bucenieks P. Drug reinfoecement studied by the use of place conditioning in rat. Brain Res 1982; 243:91-105.

38. Murakami M, Inukai N, Nagano N. Studies on morphinan derivatives I. The synthesis of several new 3-substituted derivatives of N-methylmorphinan ring having antitussive activities. Chem Pharm Bull 1972; 20: 1699-705.

39. Noda Y, Miyamoto Y, Mamiya T, Kamei H, Furukawa H, Nabeshima T. Involvement of dopaminergic system in phencyclidine-induced place preference in mice pretreated with phencyclidine repeatedly. Journal of Pharmacology and Experimental Therapeutics 1998; 286:44-51.

40. Orr C F, Rowe D B, Halliday G M. An inflammatory review of Parkinson's disease. Prog. Neurobiol. 2002; 68:325-340.

41. Park S Y, Shin E J, Jhoo W K, Ko K H, Kim W K, Kim H C. Dimemorfan provides neuroprotection via activation of sigma-1 receptor and blocking L-type calcium channels; models of kainate and BAY k-8644. Society for Neuroscience (abstract) 2002; 32: Program No 798.5

42. Peeters M, Romieu P, Maurice T, Su T P, Maloteaux J M, Hermans E. Involvement of the sigma receptor in the modulation of dopaminergic transmission by amantadine. Eur J Neurosci 2004; 19:2212-2220.

43. Pender E S, Parks B R. Toxicity with dextromethorphan-containing preparations: A literature review and report of two additional cases. Pediat Emerg Care 1991; 7: 163-5.

44. Price, L H, Lebel J. Dextromethorphan-induced psychosis. Am. J. Psychiatry 2000; 157, 304.

45. Rammer L, Holmgren P, Sandler H. Fatal intoxication by dextromethorphan: A report on two cases. Forensic Sci Int 1988; 37: 766-768.

46. Shin E J, Nabeshima T., Lee P H, Kim W K, Ko K H, Jhoo J H, Jhoo W K, Cha J Y, Kim H C. Dimemorfan prevents seizures induced by the L-type calcium channel activator BAY k-8644 in mice. Behav. Brain Res. 2004; 151: 267-276

47. Starr M S, Starr B S, Kaur S. Stimulation of basal and L-DOPA-induced motor activity by glutamate antagonists in animal models of Parkinson's disease. Neurosci Neurobehav Rev 1997; 21:437-446.

48. Su T P. (receptors-Putative links between nervous, endocrine and immune systems. Eur J Biochem 1991; 200: 633-642.

49. Thompson K W, Wasterlain C G. Dextromethorphan and its combination with phenyloin facilitate kindling. Neurology 1993; 43:992-994.

50. Tortella F C, Pellicano M, Bowery N G. Dextromethorphan and neuromodulation: old drug coughs up new activities. Trends Pharmacol Sci 1989; 10:501-507.

51. Tortella F C, Robles L, Witkin J M, Newman A H. Novel anticonvulsant analogs of dextromethorphan: improved efficacy, potency, duration and side-effect profile. J Pharmacol Exp Ther 1994; 268: 727-733.

52. Verhagen Metman L, Blanchet P J, van den Munckhof P, Del Dotto P, Natte R, Chase T N. A trial of dextromethorphan in parkinsonian patients with motor response complications. Mov Disord 1998; 13:414-417.

53. Wolfe T R, Cravati E M. Massive dextromethorphan ingestion and abuse. Am. J. Emerg. Med. 1995; 13: 174-176.

54. Wu D, Otton S V, Kalow W, Sellers E M. Effects of route of administration on dextromethorphan pharmakinetics and behavioral response in the rat. J Pharmacol Exp Ther 1995; 274:1431-37.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of treating symptoms of Parkinson's disease comprising administering to a patient or animal in need of such treatment an effective anti-Parkinsonism amount of a composition comprising 3-hydroxymorphinan (HM) as the active agent.

2. The method of claim 1, wherein the composition is in sustained release dosage form.

3. The method of claim 1, wherein the composition further comprises a neuroprotective agent.

4. The method of claim 2, wherein the composition comprises a digestible capsule, which encloses the morphinan or pharmaceutically acceptable salt thereof.

5. The method of claim 1, wherein the composition is administered at 250 milligrams/day or less.

* * * * *